(12) United States Patent
Fulkerson et al.

(10) Patent No.: US 11,904,130 B2
(45) Date of Patent: Feb. 20, 2024

(54) FLUID ACCESS DEVICES AND METHODS

(71) Applicant: University of Washington, Seattle, WA (US)

(72) Inventors: Barry Fulkerson, Seattle, WA (US); Jeremy Barribeau, Seattle, WA (US); Anna Galperin, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 17/699,636

(22) Filed: Mar. 21, 2022

(65) Prior Publication Data
US 2022/0305185 A1  Sep. 29, 2022

Related U.S. Application Data

(60) Provisional application No. 63/282,912, filed on Nov. 24, 2021, provisional application No. 63/165,099, filed on Mar. 23, 2021.

(51) Int. Cl.
*A61M 39/10* (2006.01)
*A61M 1/36* (2006.01)
(Continued)

(52) U.S. Cl.
CPC ........ *A61M 39/105* (2013.01); *A61M 1/3653* (2013.01); *A61M 1/3661* (2014.02); *A61M 1/362265* (2022.05); *A61M 39/14* (2013.01); *A61M 39/26* (2013.01); *A61B 5/150992* (2013.01); *A61M 2039/1022* (2013.01); *A61M 2039/1027* (2013.01); *A61M 2039/1066* (2013.01); *A61M 2039/267* (2013.01); *A61M 2205/3303* (2013.01);
(Continued)

(58) Field of Classification Search
CPC .. A61M 2039/1027; A61M 2039/1066; A61M 1/3661
See application file for complete search history.

(56) References Cited

U.S. PATENT DOCUMENTS 9,808,647 B2   11/2017  Rhodes et al.
10,984,903 B2   4/2021  Doyle et al.
(Continued)

FOREIGN PATENT DOCUMENTS

WO    2015192108 A1   12/2015
WO    2021122242 A1    6/2021

OTHER PUBLICATIONS

PCT/US22/21198 International Search Report dated Aug. 2, 2022.
(Continued)

*Primary Examiner* — Jenna Zhang
(74) *Attorney, Agent, or Firm* — Christensen O'Connor Johnson Kindness PLLC

(57) ABSTRACT

Fluid access devices include a machine-side hydraulic circuit and a patient-side hydraulic circuit, and are configurable between a connected state and at least one disconnected state. In the connected state, fluid flows between the machine-side hydraulic circuit and the patient-side hydraulic circuit. In the disconnected state, fluid does not flow between the machine-side hydraulic circuit and the patient-side hydraulic circuit. In some disconnected states, fluid recirculates through at least one of the machine-side hydraulic circuit or the patient-side hydraulic circuit in the disconnected state.

23 Claims, 46 Drawing Sheets

(51) Int. Cl.
*A61M 39/14* (2006.01)
*A61M 39/26* (2006.01)
*A61B 5/15* (2006.01)

(52) U.S. Cl.
CPC ............... *A61M 2205/3313* (2013.01); *A61M 2205/3331* (2013.01); *A61M 2205/3368* (2013.01)

(56) References Cited

U.S. PATENT DOCUMENTS

| | | | | |
|---|---|---|---|---|
| 2003/0060804 | A1* | 3/2003 | Vaillancourt | A61M 39/14 604/533 |
| 2004/0225341 | A1* | 11/2004 | Schock | A61F 7/00 607/104 |
| 2005/0256461 | A1* | 11/2005 | DiFiore | A61M 39/26 604/537 |
| 2006/0064159 | A1* | 3/2006 | Porter | A61M 1/3655 623/1.24 |
| 2006/0129134 | A1* | 6/2006 | Kerr | A61M 1/3653 604/539 |
| 2006/0260699 | A1* | 11/2006 | Edelman | A61M 39/26 137/614.04 |
| 2008/0065006 | A1* | 3/2008 | Roger | G01N 27/10 604/65 |
| 2008/0132876 | A1* | 6/2008 | Felt | A61M 39/18 604/411 |
| 2009/0099498 | A1 | 4/2009 | Demers et al. | |
| 2010/0116740 | A1 | 5/2010 | Fulkerson et al. | |
| 2011/0006520 | A1* | 1/2011 | Hall | A61M 39/00 285/383 |
| 2012/0157924 | A1* | 6/2012 | Schutz | A61M 39/26 604/175 |
| 2015/0320991 | A1 | 11/2015 | Sabin et al. | |
| 2019/0282741 | A1* | 9/2019 | Franano | A61M 60/859 |
| 2020/0129689 | A1 | 4/2020 | Jean et al. | |
| 2020/0155744 | A1* | 5/2020 | Tsoory | A61M 1/28 |
| 2021/0100946 | A1* | 4/2021 | Jansson | A61M 1/782 |
| 2021/0170090 | A1* | 6/2021 | Yuds | A61M 1/3424 |
| 2022/0265912 | A1* | 8/2022 | Altman | A61M 1/3661 |

OTHER PUBLICATIONS

Fresnius Medical Care, 2008k@home™ Wet Alert™ Wireless Wetness Detector Home User's Guide, © 2012-2014 Fresnius USA, Inc., 28 pages.

HEMOdialert™—Hemodialysis Alarm for Fistula disconnections and Blood Leak Detection Hemodialert™, © 2013 Anzacare Ltd <https://www.hemodialert.com> 1 page.

Martzy, R., et al., "A loop-mediated isothermal amplification (LAMP) assay for the rapid detection of *Enterococcus* spp. in water," Water Research 122:62-69, 2017.

Nißler, R., et al., "Remote near infrared identification of pathogens with multiplexed nanosensors," Nature Communications 11(5995): 1-12, 2020.

Redsense Medical AB, "Redsense Blood Loss Detection Alarm Unit", © 2019-2023 <https://redsensemedical.com> [retrieved Aug. 2, 2018], 13 pages.

Thet, N. T., et al., "Prototype development of the intelligent hydrogel wound dressing and its efficacy in the detection of model pathogenic wound biofilms," ACS Applied Materials & Interfaces 8(24):14909-14919, 2016.

\* cited by examiner

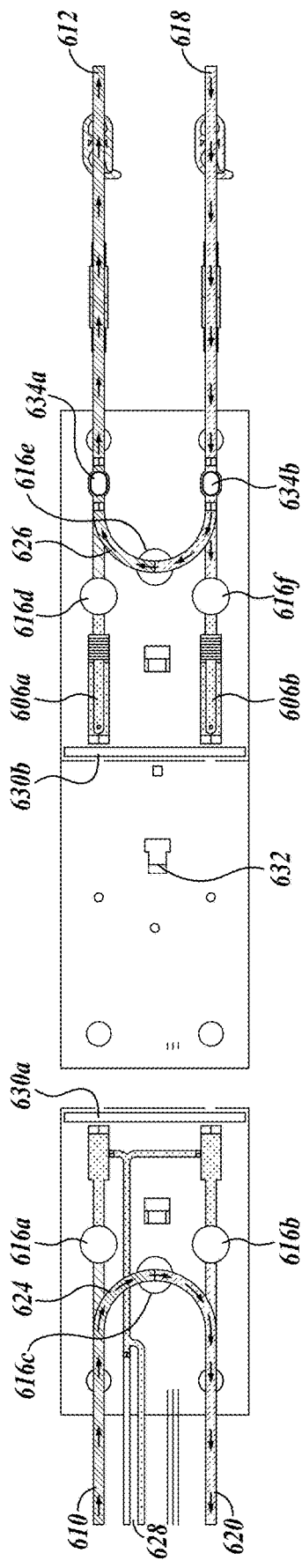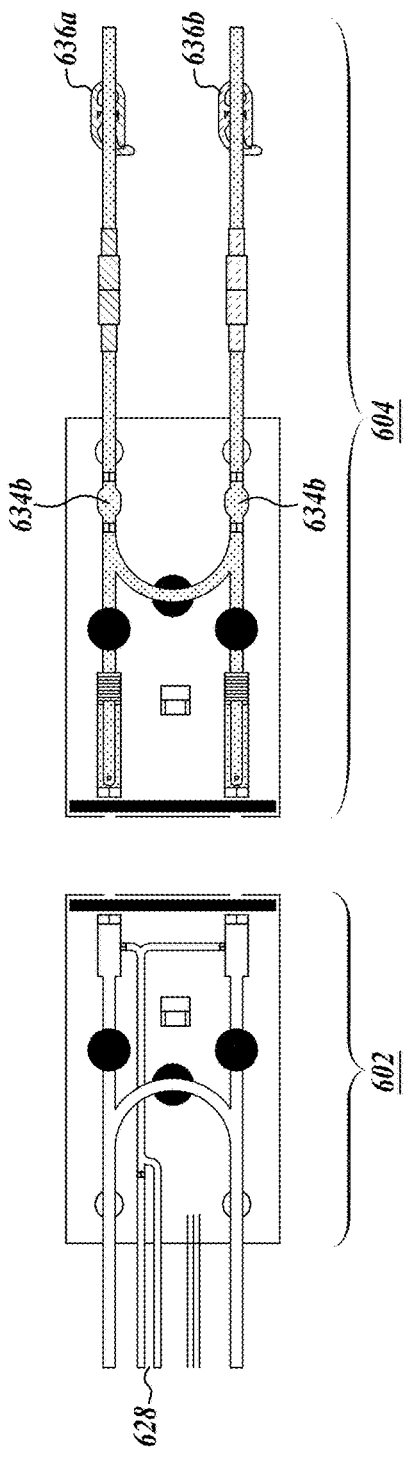
FIG. 6B *SECOND STATE: SHORT TERM DISCONNECT*
FIG. 6C *THIRD STATE: LONG TERM DISCONNECT*

STEP 1: USER INITIATES DISCONNECT

STEP 2: DISPENSE LOCK SOLUTION BOLUS

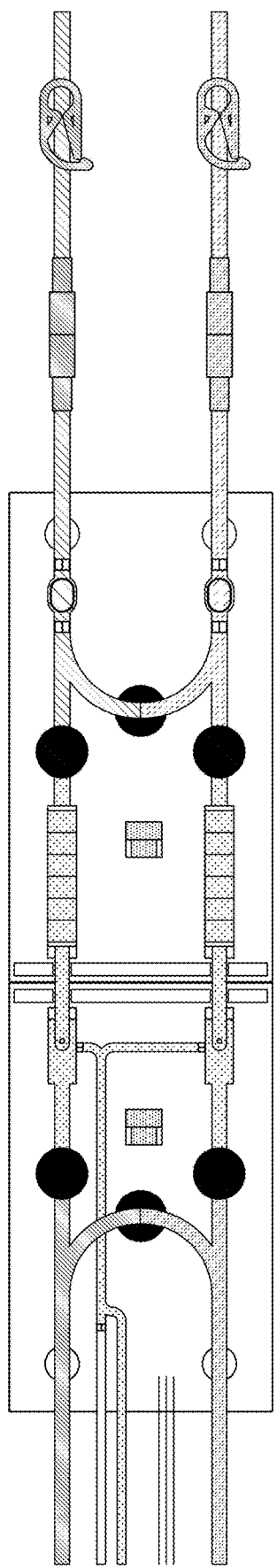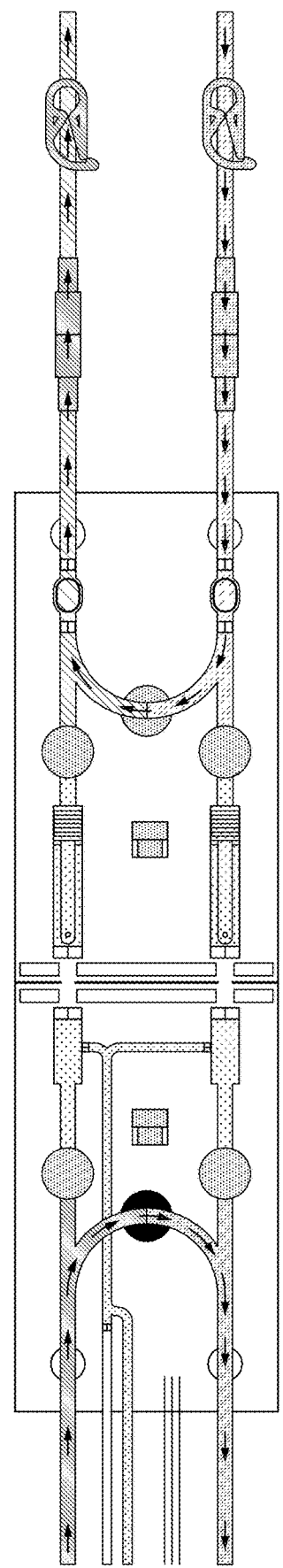

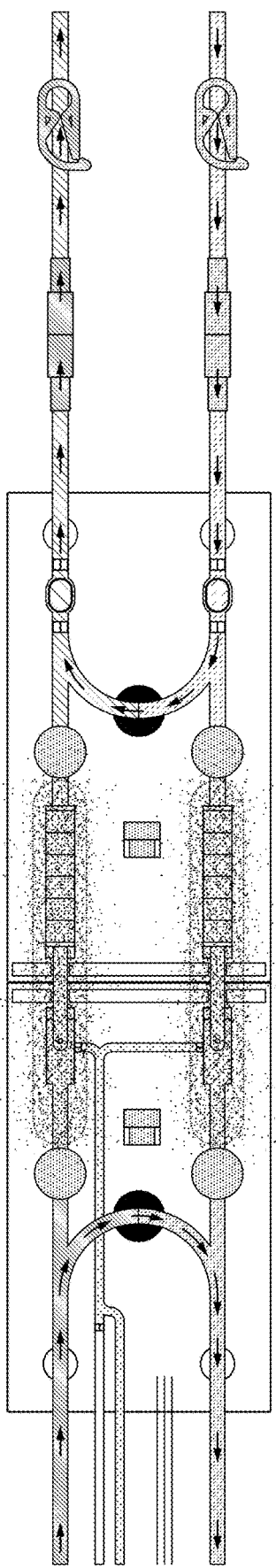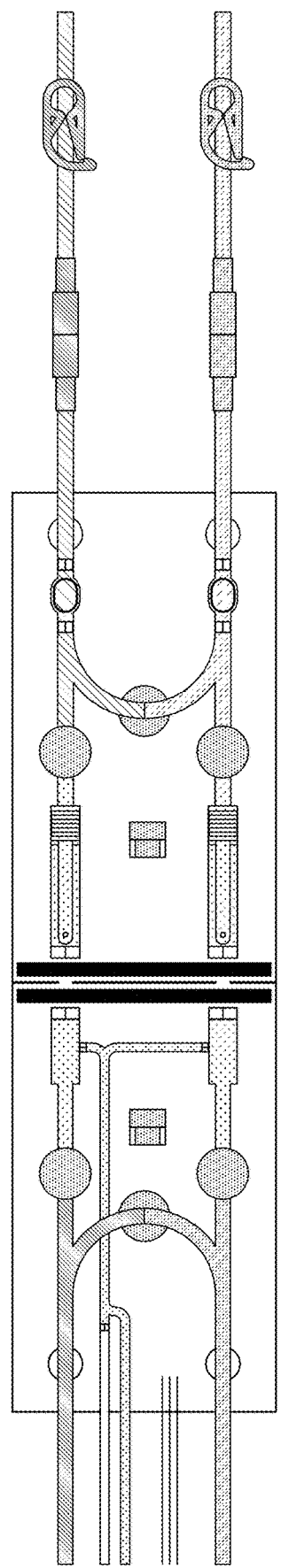

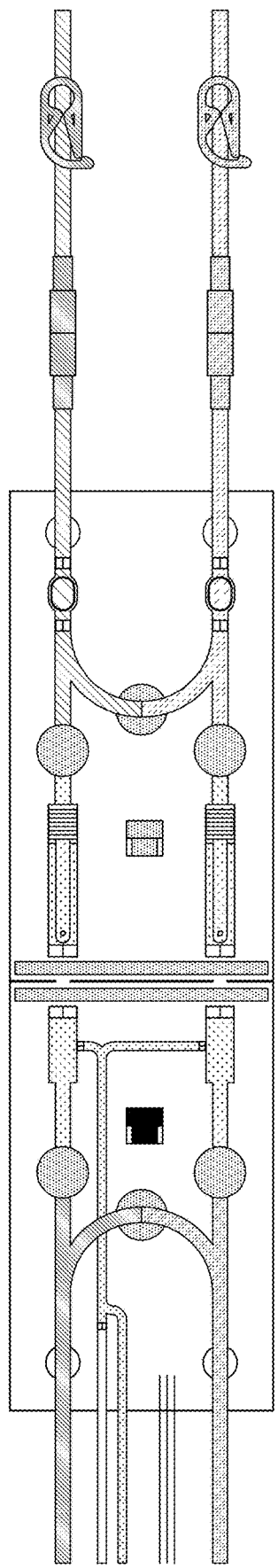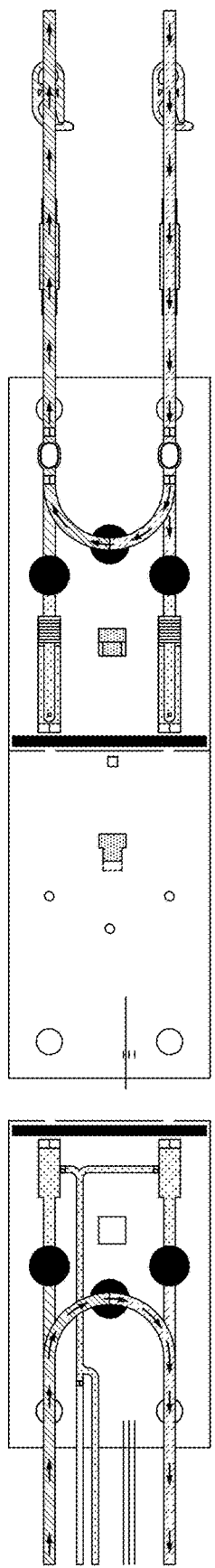

TRANSITION FROM STATE 2 (SHORT DISCONNECT) TO STATE 1 (THROUGHPUT) CLOSE UP OF STEP 7 (CLEARING BOLUS)

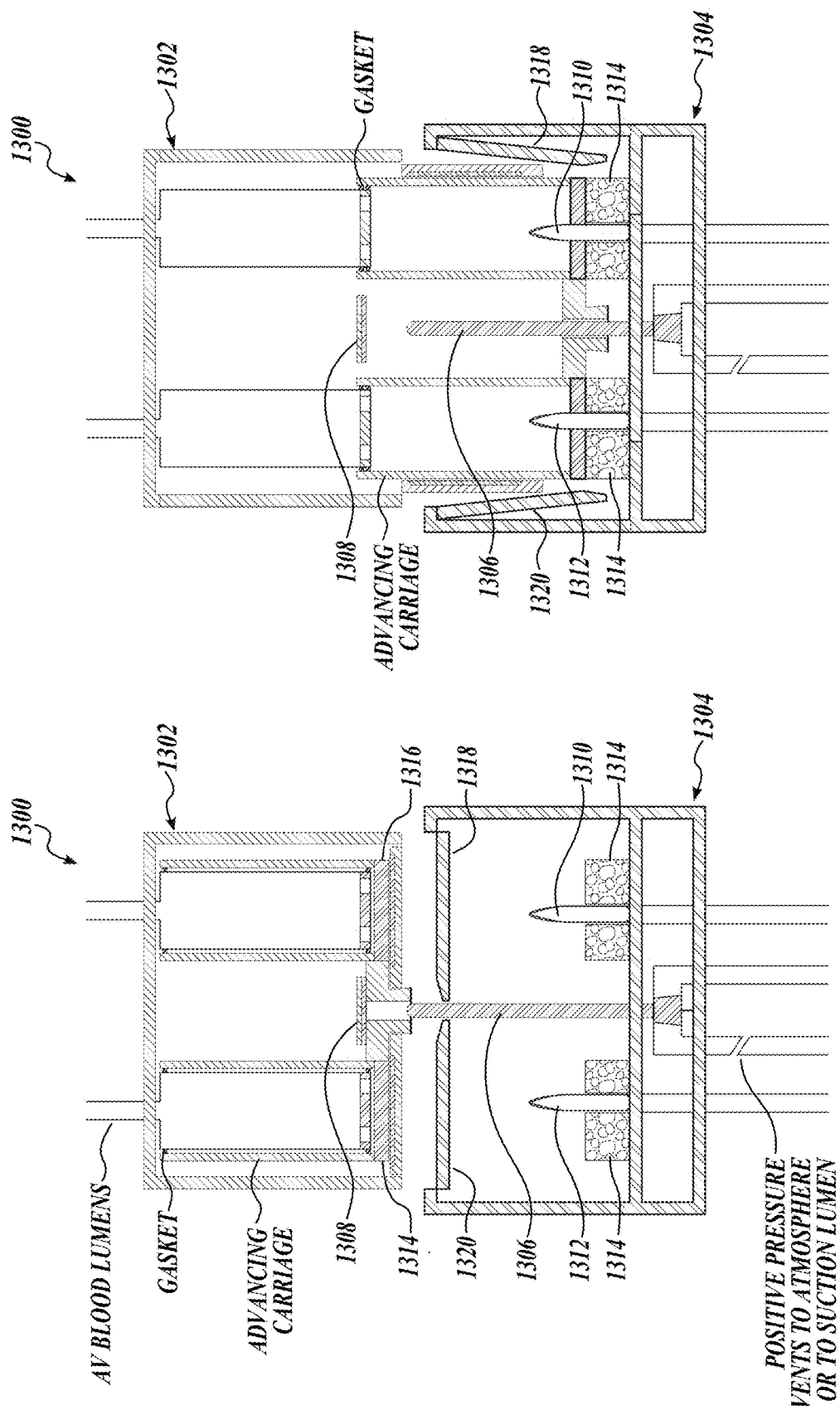

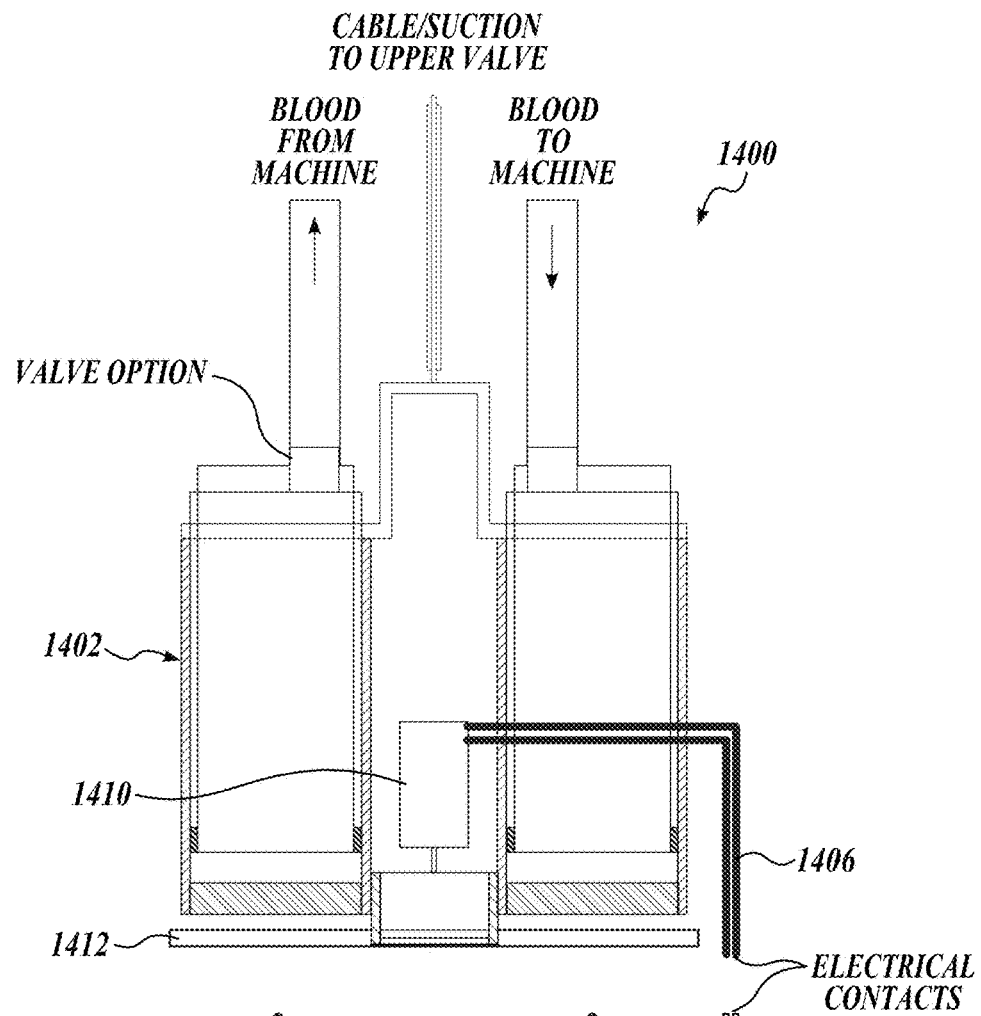
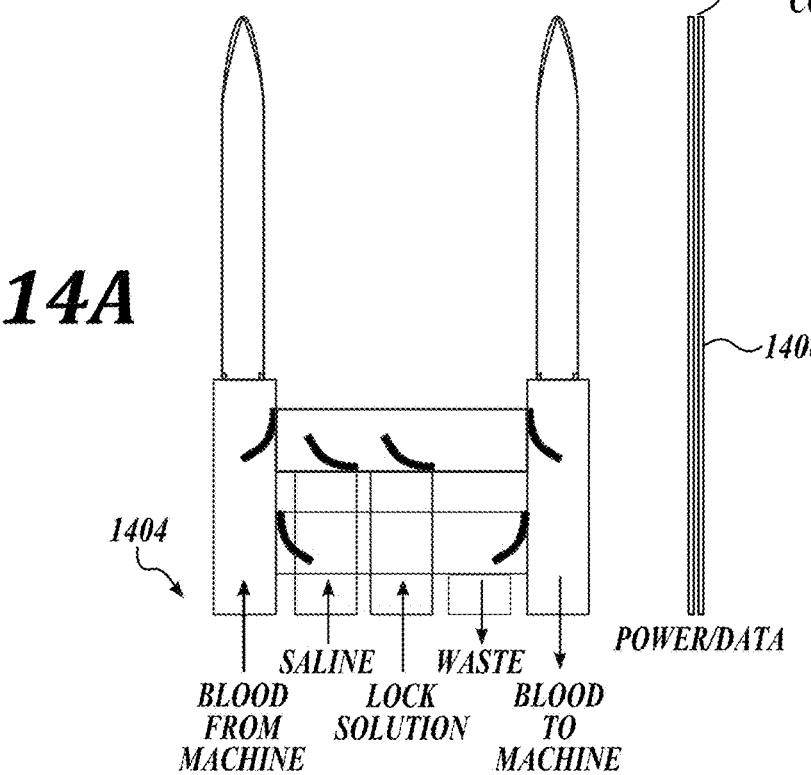
FIG. 14A

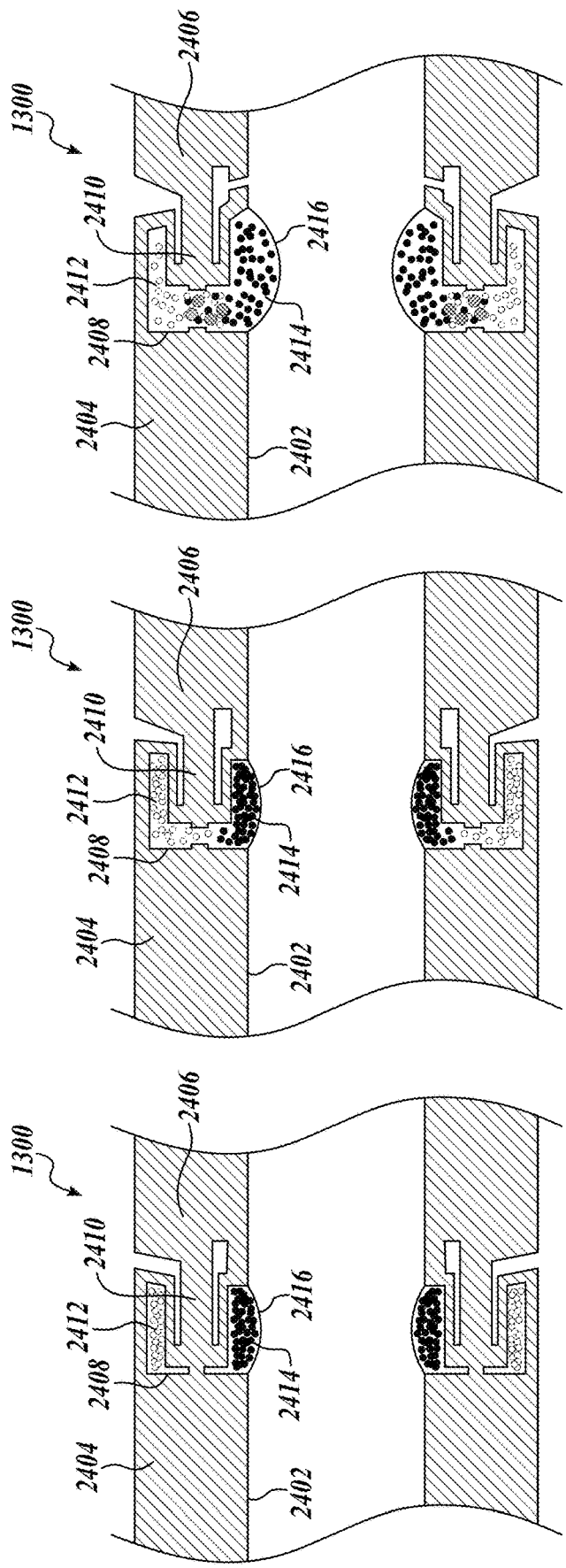

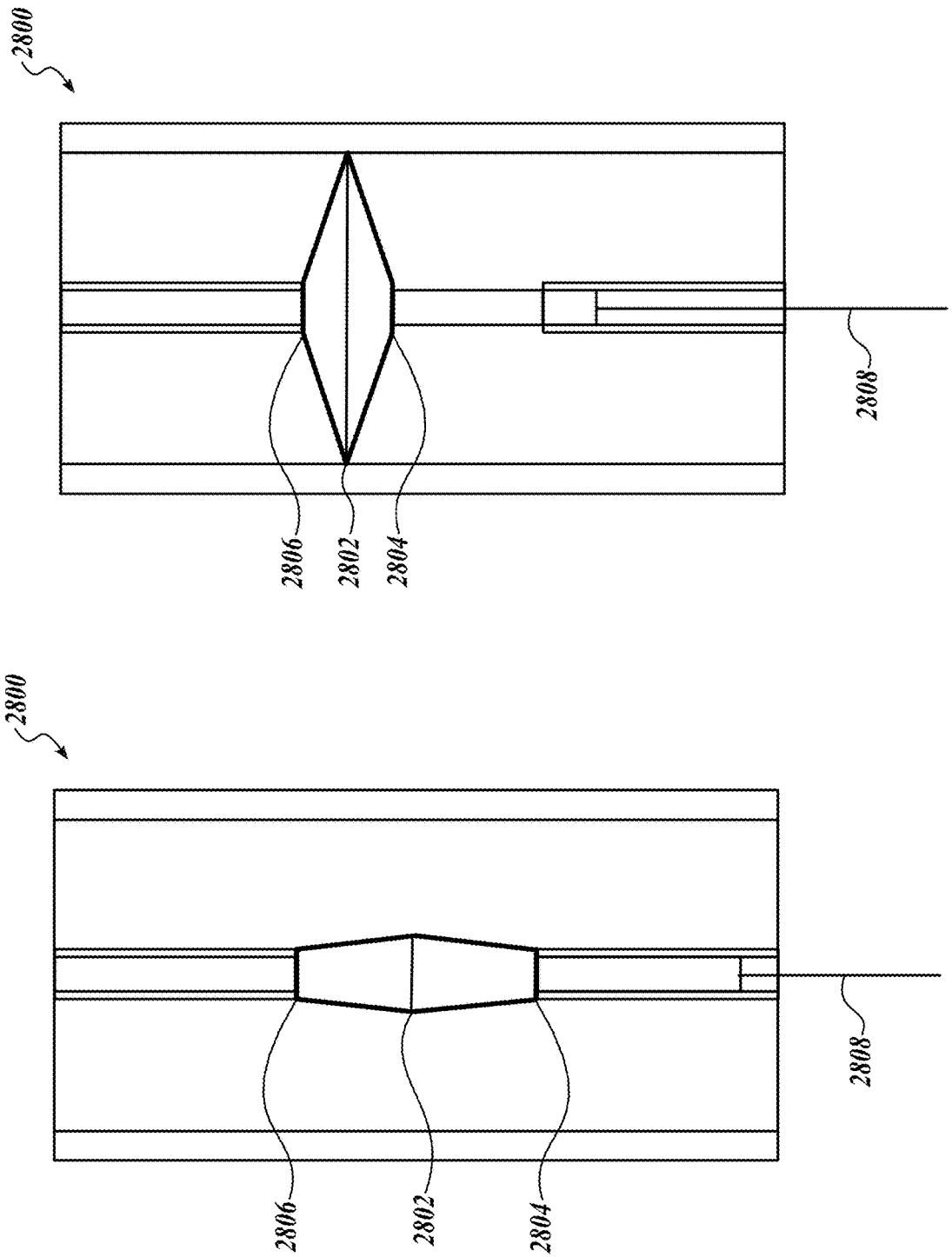

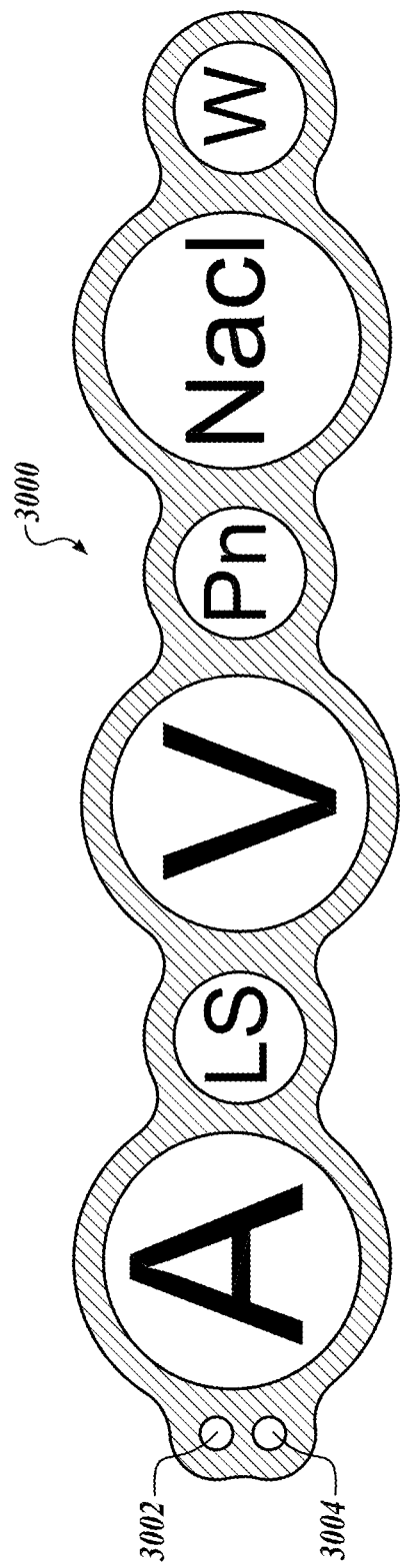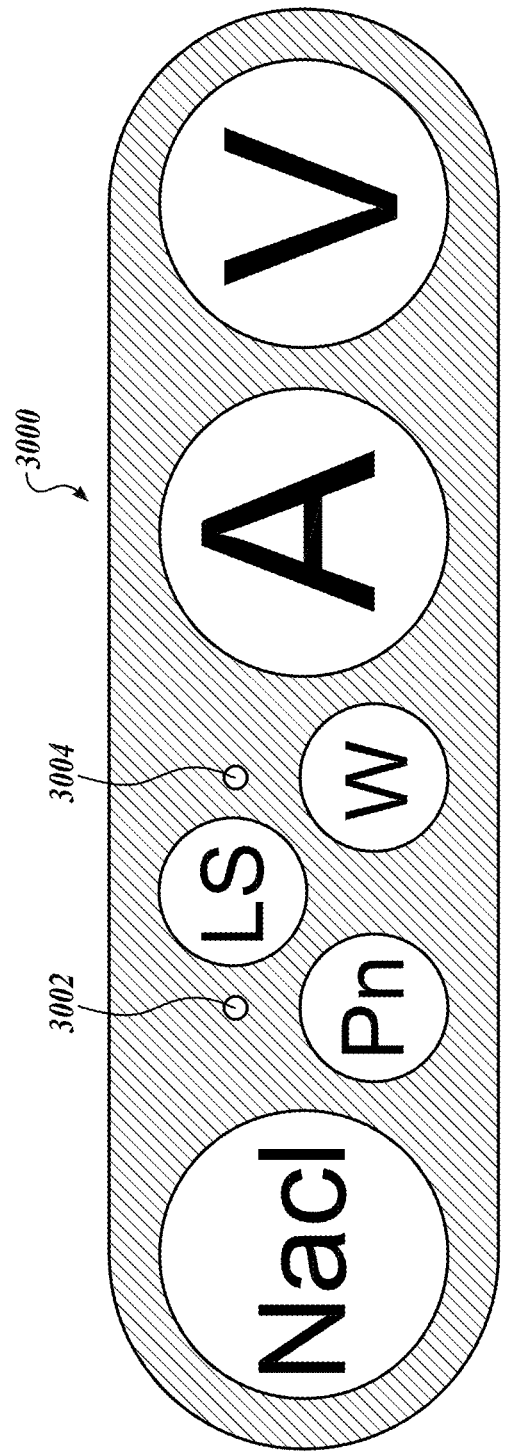
FIG. 30A                    FIG. 30B

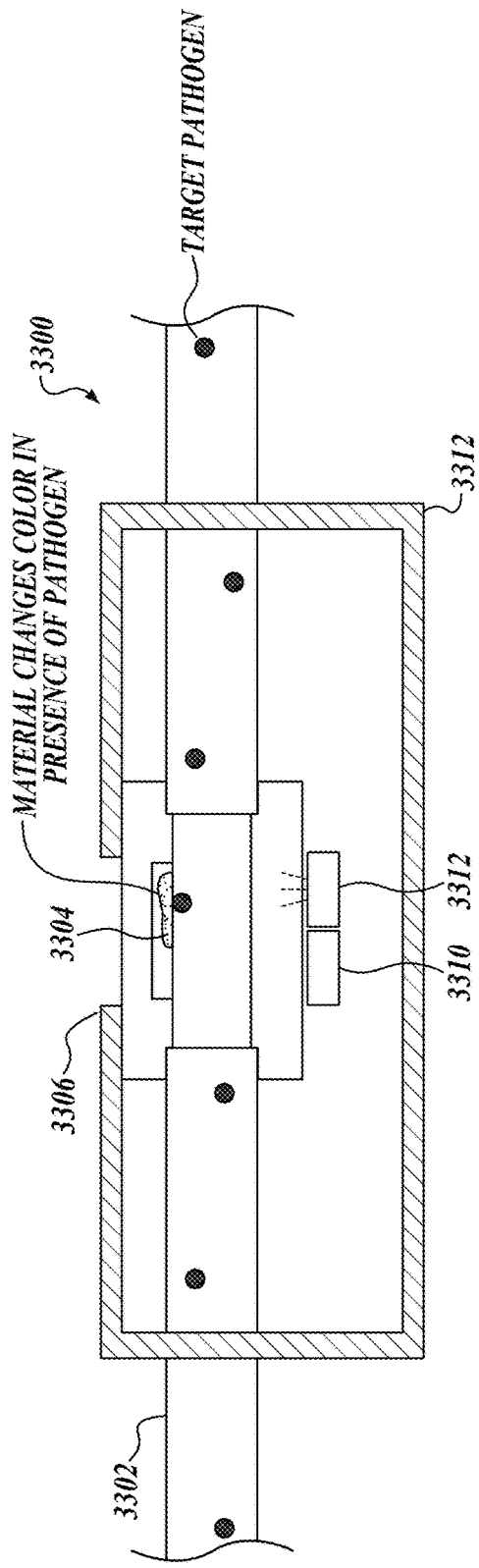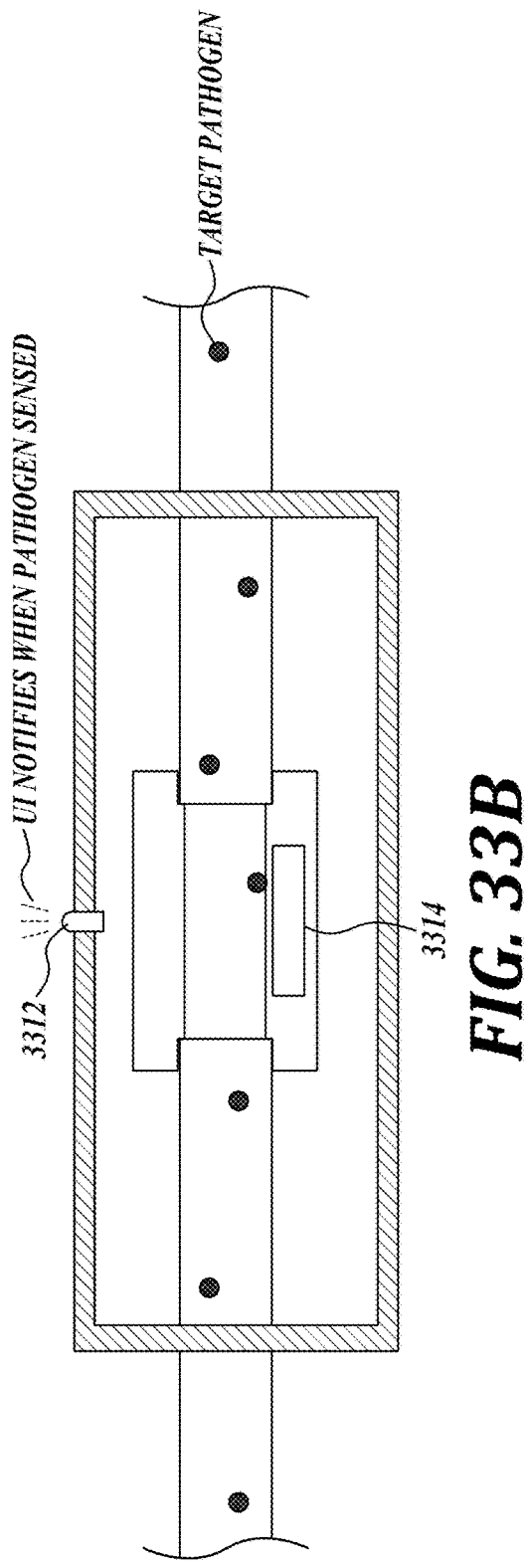

FLUID ACCESS DEVICES AND METHODS

CROSS-REFERENCE TO RELATED APPLICATIONS

This application claims the benefit under 35 U.S.C. § 119 of U.S. Provisional Patent Application No. 63/282,912, filed Nov. 24, 2021, and U.S. Provisional Patent Application No. 63/165,099, filed Mar. 23, 2021, the entire disclosures of which are hereby incorporated by reference.

BACKGROUND

Needle-based fluid access devices (e.g., graft/fistula) require specialized skill, and the cannulation causes pain and is unsuited to those with needle fear. The grafts/fistulae can fail over time, cause other health complications and are prone to dislodgement and bleeding. The alternative is a permanent central venous catheter (CVC); however, these too require specialized skills and strict adherence to aseptic technique. CVC connection requires manual execution of numerous tasks, leading to human error and an increased risk of infection. The inadequacies of these access methods are compounded when used for treatments that require multiple and/or frequent connections throughout the day. Therefore, there is a critical need to engineer a specially designed fluidic interface for use between a catheter and a machine to enable safe and reliable connection/disconnection and to manage blood flow in a safe and convenient manner.

BRIEF DESCRIPTION OF THE SEVERAL VIEWS OF THE DRAWINGS

The foregoing aspects and many of the attendant advantages of the claimed subject matter will become more readily appreciated by reference to the following detailed description, when taken in conjunction with the accompanying drawings and appendix, wherein:

FIG. 6B shows a schematic top view of a portion of the fluid access device of FIG. 6A, in a short-term disconnected state.

FIG. 6C shows a schematic top view of a portion of the fluid access device of FIG. 6A, in a long-term disconnected state.

FIG. 7A-FIG. 7H show a representative method of uncoupling a machine-side hydraulic circuit of a fluid access device of the present disclosure from a patient-side hydraulic circuit of the same.

FIG. 13A shows a schematic section view of a fluid access device in a disconnected state according to the present disclosure.

FIG. 13B shows a schematic section view of the fluid access device of FIG. 13A in a connected state.

FIG. 14A shows a schematic top view of a fluid access device in a disconnected state according to the present disclosure.

FIG. 24A-FIG. 24F show schematic views of another breakaway mechanism of a fluid access device according to the present disclosure.

FIG. 28A-FIG. 28B show schematic views of another intraluminal valve of a fluid access device according to the present disclosure.

FIG. 30A-FIG. 30B show additional representative cross sections of fluid access lines of a fluid access device according to the present disclosure.

FIG. 33A-FIG. 33B show schematic section views of representative pathogen detection systems of a fluid access device according to the present disclosure.

DETAILED DESCRIPTION

The present disclosure provides fluid access devices for medical device applications, and methods for using the same. Although generally described in the context of a blood access device for hemodialysis applications to facilitate understanding, the disclosed devices are not limited to dialysis applications or blood access devices, and are useful in many other medical fluid access applications, for example apheresis, transfusions, continuous sensing of patient conditions, and other procedures.

As compared to known devices and methods, the fluid access devices of the present disclosure reduce infection risk and improve a patient's experience by automating best practices, reducing the number of human touchpoints necessary to fluidically connect a patient to a machine, and by integrating numerous functions in order to achieve rapid, sanitary, and repeatable fluidic connection.

Figure 1:
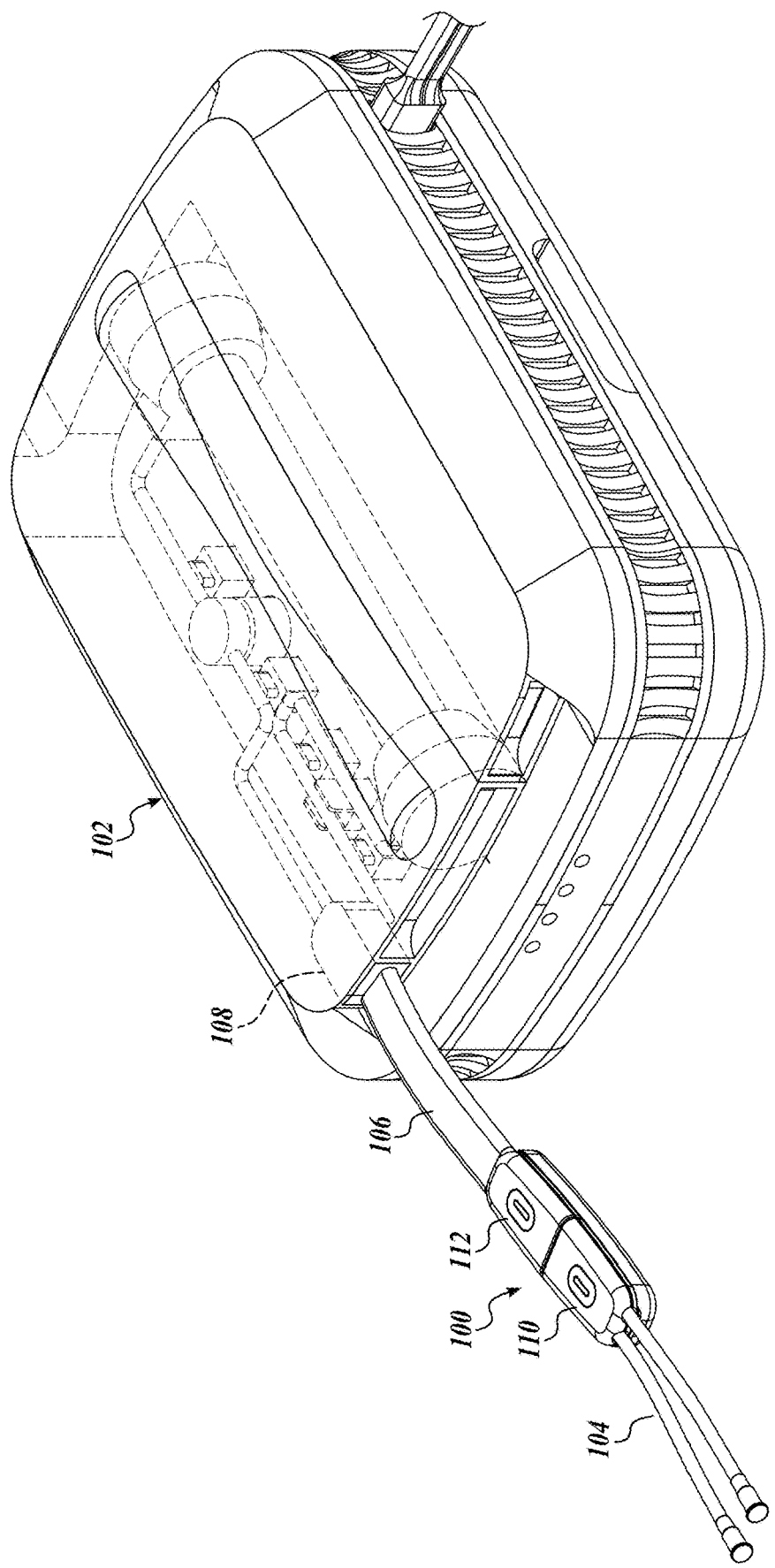
FIG. 1 shows a perspective view of a hemodialysis system connected with a fluid access device of the present disclosure.

FIG. 1 shows a fluid access device 100 according to an embodiment of the present disclosure, coupled with a hemodialysis system 102 configured to dialyze a patient's blood. The hemodialysis system 102 may be a single-pass dialysis system, a recirculation dialysis system, or other system design to remove urea and uremic toxins from a patient's bloodstream. Accordingly, the hemodialysis system 102 is fluidically coupled to a fluid access line 104 which both provides a patient's blood to a dialyzing unit of the hemodialysis system 102 and returns filtered (dialyzed) blood to the patient. In the illustrated embodiment, the patient-side fluid access line 104 and machine-side fluid access line 106 are multi-lumen catheters having at least two lumens. However, in some embodiments, the fluid access device 100 connects to a plurality of single-line fluid access lines. In the illustrated embodiment, the fluid access line 104 is fluidically coupled to the hemodialysis system 102 via an optional breakaway mechanism 108 that separates the fluid access line 104 from the hemodialysis system 102 upon experiencing at least a threshold tensile force. Representative breakaway mechanisms are described below with respect to FIG. 22A-FIG. 24B. In some embodiments, the fluid access line 104 includes one or more connectors disposed on a machine-side the fluid access device 100. Such connector(s) may be disposed in-line with the blood lumens of the fluid access line 104 or provided on an auxiliary fluid line, in order to enable fluidic connection with a third party tubeset.

In other embodiments, the breakaway mechanism 108 is disposed along the fluid access line(s), for example along the patient-side fluid access line 104 proximal to a catheter location entering the patient's body. In some embodiments, the breakaway device includes a frangible element that breaks a connection along the fluid access line, e.g., in response to a tensile force or crush force in excess of a certain threshold.

The fluid access device 100 is an assembly disposed in-line with the fluid access line 104, which operates to selectively connect and disconnect a patient side of the fluid access line 104 to a machine-side fluid access line 106. In particular, the fluid access device 100 establishes a selective and reversible fluidic connection between the patient-side fluid access line 104 and the machine-side fluid access line 106. Broadly speaking, the fluid access device 100 includes a patient-side hydraulic circuit 110 and a machine-side hydraulic circuit 112, which are described in detail below. In any of the embodiments described herein, the fluid access device may (but need not) include all or a portion of the fluid access line, e.g., a disposable segment thereof.

To afford a patient greater mobility and quality of life, the fluid access device 100 is configurable between a connected state and at least one disconnected state. In the connected state, a fluidic connection persists between the machine-side hydraulic circuit and the patient-side hydraulic circuit, such that fluid can flow freely between the patient-side fluid access line 104 and machine-side fluid access line 106. For example, during dialysis, undialyzed blood would flow from the patient-side hydraulic circuit to the machine-side hydraulic circuit (to a hemodialysis system), and dialyzed blood would flow from the machine-side hydraulic circuit to the patient-side hydraulic circuit. In the disconnected states, no fluidic connection exists between the machine-side hydraulic circuit and the patient-side hydraulic circuit. Potential disconnected states include at least a short-term disconnected state and a long-term disconnected state. A short-term disconnected state is suitable, for example, when a patient needs to quickly disconnect from the hemodialysis system 102 and plans on reconnecting to the hemodialysis system 102 within a relatively short timeframe, e.g., 1-2 hours. As described below, in the short-term disconnected state, fluid may be recirculated through a patient side of the fluid access device 100 to and from the patient; optionally, fluid is recirculated through a machine side of the fluid access device 100. Advantageously, recirculating the patient's blood through one or both of the hydraulic circuits reduces the risk of thrombosis and improves patient autonomy (by eliminating the need for a clinician to sterilize and lock the device). The short-term disconnect state is also advantageous as it does not require a complete 'rinseback' of the patient's blood within the machine tubing. Because blood rinseback is followed with saline, it adds fluid to the patient, contrary to the objective of dialysis.

A long-term disconnected state is suitable for when the patient needs to disconnect from the hemodialysis system 102 for an extended time period, e.g., between dialysis sessions. In the long-term disconnected state, the patient-side and the machine-side of the fluid access device 100 are sealed, and no fluid recirculates in the machine side (following rinse-back of the blood, e.g., using saline). In some embodiments, fluid recirculates in the patient-side in order to reduce thrombosis and fibroses. In some embodiments, a default, unpowered/error state for the fluid access device prevents fluid throughflow.

Figure 2A:
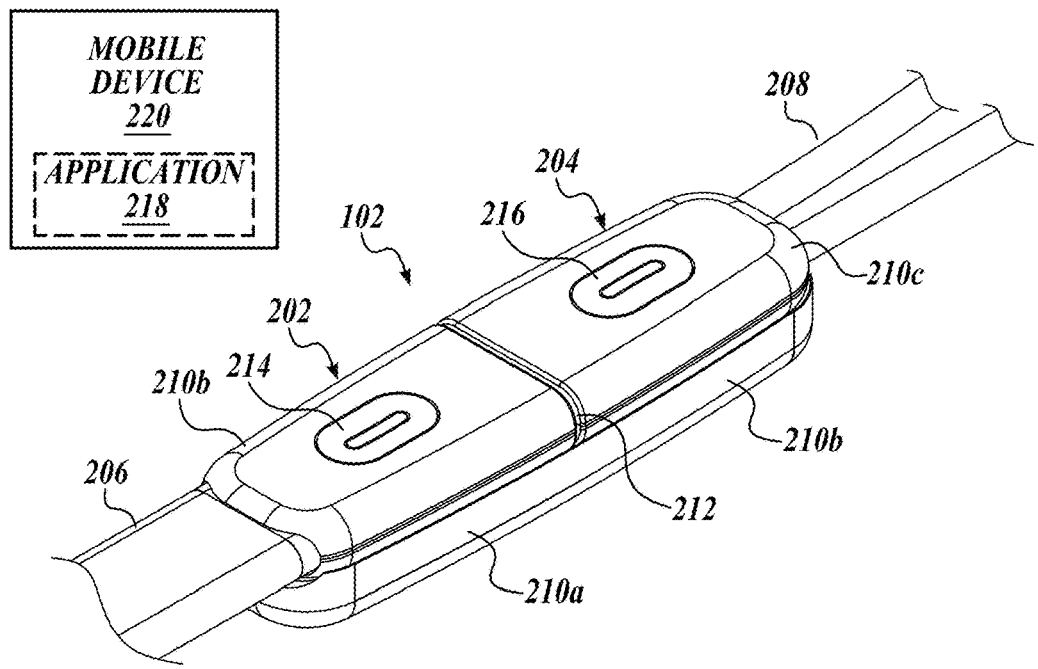
FIG. 2A shows a perspective view of a fluid access device of the present disclosure.
Figure 2B:
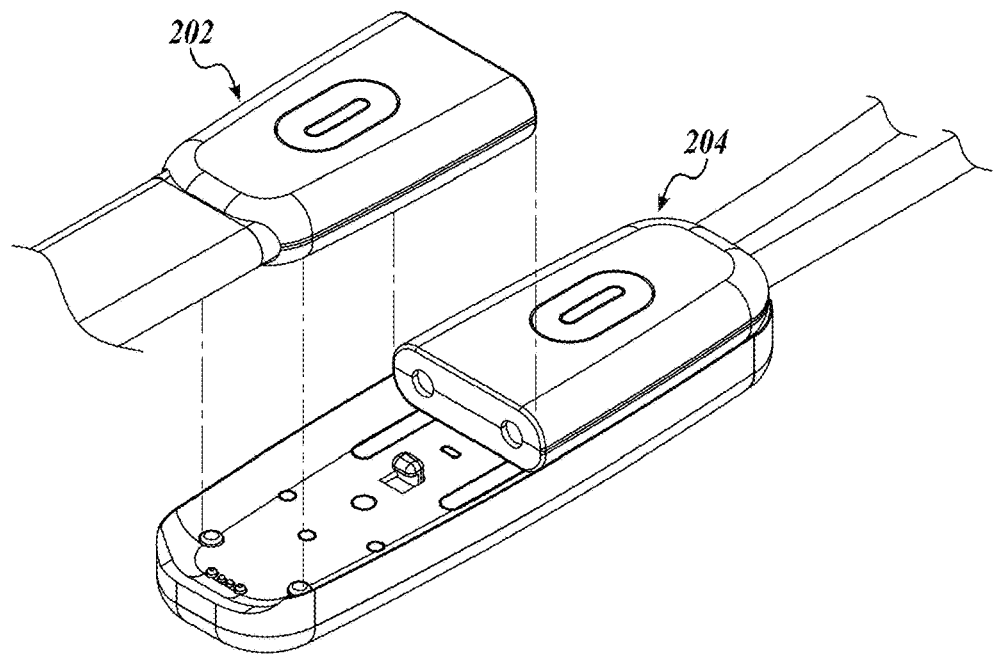
FIG. 2B shows a partially exploded perspective view of the fluid access device of FIG. 2B.

FIG. 2A-FIG. 2B show high-level perspective views of a fluid access device 200 of the present disclosure, which has the features of the fluid access device 100 of FIG. 1. In particular, fluid access device 200 includes a machine-side hydraulic circuit 202 and a patient-side hydraulic circuit 204, which are respectively connected to a machine-side fluid access line 206 and a patient-side fluid access line 208. The machine-side hydraulic circuit 202 and patient-side hydraulic circuit 204 are housed in a plurality of housings 210a-c, which are formed of a medical grade polymer (e.g., polypropylene) or other rigid and repeatedly sterilizable material. The machine-side fluid access line 206 includes an electrically conductive power cord integrated therein, which is configured to draw AC or DC power from the connected machine (e.g., hemodialysis system) to power the fluid access device 200.

Representative cross sections of the machine-side fluid access line 206 and patient-side fluid access line 208 are described below with respect to FIG. 29A-FIG. 30B. To facilitate use with multiple patients, in some embodiments, the machine-side hydraulic circuit 202 is at least partially disposable. In some embodiments, the machine-side fluid access line 206 also includes one or more communication lines to support data communications and/or power transmission between the machine- and patient-side hydraulic circuits 202, 204, as described below.

FIG. 2A shows the fluid access device 200 in a connected state, whereas FIG. 2B shows the fluid access device 200 in a disconnected state. As evident from comparing FIG. 2A to FIG. 2B, the machine-side hydraulic circuit 202 is reversibly connectable to the patient-side hydraulic circuit 204 at a fluidic interface 212. The machine-side hydraulic circuit 202 includes a first disconnect mechanism 214 (such as a button or latch) and/or the patient-side hydraulic circuit 204 includes a second disconnect mechanism 216, which operate to initiate a method of disconnecting the machine-side hydraulic circuit 202 from the patient-side hydraulic circuit 204 (described below). Therefore, according to certain methods of the present disclosure, a user initiates a disconnect sequence by depressing one or both of the disconnect mechanisms. In some embodiments, the disconnect mechanism(s) are presented on a user interface (e.g., a screen) disposed on the fluid access device 200, and/or a user interface disposed on a mobile device (e.g., a smartphone) programmed with an application that controls the fluid access device 200.

In some embodiments, the disconnect mechanisms 214, 216 include an indicator such as an LED and/or an audible chime. The indicator signals to the user one or more of the following states: when the fluid access device 200 is transitioning states (e.g., a flashing red light); when it is safe to disconnect the machine-side hydraulic circuit 202 from the patient-side hydraulic circuit 204 (e.g., a flashing green light); when fluid is passing through the fluid access device 200 (e.g., a solid green light); or an error condition (e.g., a solid red light, haptic feedback, and the like). These states and signals are representative, not limiting.

In some embodiments, an application 218 is provided with the fluid access device 200 in order to facilitate a user's ability to operate and understand the performance of the device 200, to communicate with a clinician and/or the device manufacturer. The application 218 includes a plurality of modules implemented as software logic (e.g., executable software code), firmware logic, hardware logic, or various combinations thereof, which are configured for storage on a data store of at least one of the fluid access device or mobile device 220 (e.g., a smartphone and/or a smartwatch, etc.) and configured for execution by a processor of the fluid access device 200 and/or mobile device 220.

In some embodiments, the application 218 includes a monitoring module that receives a signal from an onboard control circuit of the fluid access device 200 indicative of a status of the fluid access device 200 (e.g., connected, short-term disconnect, long-term disconnect, the system is dialyzing), and displays a message corresponding to the received signal. In some embodiments, the monitoring module enables two-way communication with the fluid access device 200. For example, the client inputs a command on an interface of the mobile device 220 (e.g., initiate disconnect sequence, initiate connection sequence, etc.), and the application 218 sends a signal to the fluid access device 200 based upon the input (e.g., execute disconnect sequence). In some embodiments, the application 218 includes a sensing module which senses one or more biometric parameters with the mobile device 220 (e.g., blood pressure), and then transmits a signal to the fluid access device 200 based upon the sensed parameter, which signal causes the fluid access device 200 to execute a sequence (e.g., initiate disconnect sequence). In some embodiments, the application 218 displays a dashboard of information relevant to the operation of the device 200, including for example the device state (connected/disconnected), one or more parameters sensed by the device (e.g., blood pressure, flow rate), and any relevant alerts (e.g., pathogen detection alert). In still other embodiments, the application 218 provides an interface to initiate communication with a clinician and/or device manufacturer. The foregoing functionalities are representative, not limiting.

Figure 3:
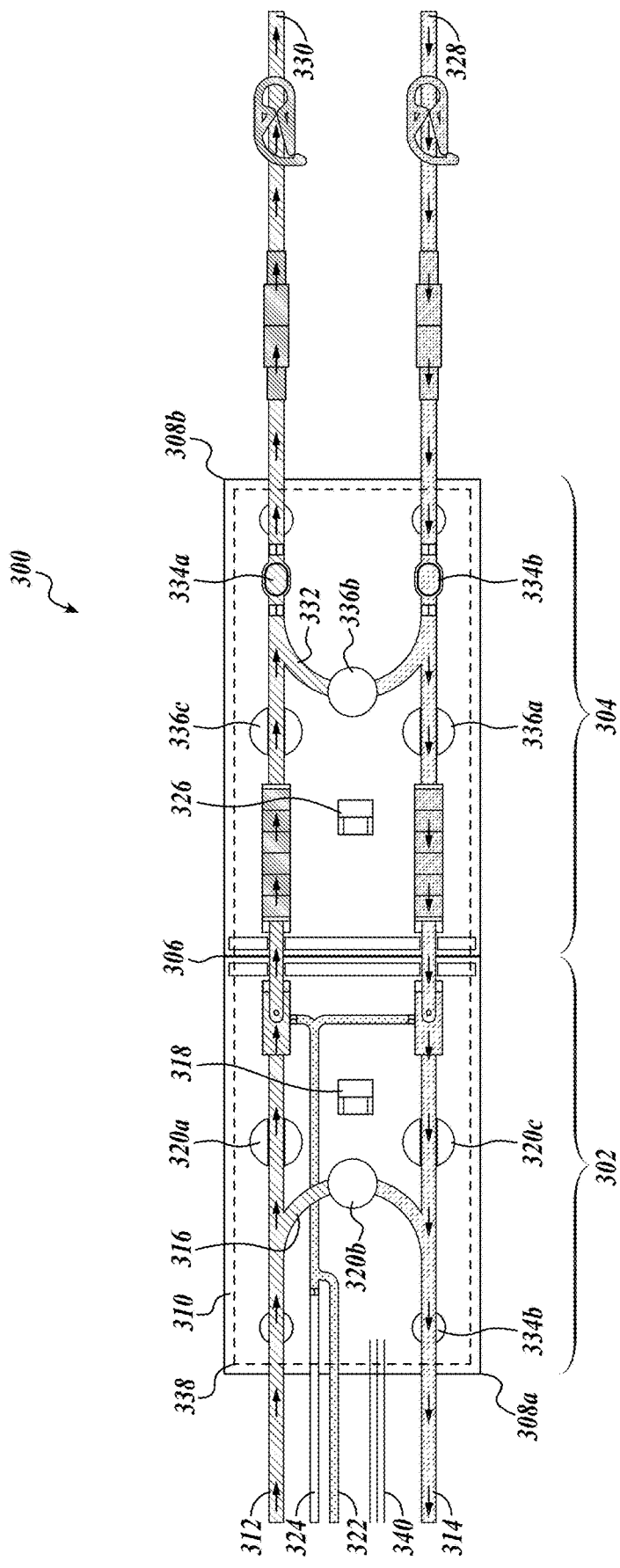
FIG. 3 shows a schematic top view of a portion of a fluid access device of the present disclosure.
Figure 4A:
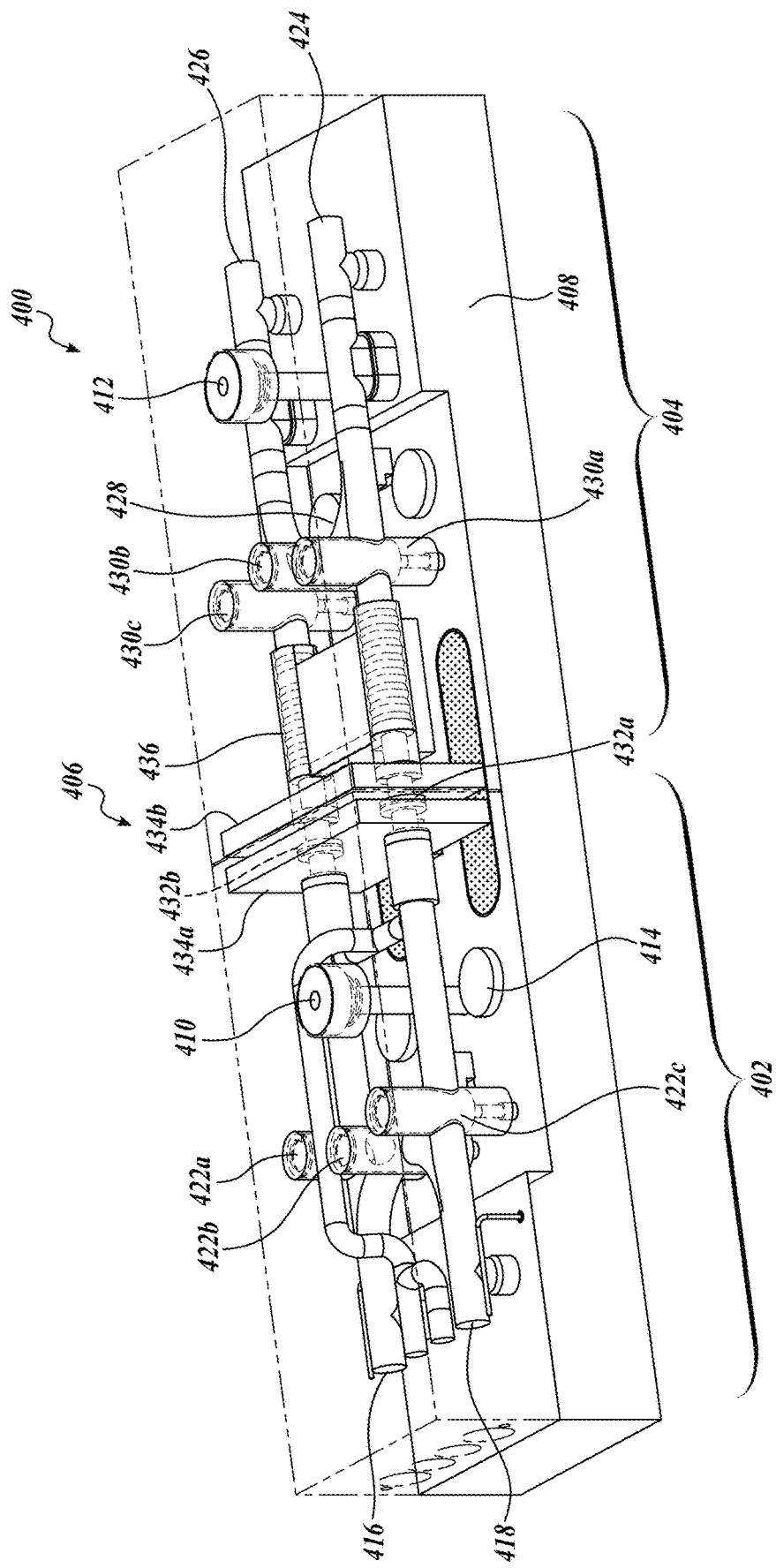
FIG. 4A shows a first perspective view of a fluid access device of the present disclosure.
Figure 4B:
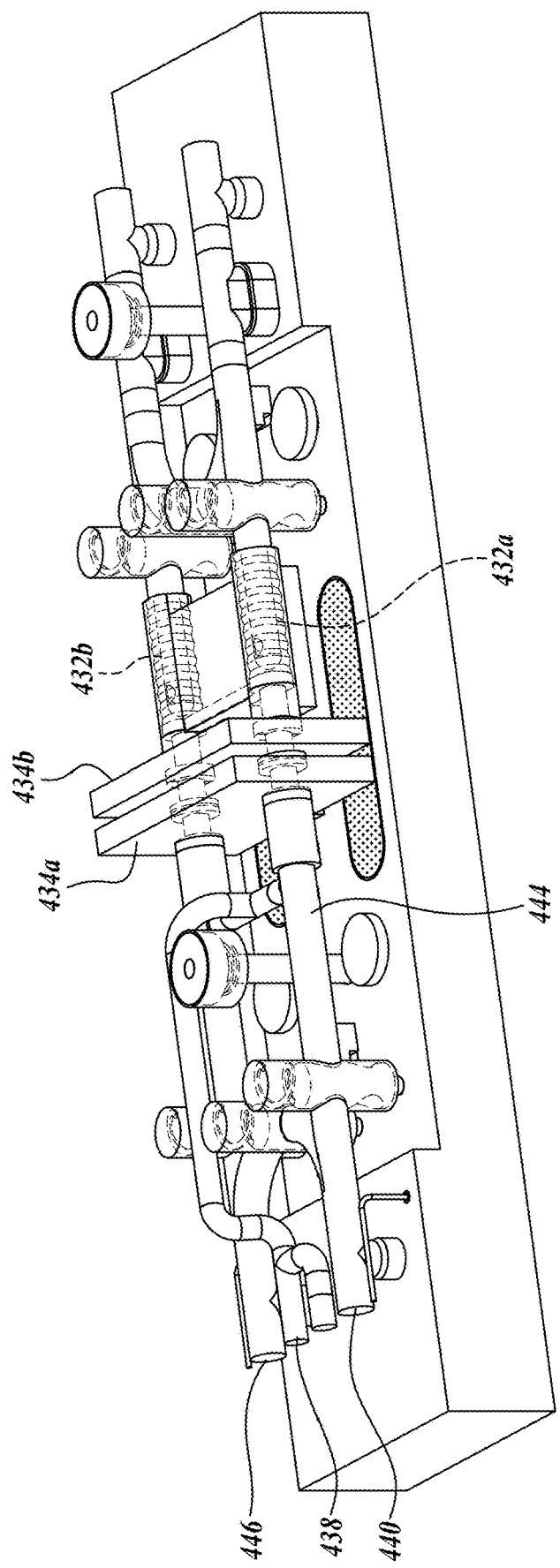
FIG. 4B shows a second perspective view of the fluid access device of FIG. 4A.
Figure 4C:
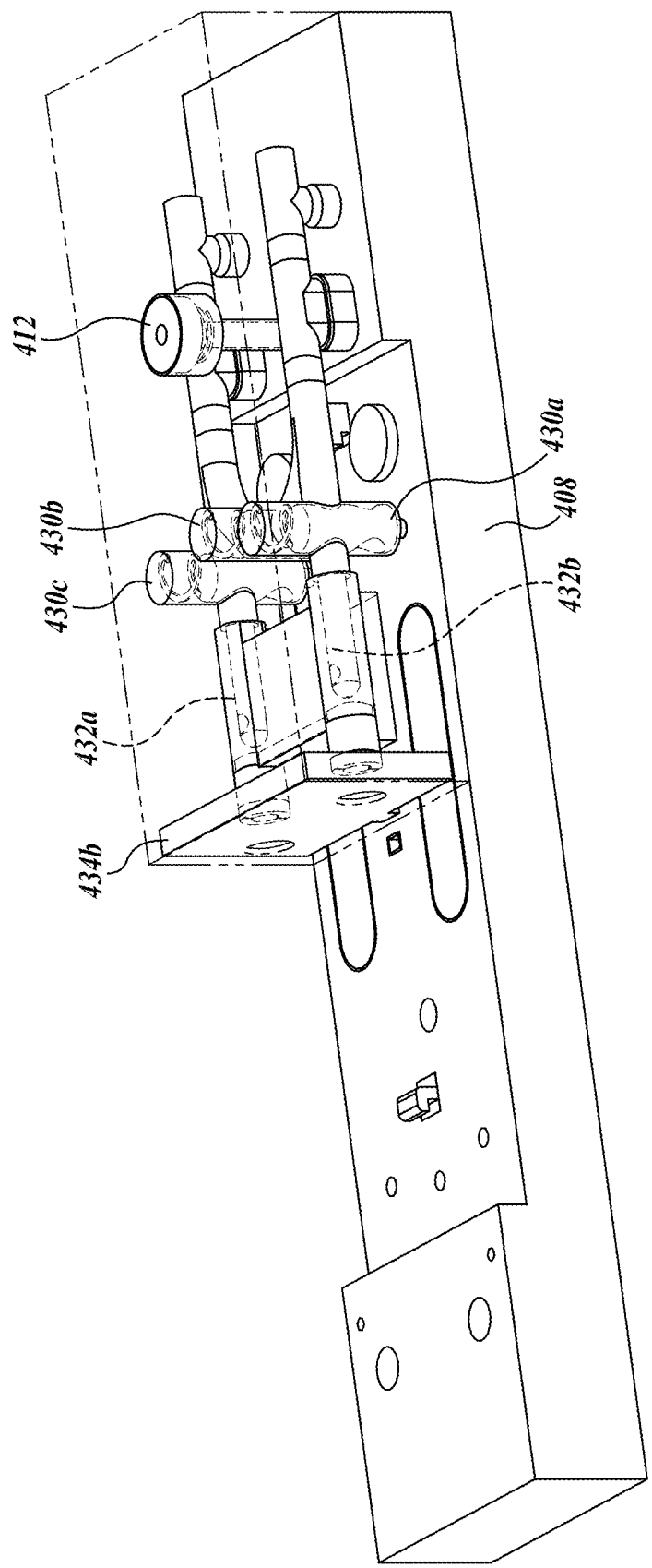
FIG. 4C shows a third, perspective view of the fluid access device of FIG. 4A in a disconnected state.
Figure 4D:
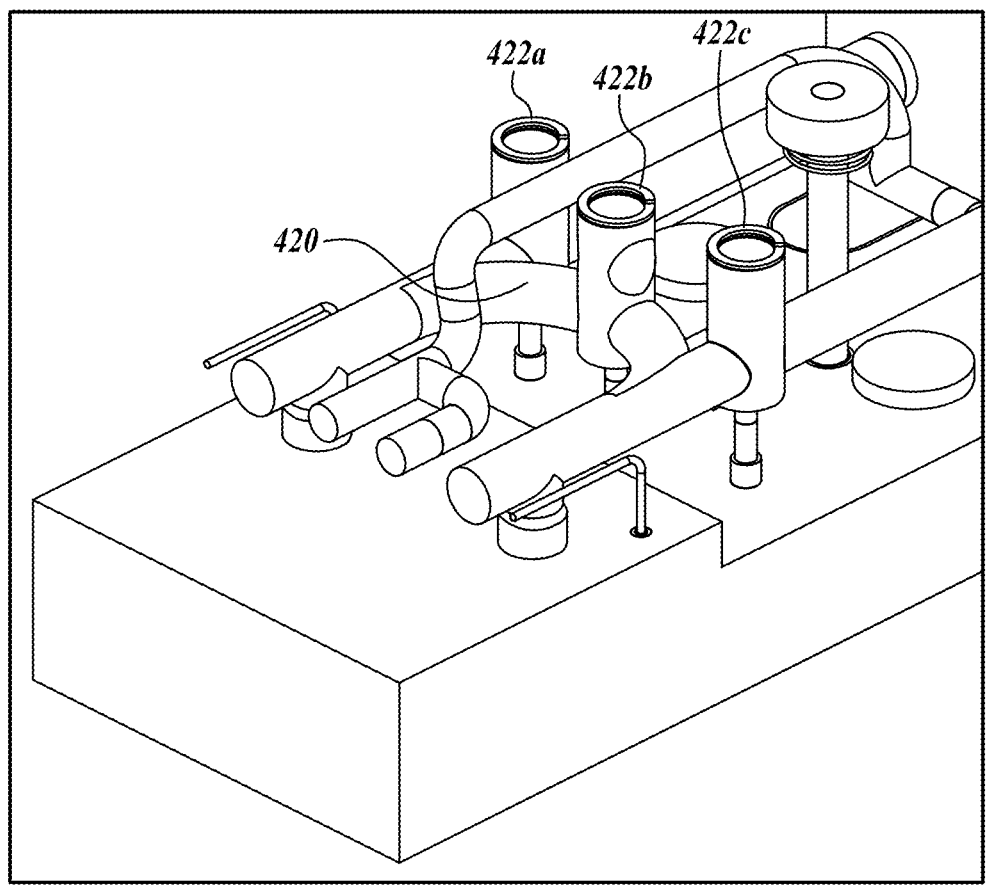
FIG. 4D shows a fourth perspective view of a portion the fluid access device of FIG. 4A.

FIG. 3 illustrates the components of a representative fluid access device 300. As described above, the fluid access device 300 generally includes a machine-side hydraulic circuit 302 and a patient-side hydraulic circuit 304, which selectively fluidically couple to each other at a fluidic interface 306, and which are respectively contained in protective housings 308a, b.

The machine-side hydraulic circuit 302 is disposed on an optional base 310 for secure connection to the patient-side hydraulic circuit 304, e.g., a rigid frame, platform, enclosure, or the like. The base 310 provides a stable common platform to which the hydraulic circuits are attached in the connected state, and which houses certain components such sensors, pumps, and locking mechanisms. However, some embodiments do not include a base, and in such embodiments, the hydraulic circuits contain all subsystems and directly couple and lock to each other in the connected state. A machine-side input lumen 312 and a machine-side output lumen 314 are fluidically parallel lumens configured to connect with the machine-side fluid access line described previously. In use, fluid enters and exits the machine-side hydraulic circuit 302 via the machine-side input lumen 312 and the machine-side output lumen 314, respectively. An optional machine-side recirculation lumen 316 bridges the machine-side input lumen 312 and the machine-side output lumen 314. The machine-side hydraulic circuit 302 is selectively securable to the base 310 via a lock 318 (e.g., an electromechanical, magnetic, or pneumatic locking latch or the like). In embodiments without a base, said lock(s) maybe disposed directly on the hydraulic circuits, allowing direct locking of the hydraulic circuits to each other. Although electromechanical locks, valves, and other features are generally described herein, the fluid access devices of the present disclosure are not limited to electromechanical features. In any embodiment, one or more discrete features (e.g., locks and valves) may be magnetic or pneumatic, i.e., operated under the motive force of a pressurized air source or vacuum source coupled with the fluid access device. For example, some embodiments include direct pneumatic devices (actuated by vacuum or positive pressure) which are configured to lock the hydraulic circuits together (either directly or via the base) and/or for advancing/retracting needles, cannulas, or other fluidic elements. Representative examples of such devices and means for providing air to the fluid access device are described below.

To enable selective control over the machine-side hydraulic circuit 302, a plurality of valves 320a-c are disposed in the machine-side hydraulic circuit 402. In particular: first valve 320a, second valve 320b, and third valve 320c are each configured to selectively open and close the machine-side input lumen 312 (downstream of the machine-side recirculation lumen 316), the machine-side recirculation lumen 316, and the machine-side output lumen 314 (upstream of the machine-side recirculation lumen 316), respectively. Representative and non-limiting valves include push/pull plunger valves actuated via electromechanical valve actuators (e.g., pins) disposed in the base 310, pinch/crush type valves, and any of the intraluminal valves as described below with respect to FIG. 25A-FIG. 28B. Any valve described herein may be an electromechanical valve, a pneumatic valve, a chemical valve, or other valve type. In some embodiments, one or more valves of the fluid access device are an intraluminal valve such as any type described herein, which advantageously reduces a size of the fluid access device and can prevent bleed out in case of damage to the extracorporeal portion of the catheter and/or fluid access device.

Machine-side hydraulic circuit 302 includes an optional solution hydraulic circuit (e.g., for a lock solution such as heparin, a saline solution, sodium citrate, or similar) which fluidically integrates with the machine-side input lumen 312 and machine-side output lumen 314. In any embodiment described herein, the solution hydraulic circuit may integrate via a manifold and one or more passive valves as described below with respect to FIG. 16. The solution hydraulic circuit includes, for example, a solution supply lumen 322 and a waste lumen 324, which may be configured to remove liquid and/or gas from the hydraulic circuit(s) and to direct said waste to a drain or a separate waste reservoir, as discussed below. Advantageously, the solution hydraulic circuit enables selective flushing, priming, and sterilizing of the machine-side hydraulic circuit 302 and the patient-side hydraulic circuit 304, e.g., prior to disconnecting the machine-side hydraulic circuit 302 from the patient-side hydraulic circuit 304. Some embodiments of the solution hydraulic circuit include a first circuit or fluid line for a lock solution (e.g., heparin and sodium citrate), a second circuit for a second solution, such as saline, and an optional third circuit for waste. These fluid lines may be fluidically parallel to one another, and in some embodiments may fluidically connect with a manifold disposed between the machine-side input lumen 312 and machine-side output lumen 314.

In any embodiment herein, a waste reservoir may be fluidically coupled to receive waste, including saline, lock solution, biological fluids, or other fluids. In some embodiments, the waste reservoir is integrated into a fluid access line coupled to the fluid access device (e.g., a disposable tubeset). In other embodiments, the waste reservoir is disposed within the hemodialysis system. In still other embodiments, the waste reservoir is disposed with a control unit between the fluid access device and the hemodialysis system, or is an external fluid provisioning module configured to provide and/or receive said fluid(s) to/from the fluid access device 300.

Similar to the machine-side hydraulic circuit 302, the patient-side hydraulic circuit 304 is selectively secured to the base 310 with a lock 326. A patient-side input lumen 328 and a patient-side output lumen 330 are fluidically parallel lumens configured to connect with the patient-side fluid access line described previously. In use, fluid enters and exits the patient-side hydraulic circuit 304 via the patient-side input lumen 328 and the patient-side output lumen 330, respectively. A patient-side recirculation lumen 332 bridges the patient-side input lumen 328 and the patient-side output lumen 330.

A plurality of pumps move fluid (e.g., blood) between the hemodialysis system and the patient. In the representative embodiment shown, a first pump 334a is disposed in-line with the patient-side output lumen 330, and a second 334b is disposed in-line with the patient-side input lumen 328. Both pumps 334a-b are powered by the on-board control circuit, described below. Although disposed in the patient-side hydraulic circuit 304 in FIG. 3, in other embodiments, one or more of the pumps are disposed in the machine-side hydraulic circuit 302.

Patient-side hydraulic circuit 304 includes a plurality of valves 336a-c. In particular: first valve 336a, second valve 336b, and third valve 336c are each configured to selectively open and close the patient-side input lumen 328 (downstream of the patient-side recirculation lumen 332), the patient-side recirculation lumen 332, and the patient-side output lumen 330 (upstream of the patient-side recirculation lumen 332), respectively. As described above, representative valves include electromechanical and pneumatic valves, including the intraluminal valves described below. The patient-side hydraulic circuit 304 is selectively securable to the base 310 via a lock 326.

The valves (and other elements) described herein are actuated by a control circuit 338 disposed in the fluid access device 300 (e.g., in the base 310). A data/power interface 340 (e.g., a USB interface or the like) in electrical communication with control circuit 338 is configured to draw power and/or data from a hemodialysis system, and to provide said power and data to elements of the fluid access device 300.

Control circuit 338 is operatively connected (e.g., electrically connected) to a power supply provided by the connected hemodialysis system via data/power interface 340, and/or optionally by a power source (e.g., a battery) disposed on the fluid access device 300. Control circuit 338 includes a processor (e.g., a general processing unit, graphical processing unit, or application specific integrated circuit), a data store (a tangible machine-readable storage medium), a plurality of modules implemented as software logic (e.g., executable software code), firmware logic, hardware logic, or various combinations thereof. In some embodiments, control circuit 338 includes a transceiver that transmits signals from any of the modules discussed below to the mobile device and the connected machine (hemodialysis system), and receives signals transmitted from the mobile device. The data store of control circuit 338 is a tangible machine-readable storage medium that includes a mechanism that stores information in a non-transitory form accessible by a machine (e.g., the processor of control circuit 338). For example, a machine-readable storage medium includes recordable/non-recordable media (e.g., read only memory (ROM), random access memory (RAM), magnetic disk storage media, optical storage media, flash memory devices, etc.).

In some embodiments, control circuit 338 includes a communications interface having circuits configured to enable communication with the hemodialysis system, a mobile device (e.g., a smartphone), and/or other network element via the internet, cellular network, RF network, Personal Area Network (PAN), Local Area Network, Wide Area Network, or other network. In any embodiments, the control circuit 338 may include communication means enabling communication between the machine-side hydraulic circuit 302 and the patient-side hydraulic circuit 304, e.g., such that the machine-side hydraulic circuit 302 receives electronic data from the patient-side hydraulic circuit 304, and vice versa. Accordingly, the communications interface may be configured to communicate using wireless protocols (e.g., WIFI®, WIMAX®, BLUETOOTH®, ZIGBEE®, Cellular, Infrared, Nearfield, etc.) and/or wired protocols (Universal Serial Bus or other serial communications such as RS-216, RJ-45, etc., parallel communications bus, etc.). In some embodiments, the communications interface includes circuitry configured to initiate a discovery protocol that allows control circuit 338 and other network element to identify each other and exchange control information. In an embodiment, the communications interface has circuitry configured to a discovery protocol and to negotiate one or more pre-shared keys.

Any fluid access device and/or fluid access line of the present disclosure may be provided with one or more optional access sites to enable administration of medication and/or sampling of fluids. In some embodiments, such access site is a septum, valve, or port, which may be disposed through a wall of any of the machine-side input lumen 312, machine-side output lumen 314, machine-side recirculation lumen 316, patient-side input lumen 328, patient-side output lumen 330, or patient side recirculation lumen 332.

FIG. 4A-FIG. 4D illustrate a representative fluid access device 400, which includes the features of fluid access device 300 of FIG. 3. Accordingly, the fluid access device 400 includes a machine-side hydraulic circuit 402 and a patient-side hydraulic circuit 404, which are selectively fluidically couplable at a fluidic interface 406.

The machine-side hydraulic circuit 402 and patient-side hydraulic circuit 404 are disposed on an optional base 408 for secure connection to the patient-side hydraulic circuit 404, e.g., a rigid frame, platform, or the like. To enable disengagement from the base 408, machine-side hydraulic circuit 402 includes a second disconnect mechanism 410 (e.g., a button or latch). Similarly, patient-side hydraulic circuit 404 includes a first disconnect mechanism 412. Optionally, one or both of the machine-side hydraulic circuit 402 and patient-side hydraulic circuit 404 are selectively secured to the base 408 by one or more magnets 414, latches, or the like, which help guide a user to correctly couple the hydraulic circuits.

A machine-side input lumen 416 and a machine-side output lumen 418 are fluidically parallel lumens configured to connect with the machine-side fluid access line described previously. In use, fluid enters and exits the machine-side hydraulic circuit 402 via the machine-side input lumen 416 and the machine-side output lumen 418, respectively. A machine-side recirculation lumen 420 bridges the machine-side input lumen 416 and the machine-side output lumen 418 (see FIG. 4D).

To enable selective control over the machine-side hydraulic circuit 402, a plurality of valves 422a-c are disposed in the machine-side hydraulic circuit 402. In particular: first valve 422a, second valve 422b, and third valve 422c are each configured to selectively open and close the machine-side input lumen 416 (downstream of the machine-side recirculation lumen 420), the machine-side recirculation lumen 420, and the machine-side output lumen 418 (upstream of the machine-side recirculation lumen 420), respectively. Representative and non-limiting valves include push/pull plunger valves actuated via electromechanical or pneumatic valve actuators (e.g., pins) disposed in the base 310, and any of the intraluminal valves as described below with respect to FIG. 25A-FIG. 28B. Each of the valves disclosed herein may be biased toward a closed state (e.g., by a spring or other biasing mechanism), and/or by a valve actuator thereof, such that when the fluid access device 400 is unpowered, the valves close and prevent fluid flow.

Patient-side hydraulic circuit 404 includes a patient-side input lumen 424, a patient-side output lumen 426, and a patient-side recirculation lumen 428 bridging the two lumens. A first valve 430a, second valve 430b, and third valve 430c are each configured to selectively open and close the patient-side input lumen 424 (downstream of a patient-side recirculation lumen), and the patient-side output lumen 426 (upstream of the patient-side recirculation lumen), respectively.

The fluidic interface 406 includes a plurality of retractable cannulas 432a-b (or retractable needles, septa and receivers, or the like as described below with respect to FIG. 13A-FIG. 17), which extend and retract in response to signals received from the control circuit (e.g., a connect/disconnect signal). Cannula 432a selectively couples machine-side output lumen 418 to patient-side input lumen 424, and cannula 432b selectively couples machine-side input lumen 416 to patient-side output lumen 426. After or substantially simultaneously with the retraction of the cannulas 432a-b, closure mechanisms such as shutters 434a-b automatically close off the fluidic pathways (i.e., the distal ends of the fluidic pathways at the fluidic interface 406) to prevent contamination and/or to waterproof the device. In any embodiment, the closure mechanisms may be considered part of the fluidic interface. In some embodiments, the shutters 434a-b are actuated by one or more actuators based upon receipt of connect/disconnect signal from the control circuit. In some embodiments, the shutters 434a-b are biased toward a closed position (i.e., a position that close off the fluid passageway), such as with one or more biasing mechanisms such as a spring.

Figure 5A:
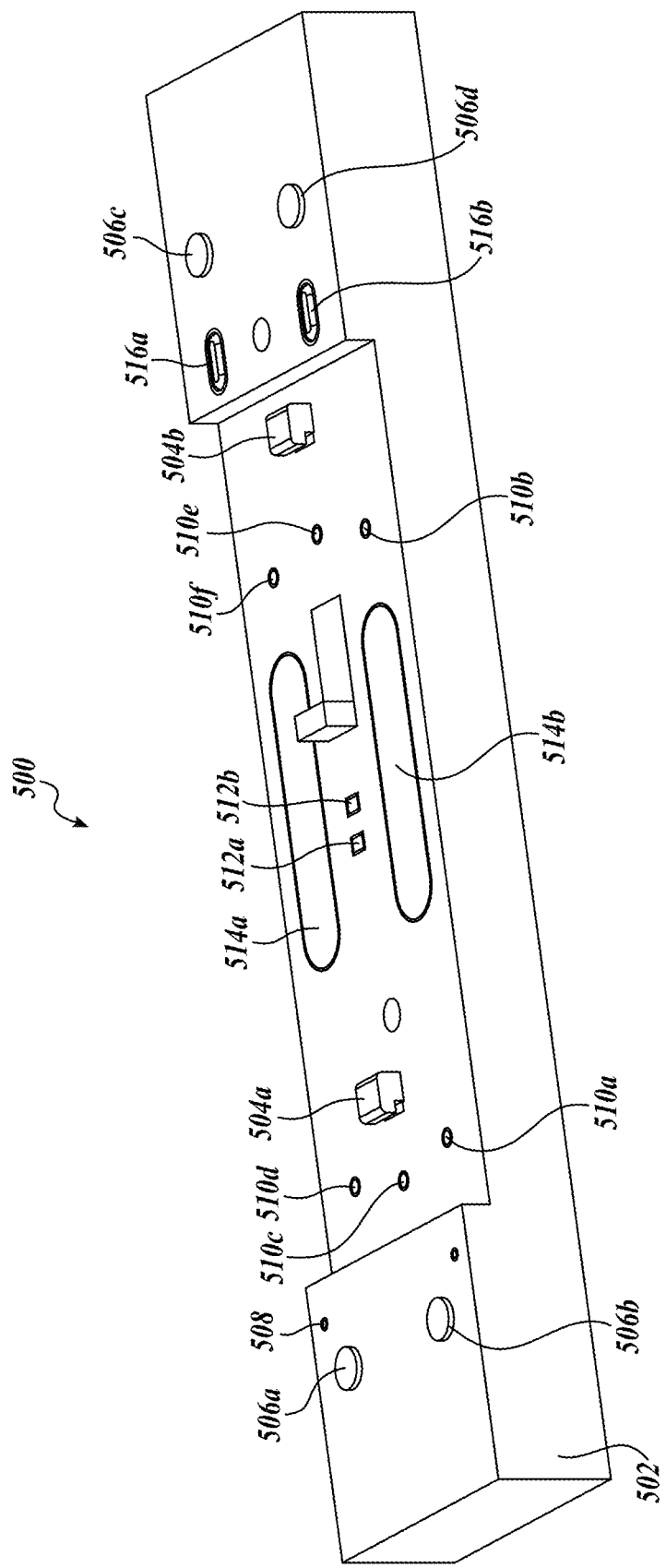
FIG. 5A shows a perspective view of a base for a fluid access device according to the present disclosure, in a first state.
Figure 5B:
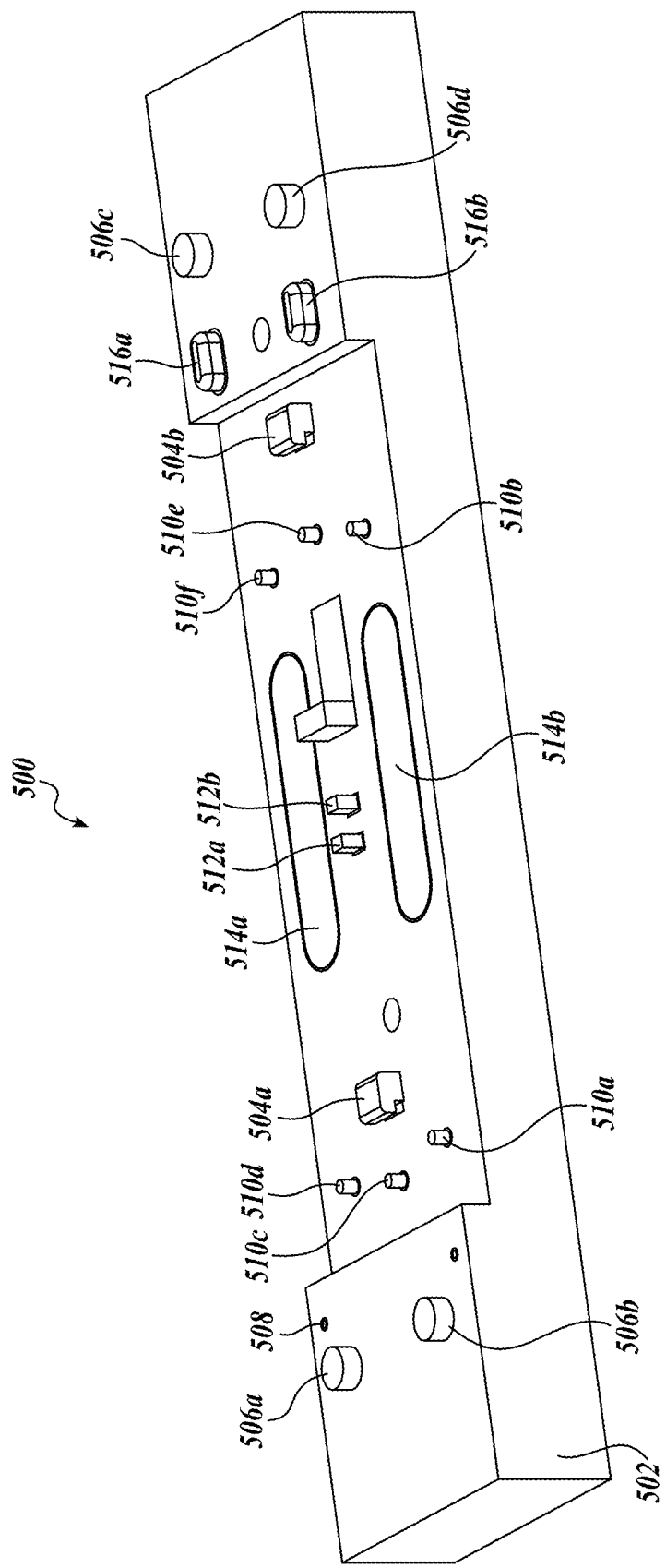
FIG. 5B shows a perspective view of the base for a fluid access device of FIG. 5A, in a second state.

FIG. 5A-FIG. 5B show one representative base 500, which is adapted for use with any of the fluid access devices described herein. As described previously, some fluid access devices of the present disclosure do not include a separate base. For example, in some embodiments, a base structure is formed integrally with one of the machine-side or patient-side hydraulic circuits. FIG. 5A shows the base 500 in a first state with a number of the elements retracted, whereas FIG. 5B shows base 500 in a second state with a number of the elements extended. Base 500 includes a housing 502 formed in one or more parts of a polymer (e.g., polypropylene) a metal (e.g., aluminum), or similar rigid material, which protects and stabilizes internal components.

One or more retention mechanisms 504a, b (e.g., latches, magnets, or the like) selectively couple the machine-side and patient-side hydraulic circuit to the base 500. In some embodiments, retention mechanisms include magnets disposed in the housing 502 and in the hydraulic circuits. Advantageously, the retention mechanisms stabilize the fluidic connection between the hydraulic circuits and prevents unintentional disconnection between the hydraulic circuits.

One or more sensors 506a disposed on the housing 502 and communicatively coupled with the control circuit detect the presence (or absence) of the hydraulic circuits. Accordingly, the sensor 506a provides a connect/disconnect signal to the control circuit. Based upon the connect/disconnect signal, the control circuit determines whether the fluid access device is in the connected state or a disconnected state.

In some embodiments, the base 500 includes additional sensors such as the following:

Sensors (optical, ultrasonic) that monitor the blood channel continuously for heart rate, temperature, hemoglobin and other blood properties, uremic toxins (such as urea, uric acid)

Sensors to monitor the blood pressure, either directly or in connection with biometric data from a mobile device communicatively coupled to the base 500

Sensors to monitor the presence of air

Sensors to detect a leak in the system

Any or all of the foregoing sensed parameters mays be transmitted to the machine (e.g., a hemodialysis system) and/or a mobile device to help inform the patient and clinician on treatment progress, and/or to make the system safe if an out of range or abnormal condition is detected.

In some embodiments, the control circuit actuates one or more valves, shutters, pumps, locks, sanitization module, or other feature based upon the connect/disconnect signal. Suitable sensors 506*a* include optical sensors, capacitive or resistive touch sensors, pressure switches, and the like.

A data/power interface 508 is an interface between the machine-side hydraulic circuit (which houses the data/power interface between the fluid access device and the connected hemodialysis system) and the control circuit disposed in the base 500. That is, the data/power interface 508 transfers power and data from the machine-side hydraulic circuit to the base 500 and the patient-side hydraulic circuit.

A plurality of valve actuators 510*a-f* is electrically connected to the control circuit and selectively cycle the valves of the hydraulic circuits between open and closed states. In the illustrated embodiment, the valve actuators 510*a-f* are pin-based actuators that retract (as shown in FIG. 5A) and extend (as shown in FIG. 5B) in order to cycle the valves of the hydraulic circuits between open and closed states. Accordingly, a first plurality of valve actuators 510*a-c* is disposed on a machine-side of the base 500, and a second plurality of valve actuators 510*b-f* is disposed on a patient-side of the base 500.

Similar to the valve actuators 510*a*, a plurality of closure mechanism actuators 512*a* urge the closure mechanisms (e.g., shutters) towards open and/or closed positions. In the illustrated embodiment, the closure mechanism actuators 512*a* are pin-based actuators that retract (as shown in FIG. 5A) and extend (as shown in FIG. 5B) in order to cycle the shutters of the hydraulic circuits. The closure mechanism actuators may be electromechanical or pneumatic, for example.

Base 500 includes a sanitization module 514*a* which operates to sterilize the hydraulic circuits of the fluid access device, for example prior to disconnection and/or reconnection of the machine-side hydraulic circuit to the patient-side hydraulic circuit. In the illustrated embodiment, the sanitization module 514*a* includes a plurality of ultraviolet LEDs positioned to irradiate the fluidic interface and hydraulic circuits with ultraviolet light in order to sterilize the same. In some embodiments, such as fluid access devices without a separate base, the sanitization module is embedded in one or both of the machine-side hydraulic circuit or the patient-side hydraulic circuit.

Pump plungers 516*a, b* oscillate up and down against an elastomeric membrane on the patient-side input lumen and patient-side output lumen in order to pump fluid therethrough. In some embodiments, pump plungers are disposed on the machine-side as well as, or alternatively to, the patient-patient side. Other suitable pumps include linear peristaltic pumps and impeller pumps that drive impellers in the lumens via electromagnetic coupling.

Figure 6A:
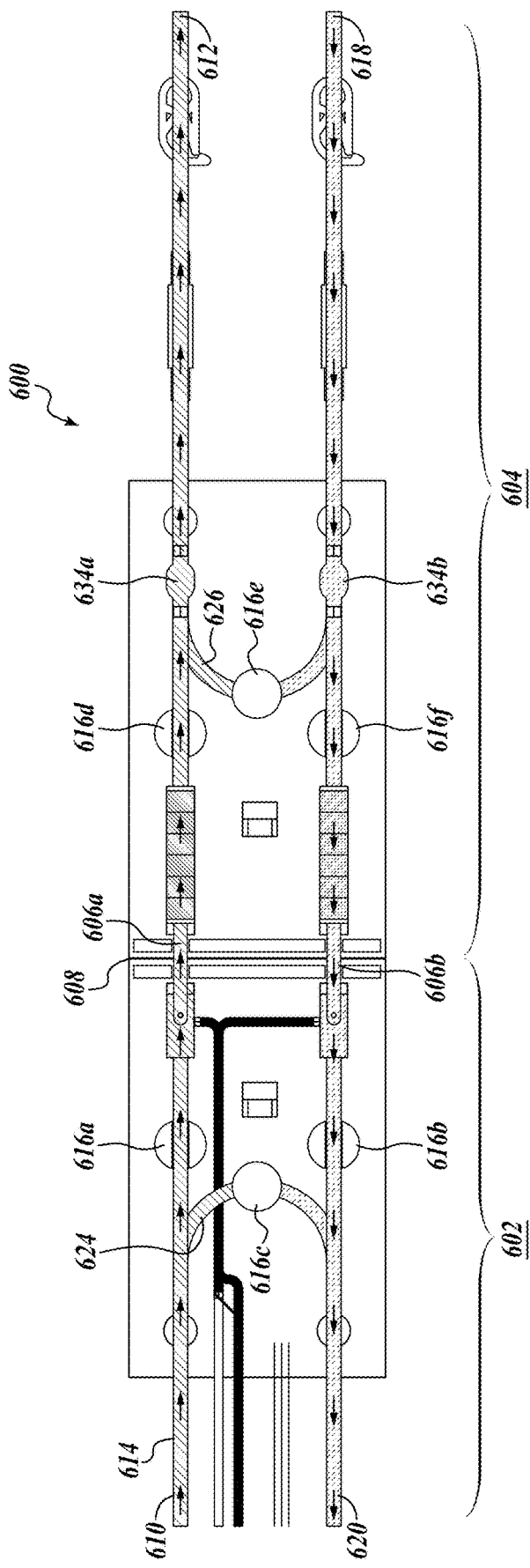
FIG. 6A shows a schematic top view of a portion of a fluid access device of the present disclosure, in a connected state.

FIG. 6A-FIG. 6C show a representative fluid access device 600 in three different operational states: a connected state (FIG. 6A), a short-term disconnected state (FIG. 6B), and a long-term disconnected state (FIG. 6C). Fluid access device 600 includes all of the features of the fluid access device 300 of FIG. 3. Accordingly, alike terms used with respect to FIG. 6A-C below refer to alike features described above with respect to FIG. 3. However, the operational states described below are not limited to the fluid access device 600. Rather the operational states are representative of fluid flow configurations that any fluid access device of the present disclosure may be configured to achieve.

In the connected state shown in FIG. 6A, the machine-side hydraulic circuit 602 abuts the patient-side hydraulic circuit 604 at fluidic interface 608, the machine-side hydraulic circuit 602 is fluidically connected to the patient-side hydraulic circuit 604 by retractable cannulas 606*a, b* at fluidic interface 608, such that two parallel and fluidically separate fluid pathways are formed. The first fluidic pathway includes the machine-side input lumen 610 and the patient-side output lumen 612, and provides fluid 614 (e.g., dialyzed blood) from the hemodialysis system to the patient. Accordingly, valves 616*a, b* are set to an open position by the control circuit.

The second fluidic pathway includes the patient-side input lumen 618 and the machine-side output lumen 620, and provides fluid 622 (e.g., patient's blood) to the hemodialysis system. In order for fluid to pass from the patient to the machine, valves 616*b, f* are set to an open position by the control circuit.

To maintain fluidic separation between the parallel fluidic pathways, valves 616*c, d* are set to a closed position by the control circuit such that neither of the machine-side recirculation lumen 624 nor the patient-side recirculation lumen 626 bridge the parallel fluidic pathways.

The valve configuration shown in FIG. 6A is a connected state valve configuration. In some embodiments, the valves are actuated into the connected state valve configuration based upon a connect/disconnect signal received from a sensor (as shown in FIG. 5A) and/or from one or more disconnect mechanisms.

FIG. 6B shows the fluid access device 600 in a short-term disconnected state, e.g., which is suitable for when a patient disconnects from the hemodialysis system for a relatively short time period, e.g., 1-2 hours. Nevertheless, it shall be appreciated that the following disconnected state is not limited to applications in which the disconnect time period is less than two hours.

As shown, the machine-side hydraulic circuit 602 is fluidically disconnected and physically separated from the patient-side hydraulic circuit 604. Such disconnection sequence may include a substantially simultaneous retraction of the closure mechanism and the machine-side and patient-side lumens. Additionally, fluid is recirculated through at least one of the machine-side hydraulic circuit 602 or patient-side hydraulic circuit 604. In particular, blood is recirculated on the machine side through the hemodialysis system and through the machine-side hydraulic circuit 602. On the patient-side, the patient's blood is drawn through the patient-side hydraulic circuit 604 and then pumped back to the patient, in order to prevent thrombosis. Advantageously, this configuration enables the hemodialysis system to continue operating without interruption and enables the patient to quickly resume treatment after re-connection to the hemodialysis system.

To enable disconnection, each of the machine-side hydraulic circuit 602 and patient-side hydraulic circuit 604 may be provided (e.g., flooded, filled, or flushed) with a lock solution via solution hydraulic circuit 628. Then, cannulas 606a, b are retracted, thereby fluidically disconnecting the two hydraulic circuits. To prevent contamination of the cannulas and to waterproof the device, closure mechanisms (e.g., shutters) 630a, b close over the respective cannulas, for example simultaneously with retraction of the cannulas. And, to enable physical separation of the machine-side hydraulic circuit 602, a retention mechanism 632 disengages from the housing of the machine-side hydraulic circuit 602. In some embodiments, the retracted cannulas retain a volume of lock solution after retraction/disconnection.

To enable recirculation in the machine-side hydraulic circuit 602, valves 616a, e are set to a closed position and valve 616c is set to an open position by the control circuit (e.g., prior to disconnection of the machine-side hydraulic circuit 602 from the base). This allows fluid to recirculate from the machine-side input lumen 610 to the machine-side output lumen 620 via the machine-side recirculation lumen 624 under motive force provided by hemodialysis system pumps.

To enable recirculation on the patient-side hydraulic circuit 604, valves 616d, f are set to a closed position and valve 616e is set to an open position by the control circuit. Additionally, one or more of pump interfaces 634a, b are turned on. This allows fluid to recirculate from the patient-side input lumen 618 to the patient-side output lumen 612 via the patient-side recirculation lumen 626 under the motive force of pump interfaces 634a, b.

The valve configuration shown in FIG. 6B is a disconnected state valve configuration. In some embodiments, the valves are actuated into the disconnected state valve configuration based upon a connect/disconnect signal received from the control circuit, based upon a connect/disconnect signal received from a sensor (as shown in FIG. 5A) and/or from one or more disconnect mechanisms.

FIG. 6C shows the fluid access device 600 in a long-term disconnected state, e.g., which is suitable for when a patient disconnects from the hemodialysis system for a relatively long time period, for example in between dialysis treatments. Nevertheless, it shall be appreciated that the following disconnected state is not limited to applications in which the disconnect time period is relatively long, however.

The long-term disconnected state of FIG. 6C is the same as the short-term disconnected state of FIG. 6B except as follows. First, fluid is not recirculated through the machine-side hydraulic circuit 602; rather, the machine-side hydraulic circuit 602 is rinsed back (i.e., blood is returned to the patient) and optionally sterilized, such as with an acidic formulation, hot water, ozone, ultraviolet light, sodium citrate, or saline provided by the solution hydraulic circuit 628, through a port or valve through a sidewall of one or more of the fluid pathways, and/or with the sanitization module disposed on the base. Secondly, in some embodiments, the patient's fluid (e.g., blood) is not recirculated through the patient-side hydraulic circuit 604. Accordingly, the pump interfaces 634a, b are turned off by the control circuit, the patient's fluid is evacuated from the patient-side hydraulic circuit 604 by providing the patient-side hydraulic circuit 604 with the sterile lock solution via the solution hydraulic circuit 628 (before disconnection), and the patient-side output lumen 612 and patient-side input lumen 618 are closed off with line locks or similar devices. However, in some embodiments, the patient's fluid is recirculated through the patient-side hydraulic circuit 604. In such embodiments, the pump interfaces 634a, b are turned off by the control circuit, but the patient's fluid is circulated through the patient-side hydraulic circuit 604 by one or more pumps (e.g., pump plungers such as 516a, b shown in FIGS. 5A-5B, peristaltic pumps, or similar). The pump plungers 516a, b are representative of suitable positive displacement pumps, including but not limited to membranes and diaphragm pumps. Alternative embodiments may include alternative positive displacement pumps.

The long-term disconnected state shown in FIG. 6C is a default state in some embodiments, in order to prevent fluid flow when the patient-side hydraulic circuit is separated from the machine-side hydraulic circuit.

FIG. 7A-FIG. 7H illustrate one representative method of uncoupling a machine-side hydraulic circuit of a fluid access device 700 from a patient-side hydraulic circuit of the same. The fluid access device 700 includes all the features of the previously-described fluid access devices, and previously-introduced terms used below shall have the same meaning as described above.

In particular, the illustrated method shows one representative method to transition the fluid access device 700 from a connected state to a short-term disconnected state.

Figure 7A:
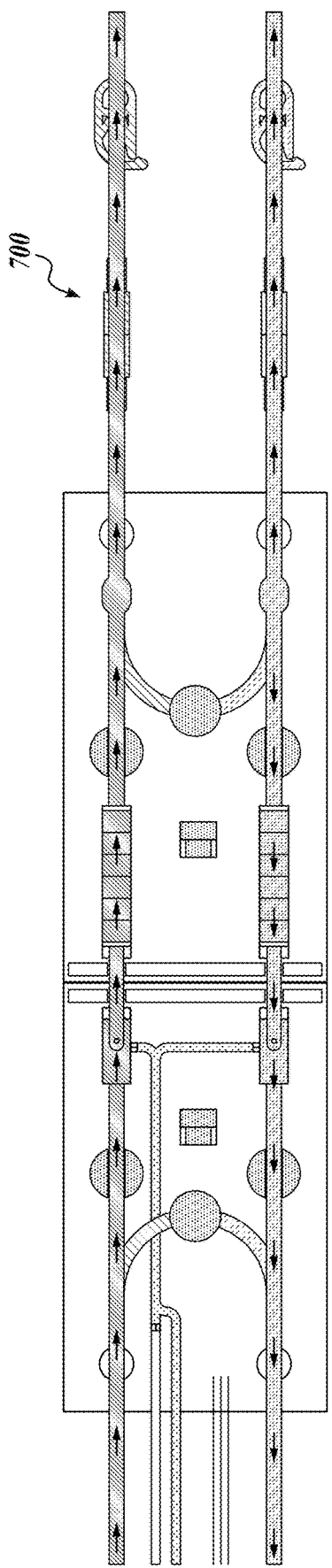

In an optional first step shown in FIG. 7A, a user initiates disconnection of the machine-side hydraulic circuit from the patient-side hydraulic circuit, such as by depressing one or more disconnect mechanisms disposed on a housing of the machine-side hydraulic circuit and/or the patient-side hydraulic circuit. In some embodiments, the user depresses the disconnect mechanism(s) in different sequences to initiate transition to a short-term disconnected state, as compared to a long-term disconnected state. Depression of the disconnect mechanism(s) sends a connect/disconnect signal to the control circuit.

Figure 7B:
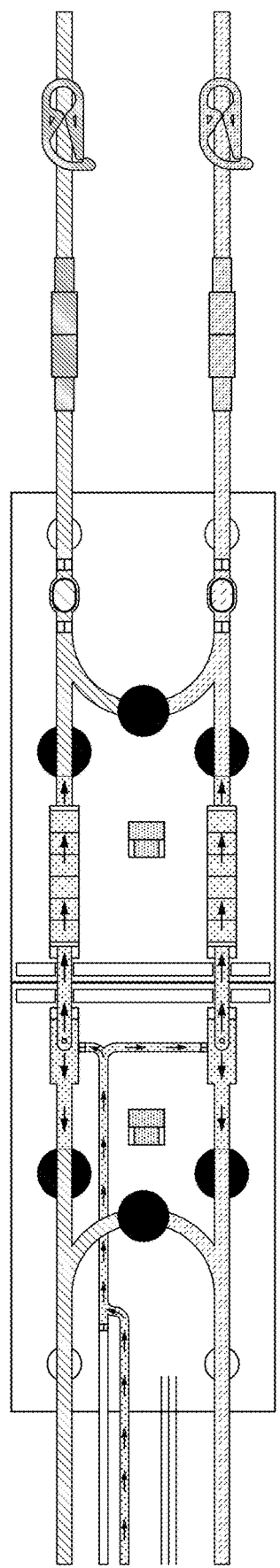

In a second step shown in FIG. 7B, a solution hydraulic circuit of the fluid access device 700 provides a sterile lock solution to the machine-side hydraulic circuit and patient-side hydraulic circuit (which are fluidically connected via the retractable cannulas). In an embodiment, the solution hydraulic circuit flushes the fluidic interface between the machine-side hydraulic circuit and the patient-side hydraulic circuit, as well as portions of the machine-side hydraulic circuit and the patient-side hydraulic circuit.

In a third step shown in FIG. 7C, valves disposed in-line with the machine-side input lumen, machine-side output lumen, patient-side input lumen, and patient-side output lumen are closed by the control circuit of the fluid access device 700. This action isolates the fluidic interface between the machine-side hydraulic circuit and the patient-side hydraulic circuit.

Additionally, valves disposed in-line with the machine-side recirculation lumen and patient-side recirculation lumen are opened. This action fluidically bridges the machine-side input lumen to the machine-side output lumen via the machine-side recirculation lumen, and bridges the patient-side input lumen to the patient-side output lumen with the patient-side recirculation lumen.

In a fourth step shown in FIG. 7D, the cannulas are retracted at the fluidic interface, thereby completing the fluidic isolation of the machine-side hydraulic circuit from the patient-side hydraulic circuit.

Additionally, one or more in-line pumps disposed on the patient-side hydraulic circuit are turned on, causing fluid to recirculate therein. Fluid also recirculates through the machine-side hydraulic circuit under the motive power of the hemodialysis system pumps.

In a fifth step shown in FIG. 7E, the fluidic interface is sterilized and/or sanitized with a sanitization module. In an embodiment, the fluidic interface is sterilized by irradiating the fluidic interface with ultraviolet light from one or more UV light emitting diodes disposed on the base.

In a sixth step shown in FIG. 7F, closure mechanisms such as shutters are closed at the fluidic interface, thereby sealing distal ends (i.e., ends at the fluidic interface) of the machine-side input lumen, machine-side output lumen, patient-side input lumen, and patient-side output lumen.

In a seventh step shown in FIG. 7G, a retention mechanism is disengaged from the machine-side hydraulic circuit and/or the patient-side hydraulic circuit, thereby enabling physical separation of the two hydraulic circuits.

In an eighth step shown in FIG. 7H, the machine-side hydraulic circuit is physically separated from the patient-side hydraulic circuit. Following separation, patient-side fluid continues to recirculate fluid under the power of the in-line pumps, and machine-side fluid continues to recirculate fluid under the power of the hemodialysis system pumps.

Figure 8:
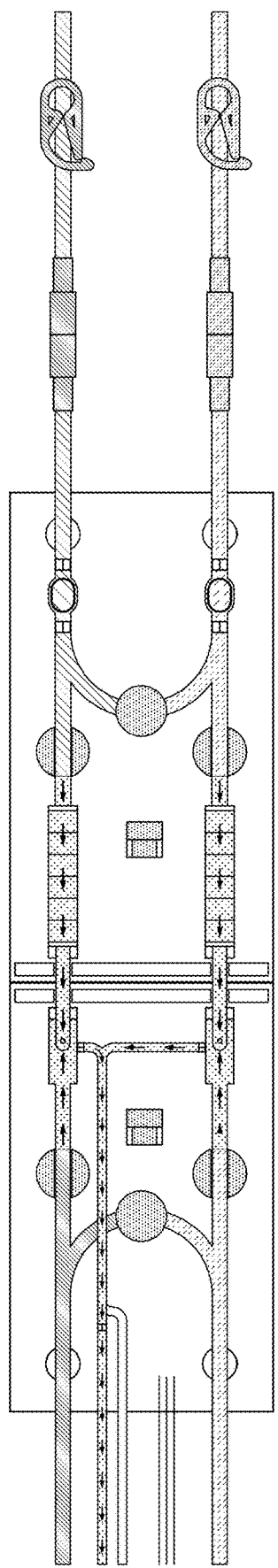
FIG. 8 shows a step in a representative method of coupling the machine-side hydraulic circuit of the fluid access device of FIG. 7A-FIG. 7H to a patient-side hydraulic circuit of the same.
Figure 9A:
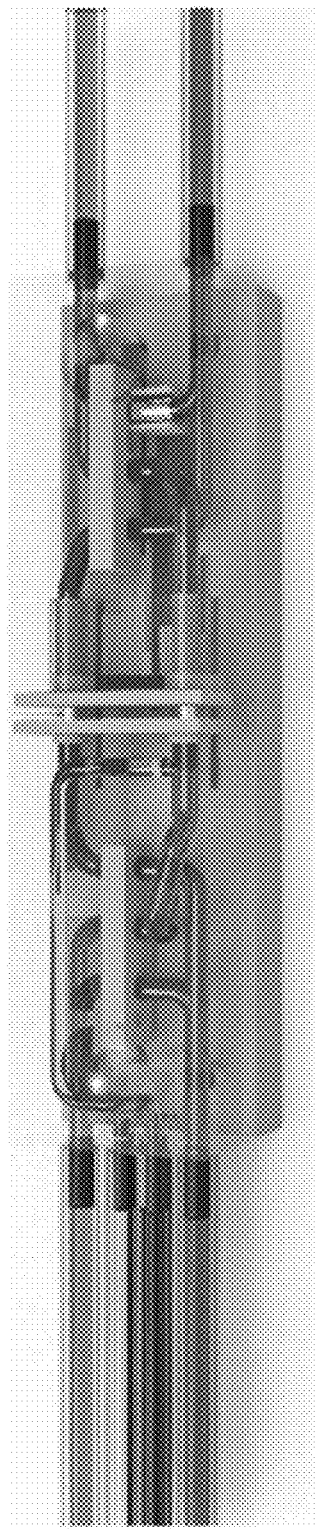
FIG. 9A-FIG. 12 show perspective views and schematic views of another fluid access device of the present disclosure.
Figure 9B:
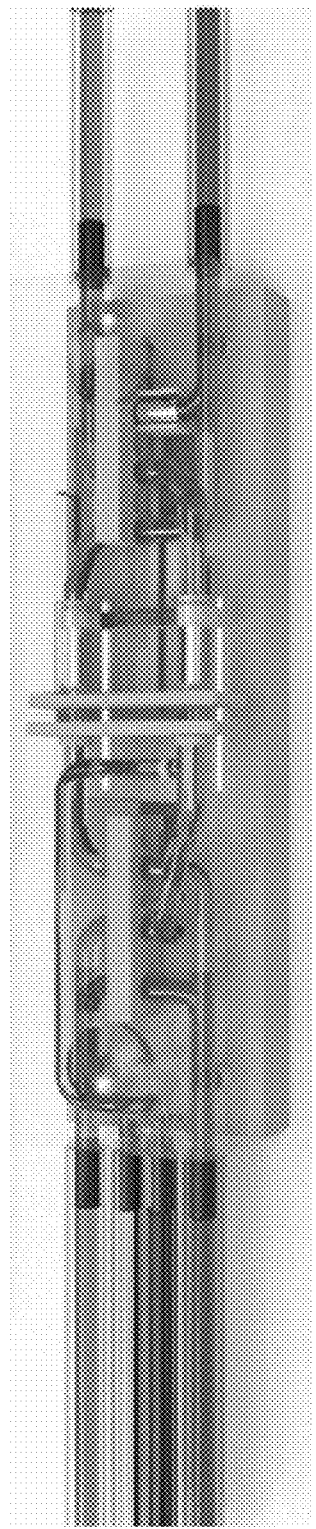
Figure 9C:
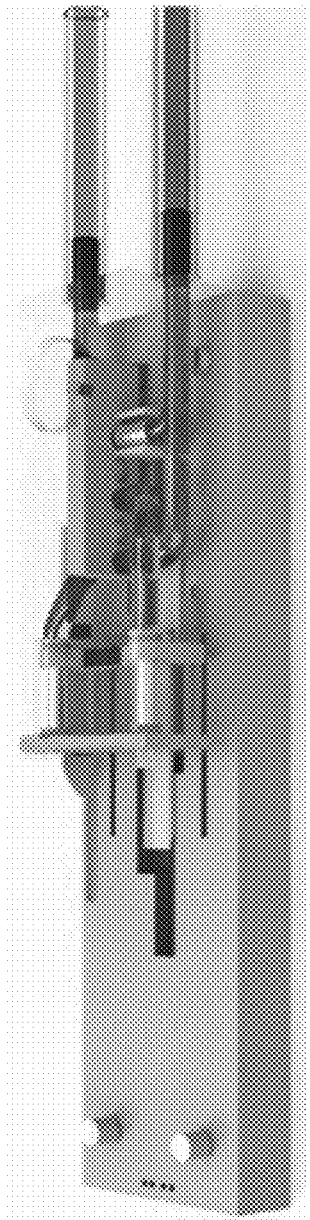
Figure 10:
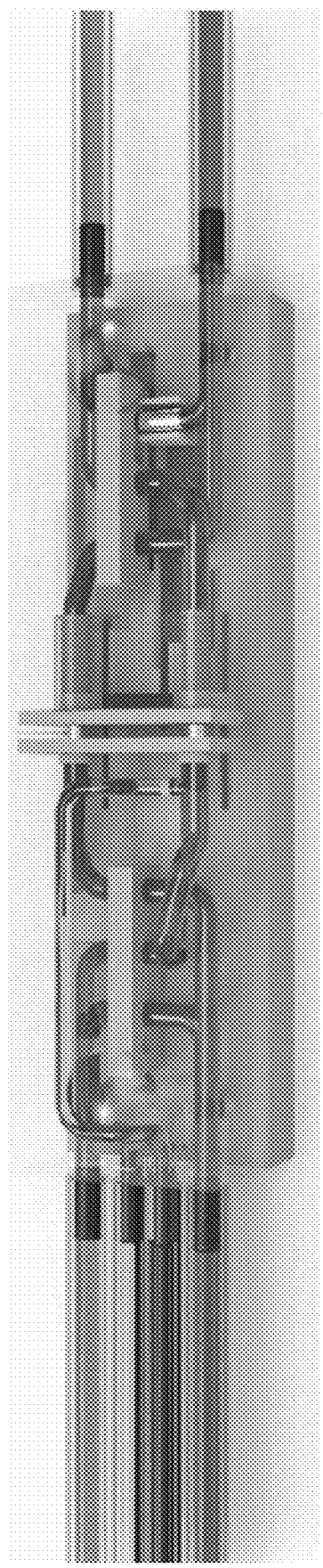
Figure 11:
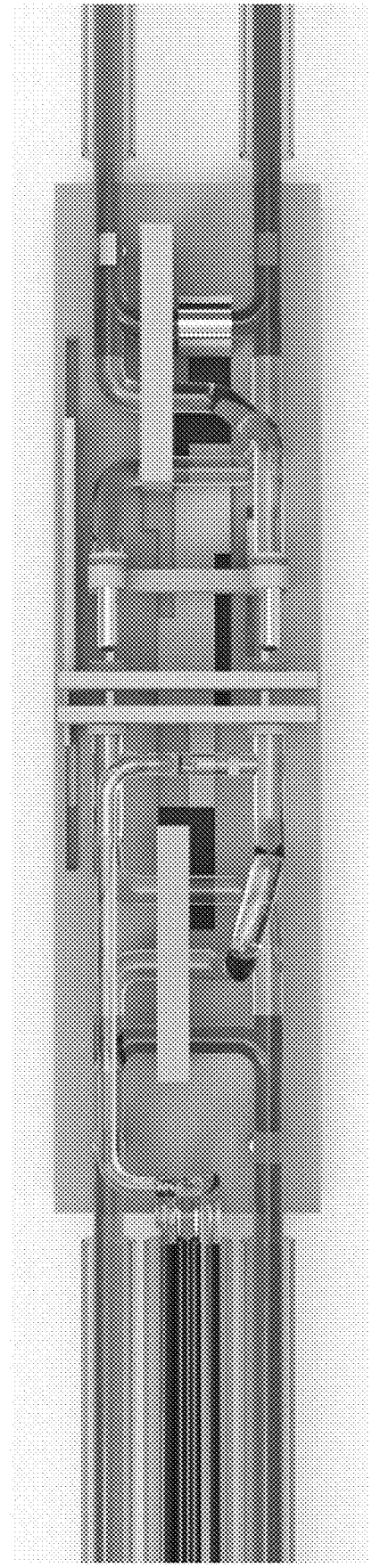
Figure 12:
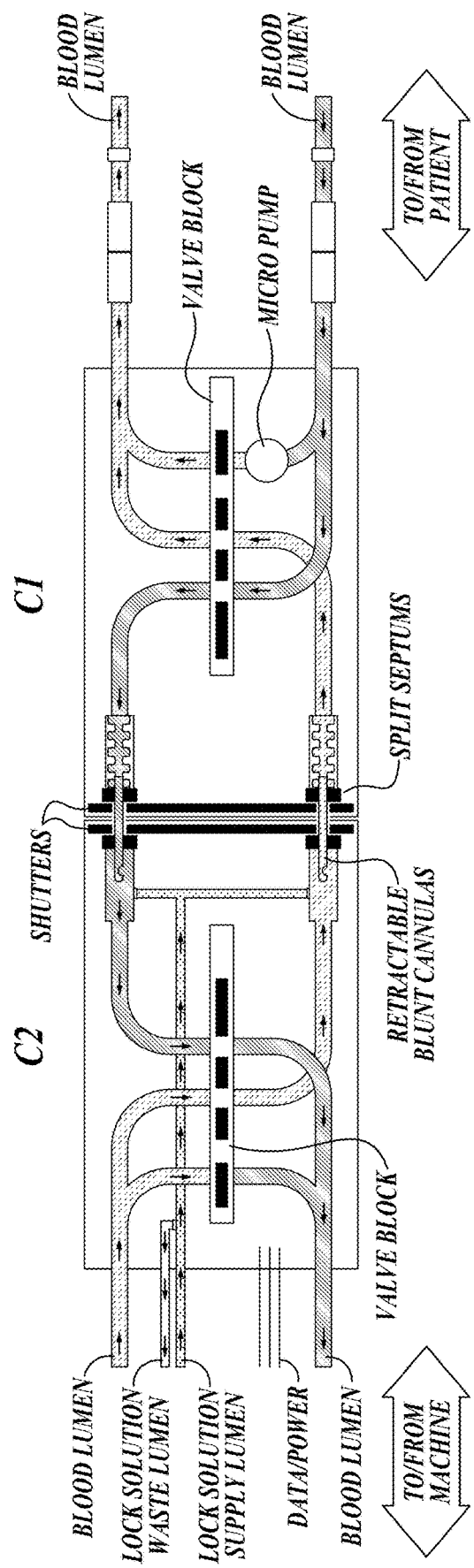

In an embodiment, a method of transitioning of the fluid access device from a disconnected state to a connected state is executed in the reverse order of FIG. 7A-FIG. 7H. That is, the machine-side hydraulic circuit is physically connected to the patient-side hydraulic circuit, which are then locked together with a retention mechanism. Then, the closure mechanisms are retracted, exposing distal ends the lumens at the fluidic interface. The fluidic interface are then sterilized with a sanitization module. Then, the cannulas are extended, thereby fluidically connecting the machine-side hydraulic circuit to the patient-side hydraulic circuit. Then, valves disposed in-line with the machine-side input lumen, machine-side output lumen, patient-side input lumen, and patient-side output lumen are opened by the control circuit. Additionally, valves disposed in-line with the machine-side recirculation lumen and patient-side recirculation lumen are closed. Optionally, and as shown in FIG. 8, the solution hydraulic circuit draws lock solution from the lumens into the solution waste lumen, and fluid flows freely between the machine-side hydraulic circuit and the patient-side hydraulic circuit.

The fluid access devices of the present disclosure are not limited to the specific configurations described above. FIG. 9A-FIG. 33B describe variations and optional features, any one or more of which may be incorporated into any fluid access device of the present disclosure.

FIG. 9A-FIG. 12 show an alternative embodiment of a fluid access device according to the present disclosure. The alternative fluid access device of FIG. 9A-12 includes the same features as the previously described embodiments, but with a different pump and valve configuration. In particular, each of the patient-side and machine-side hydraulic circuits includes a single valve block rather than a number of discrete valves. The valve block selectively acts on each of the lumens in accordance with the connected/disconnected states discussed above.

FIG. 13A-FIG. 13B show an alternative connection structure which may be utilized in connection with any fluid access device of the present disclosure.

As shown, a fluid access device 1300 includes a patient-side hydraulic circuit 1302 and a machine-side hydraulic circuit 1304 as described above. Unlike the previous embodiments which utilize a latch-type coupling to physically connect the patient-side hydraulic circuit and the machine-side hydraulic circuit, fluid access device 1300 utilizes a lead screw mechanism. In particular, the machine-side hydraulic circuit 1304 includes a lead screw 1306 which may be rotated by an electric motor, a pneumatic motor, or manually. In the embodiment shown, the lead screw 1306 is rotatably driven by a pneumatic motor, e.g., a turbine coupled with a pneumatic supply line. The patient-side hydraulic circuit 1302 includes a threaded portion 1308 sized and positioned to receive the lead screw 1306 when the patient-side hydraulic circuit 1302 and machine-side hydraulic circuit 1304 are coupled together.

The fluid access device 1300 includes another variation which may be utilized in any fluid access device of the present disclosure. Namely, needles and septa are utilized to fluidically couple the patient-side hydraulic circuit 1302 and machine-side hydraulic circuit 1304 rather than cannulas (otherwise, similar hydraulic connections are presumed and not show again for simplicity). In particular, machine-side hydraulic circuit 1304 includes needles 1310, 1312, while the patient-side hydraulic circuit 1302 includes self-healing septa 1314, 1316. Retractable closure mechanisms (e.g., shutters 1318, 1320) are biased to the closed state shown in FIG. 13A in order to protect the needles 1310, 1312 when the fluid access device is in a disconnected state.

In use, to join together the patient-side hydraulic circuit 1302 and the machine-side hydraulic circuit 1304, the threads of the lead screw 1306 are engaged with the threaded portion 1308. The lead screw 1306 is rotated by the motor such that the machine-side hydraulic circuit 1304 advances toward the patient-side hydraulic circuit 1302. The needles 1310, 1312 penetrate the septa 1314, 1316 under the driving force of the lead screw 1306 until the patient-side hydraulic circuit 1302 and machine-side hydraulic circuit 1304 are fluidically connected.

Advantageously, as the lead screw 1306 advances the hydraulic circuits toward each other, the shutters 1318, 1320 open simultaneously and automatically. The reverse is true upon disconnection of the two hydraulic circuit, i.e., the shutters close automatically in order to prevent contamination and to waterproof the device. Automatic shutter opening/closure reduces the need for human intervention to sanitize and secure the device. In any embodiment, the advancement of the two hydraulic circuits also causes electrical and/or pneumatic connection between the two hydraulic circuits.

Figure 14B:
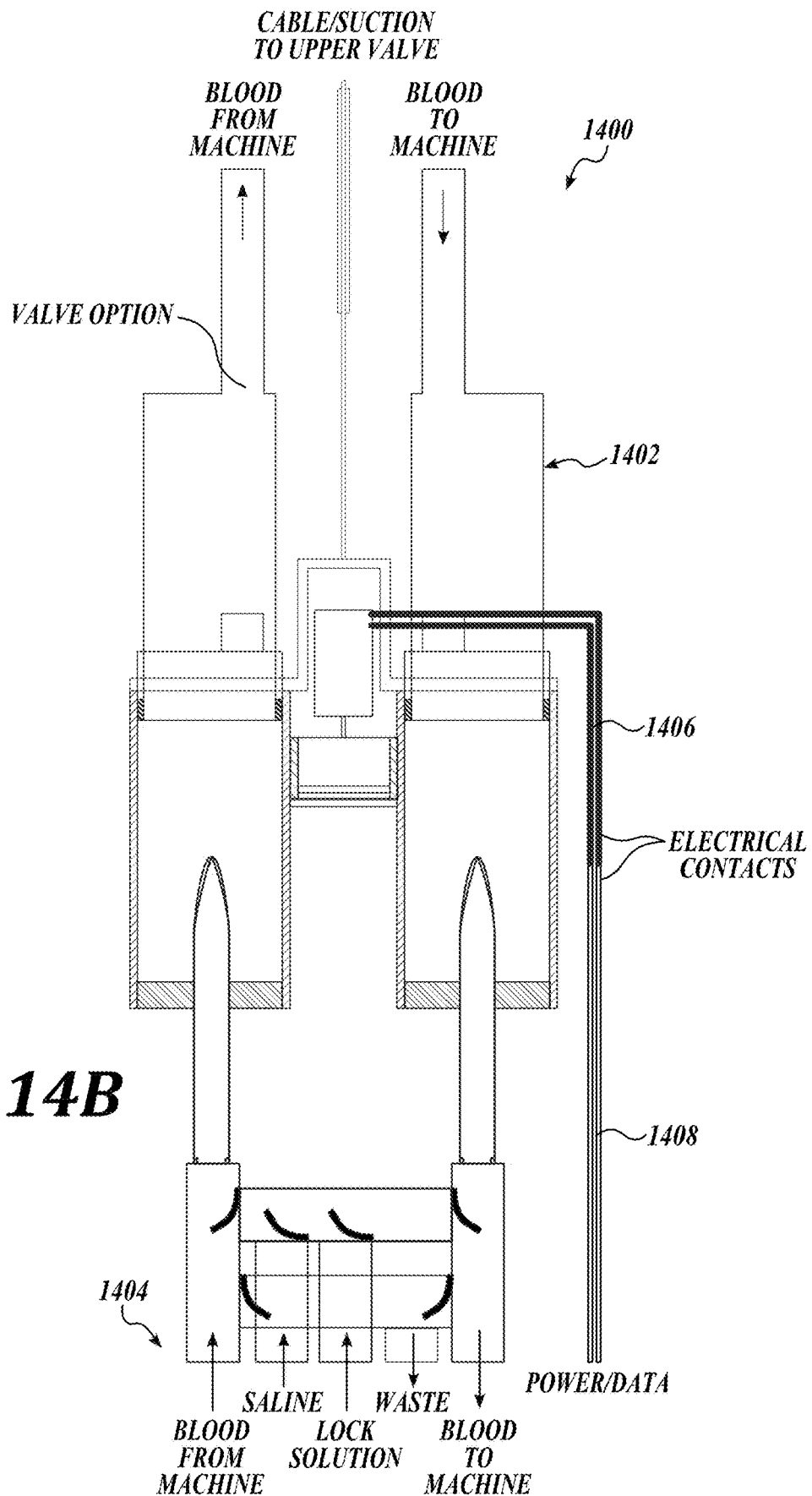
FIG. 14B shows a schematic top view of the fluid access device of FIG. 14A in a connected state.

FIG. 14A and FIG. 14B illustrate a fluid access device 1400 which includes an electrical connection scheme which may be utilized with any fluid access device of the present disclosure to transfer power and/or electrical signals between the two hydraulic circuits.

Patient-side hydraulic circuit 1402 and machine-side hydraulic circuit 1404 respectively include electrical contacts 1406, electrical contact 1408. The electrical contact 1408 is electrically coupled with a power supply of a control circuit, a hemodialysis system, or the like. The electrical contact 1406 is operatively coupled to at least one electrical load such as motor 1410, which in the illustrated embodiment opens and closes shutters 1412. In other embodiments, the electrical load operates a sensor, a communications device, a lead screw, a latch, and/or any other electrical device on the patient-side hydraulic circuit.

In the disconnected state of FIG. 14A when the patient-side hydraulic circuit 1402 and machine-side hydraulic circuit 1404 are in a disconnected state, the electrical contacts 1406, 1408 are also disconnected. However, when the hydraulic circuits are physically connected, the electrical contacts 1406, 1408 are electrically coupled such that the power supply can power the electrical loads in the patient-side hydraulic circuit.

Figure 15A:
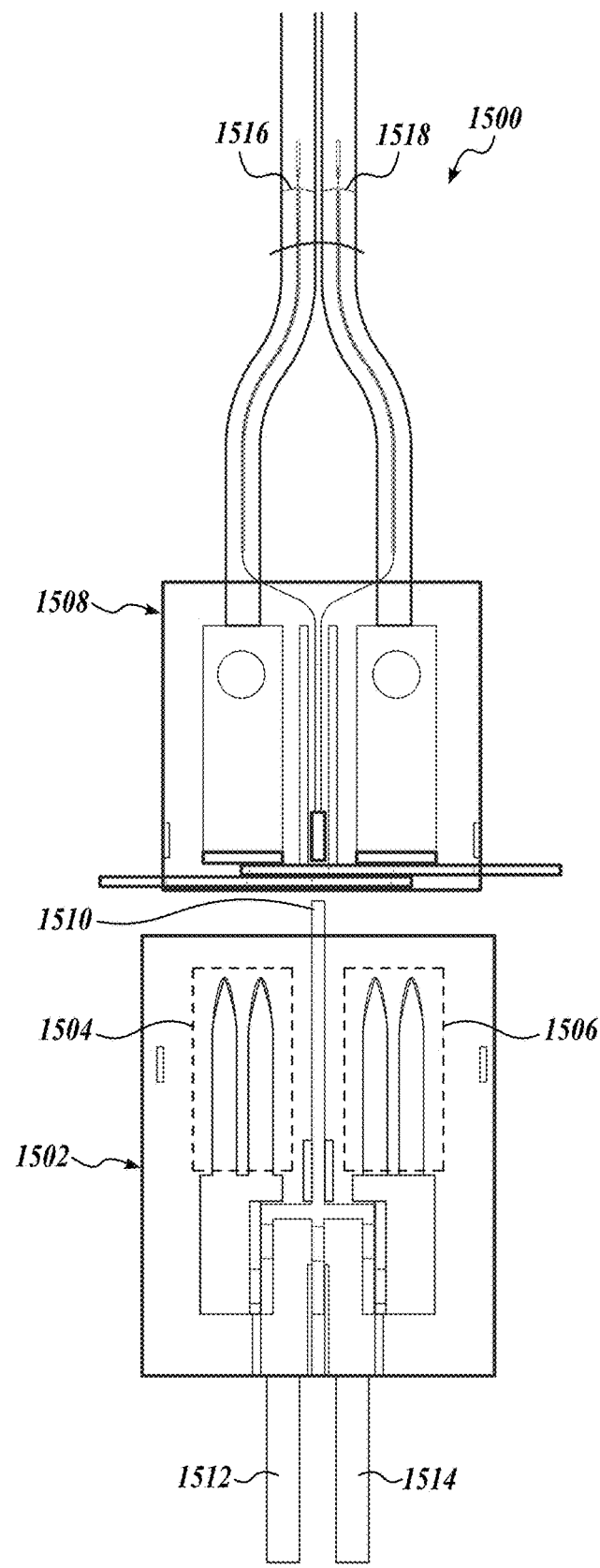
FIG. 15A shows a schematic top view of a fluid access device in a disconnected state according to the present disclosure.
Figure 15B:
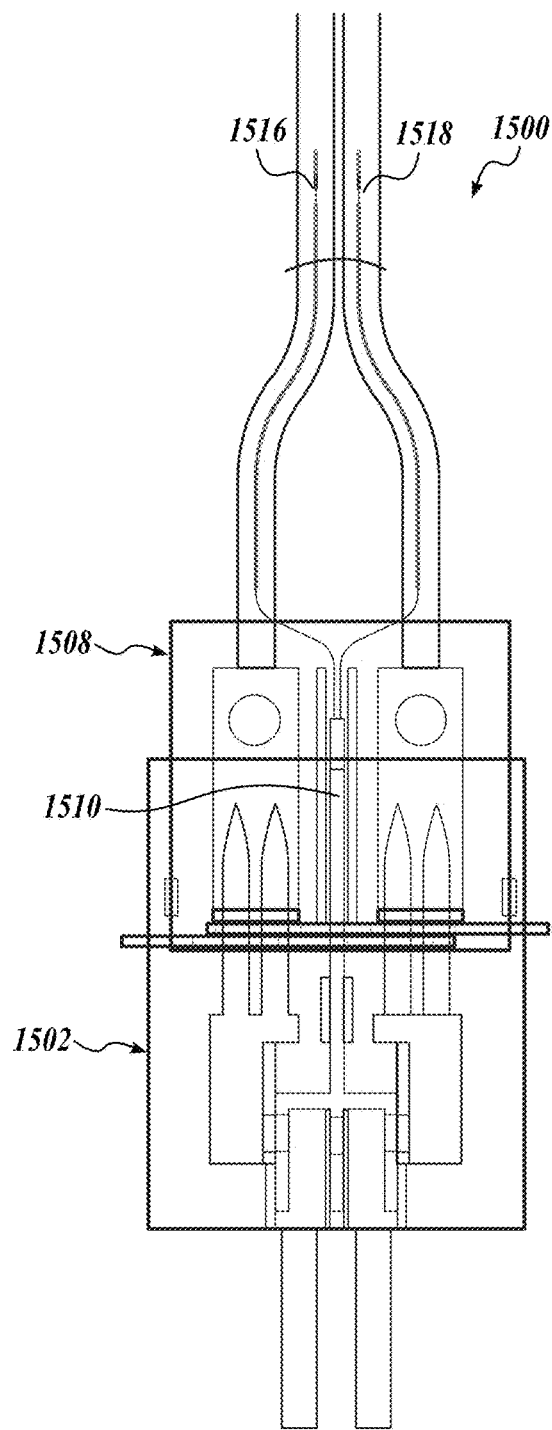
FIG. 15B shows a schematic top view of the fluid access device of FIG. 15A in a connected state.

FIG. 15A and FIG. 15B show another fluid access device 1500 having a multi-needle and septa fluid connection scheme which may be utilized in any fluid access device of the present disclosure, e.g., as an alternative to cannulas or single-needle fluidic coupling setups in order to increase fluid flow rate. In particular, machine-side hydraulic circuit 1502 includes a first plurality of needles 1504 and a second plurality of needles 1506 which are fluidically connected to respective fluid access lines 1512, 1514. Needles 1504 and 1506 could be respectively connected to the machine-side input lumen and machine-side output lumen, or vice versa. In some embodiments, the needles 1504, 1506 could be disposed on the patient-side hydraulic circuit 1508 rather than the machine-side hydraulic circuit 1502. Advantageously, providing a plurality of needles (e.g., two, three, or four needles) for each of the inputs and outputs can increase flow rate and reduce damage to the self-healing septa.

Fluid access device 1500 includes another feature which may be utilized with any fluid access device of the present disclosure. Machine-side hydraulic circuit 1502 includes an actuator (in this embodiment, a pin 1510) which actuates intraluminal valves 1516, 1518 in the patient-side hydraulic circuit 1508 when the machine-side hydraulic circuit 1502 couples with the patient-side hydraulic circuit 1508. Such intraluminal valves may default to a closed position (shown in FIG. 15A) that fluidically closes or occludes the patient-side input and output lumens unless physically opened by the pin 1510 (e.g., via a linkage). When the machine-side hydraulic circuit 1502 couples with the patient-side hydraulic circuit, the pin 1510 causes the valves 1516, 1518 to retract such that they do not occlude the corresponding lumens. Advantageously, this feature automates transition from the disconnected state to the connected state, and prevents unintended fluid loss (e.g., bleed out) from a patient in the event the hydraulic circuits are unintentionally separated. Representative intraluminal valves are described below.

Figure 16:
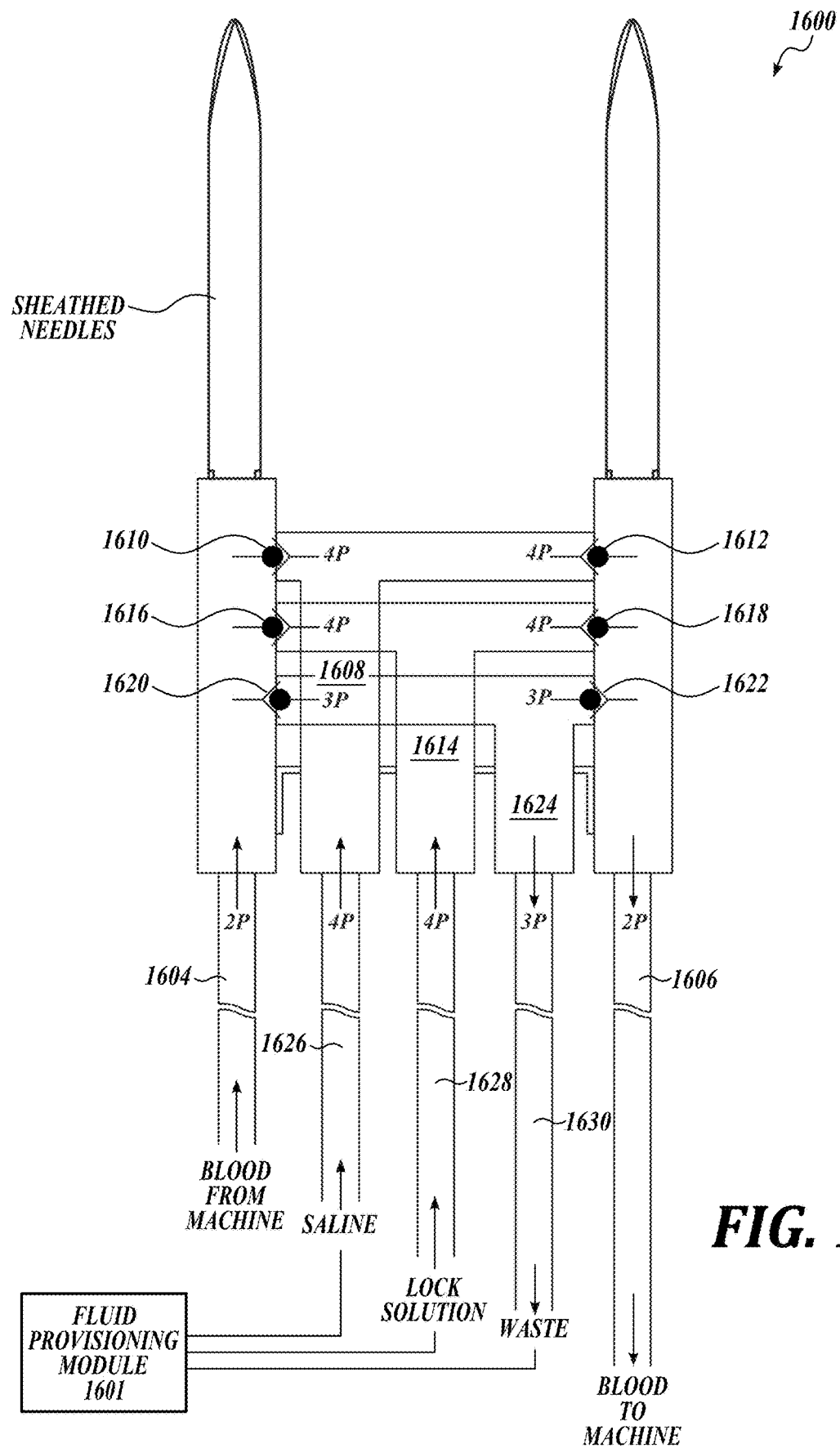
FIG. 16 shows a schematic top view of a manifold of a fluid access device according to the present disclosure.

FIG. 16 illustrates a fluid access device 1600 which includes a manifold 1602 which may be utilized with any fluid access device of the present disclosure, e.g., as part of a solution hydraulic circuit as described above. Fluid access devices of the present disclosure may interact with several fluids, including blood, lock solutions (e.g., heparin and sodium citrate), cleaning solutions (e.g., saline), priming/rinseback/flushing fluid (again, saline), and waste fluid. The manifold 1602 provides a novel structure to manage such fluids. In any embodiment, a separate and optional fluid provisioning module 1601 may be configured to supply and/or receive any one or more of the foregoing fluids to/from the fluid access device 1600.

Generally, manifold 1602 is fluidically coupled between machine-side input lumen 1604 and machine-side output lumen 1606, and includes passive valving (e.g., check valves) that regulates the flow of fluids to/from the machine-side input lumen 1604 and machine-side output lumen 1606 under different pressure conditions.

A first manifold conduit 1608 of manifold 1602 is fluidically coupled between machine-side input lumen 1604, machine-side output lumen 1606 and a first solution conduit 1626 (e.g., a saline conduit). The first solution conduit 1626 provides a first solution (e.g., saline) to the first manifold conduit 1608, and check valves 1610, 1612 permit one-directional passage of the first fluid from the first manifold conduit 1608 into the machine-side input lumen 1604 and machine-side output lumen 1606, respectively, under a first pressure threshold (e.g., 2× the normal operating pressure of the machine-side input lumen 1604 and machine-side output lumen 1606).

A second manifold conduit 1614 of manifold 1602 is fluidically coupled between machine-side input lumen 1604, machine-side output lumen 1606, and a second solution conduit 1628. The second solution conduit 1628 provides a second solution (e.g., a lock solution such as heparin) to the second manifold conduit 1614, and check valves 1616, 1618 permit one-directional passage of the second fluid from the second manifold conduit 1614 into the machine-side input lumen 1604 and machine-side output lumen 1606, respectively, under a second pressure threshold, which may be the same or different from the first pressure threshold (e.g., 2× the normal operating pressure of the machine-side input lumen 1604 and machine-side output lumen 1606).

A third manifold conduit 1614 of manifold 1602 is fluidically coupled between machine-side input lumen 1604, machine-side output lumen 1606, and a third solution conduit 1630. Check valves 1620, 1622 permit one-directional passage of a third fluid (e.g., waste) from the machine-side input lumen 1604 and machine-side output lumen 1606 into the third manifold conduit 1624 and into the third solution conduit 1630, under a third pressure threshold, which may be the same or different from the first and/or second pressure thresholds (e.g., 1.5× the normal operating pressure of the machine-side input lumen 1604 and machine-side output lumen 1606).

Thus, the manifold 1602 enables selective passage of some fluids (e.g., lock solution and/or saline) into the fluid conduits which carry the patient's blood, and permits selective evacuation of waste fluid. Although the illustrated device includes three conduits, this number is representative, not limiting. Other embodiments contemplate a different number, e.g., two, four, or five conduits, each of which may be valved to provide fluid into, or to receive fluid from, the machine-side input lumen 1604 and machine-side output lumen 1606. Moreover, the flow direction of each conduit may vary between embodiments. Further, in some embodiments, the lumens (conduits) could be controlled by active valving and/or contain bidirectional valving.

As described above, some fluid access devices of the present disclosure include a permanent recirculation lumen between the patient side input and output lumens, and/or between the machine-side input and output lumens. While such embodiments are advantageous, the recirculation lumen is an optional feature. Embodiments of any fluid access device of the present disclosure may not include such permanent recirculation lumens, or any recirculation lumens. Indeed, the present disclosure expressly contemplates that any embodiment described herein may alternatively be provided without one or more recirculation lumens. Such embodiments still offer clear benefits to patients by reducing human touchpoints reducing infection risk, and facilitating monitoring of the patient's fluids.

Figure 17:
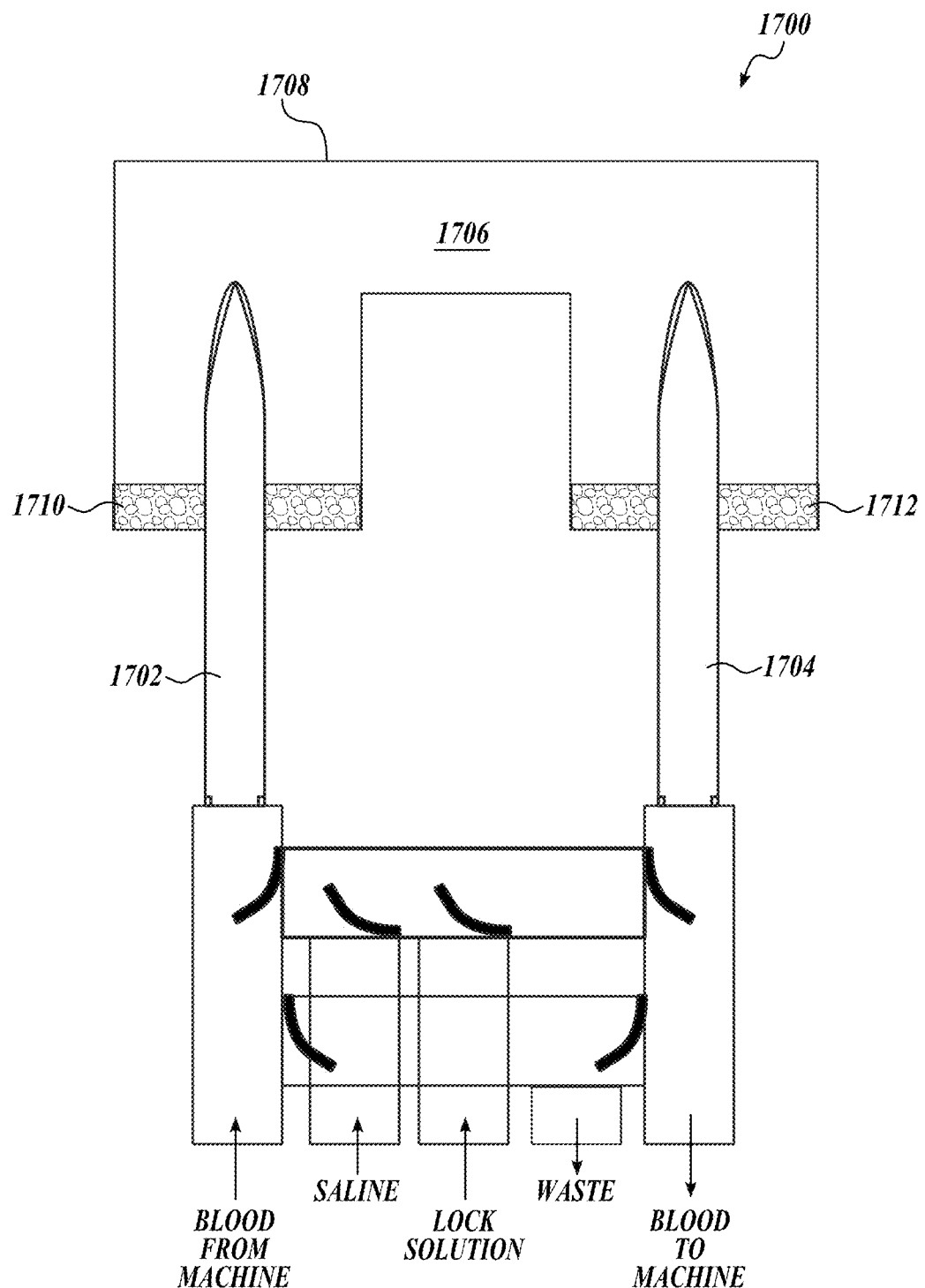
FIG. 17 shows a schematic top view of a recirculation bridge for a fluid access device according to the present disclosure.

FIG. 17 provides an optional solution to bridge the input and output lumens in any fluid access device of the present disclosure, particularly those without a permanent recirculation lumen.

As shown, the fluid access device 1700 includes needles 1702, 1704, which correspond to a machine-side input lumen and a machine-side output lumen, respectively. A recirculation bridge 1706 (essentially, a removable cap forming a channel therein) fluidically connects the needles 1702, 1704 with a U-shaped fluidic pathway. In particular, a housing 1708 of the recirculation bridge 1706 forms a U-shaped channel therein. The U-shaped recirculation bridge 1706 includes self-healing septa 1710, 1712 at each end, respectively. In use, the needles 1702, 1704 are respectively inserted into the septa 1710, 1712, and thereafter a patient's blood can recirculate from the machine-side output lumen to the machine-side input lumen to prevent clotting on the machine side or alternatively from the patient-side output lumen to the patient-side input lumen under the motive power of a pump as described herein.

Figure 18:
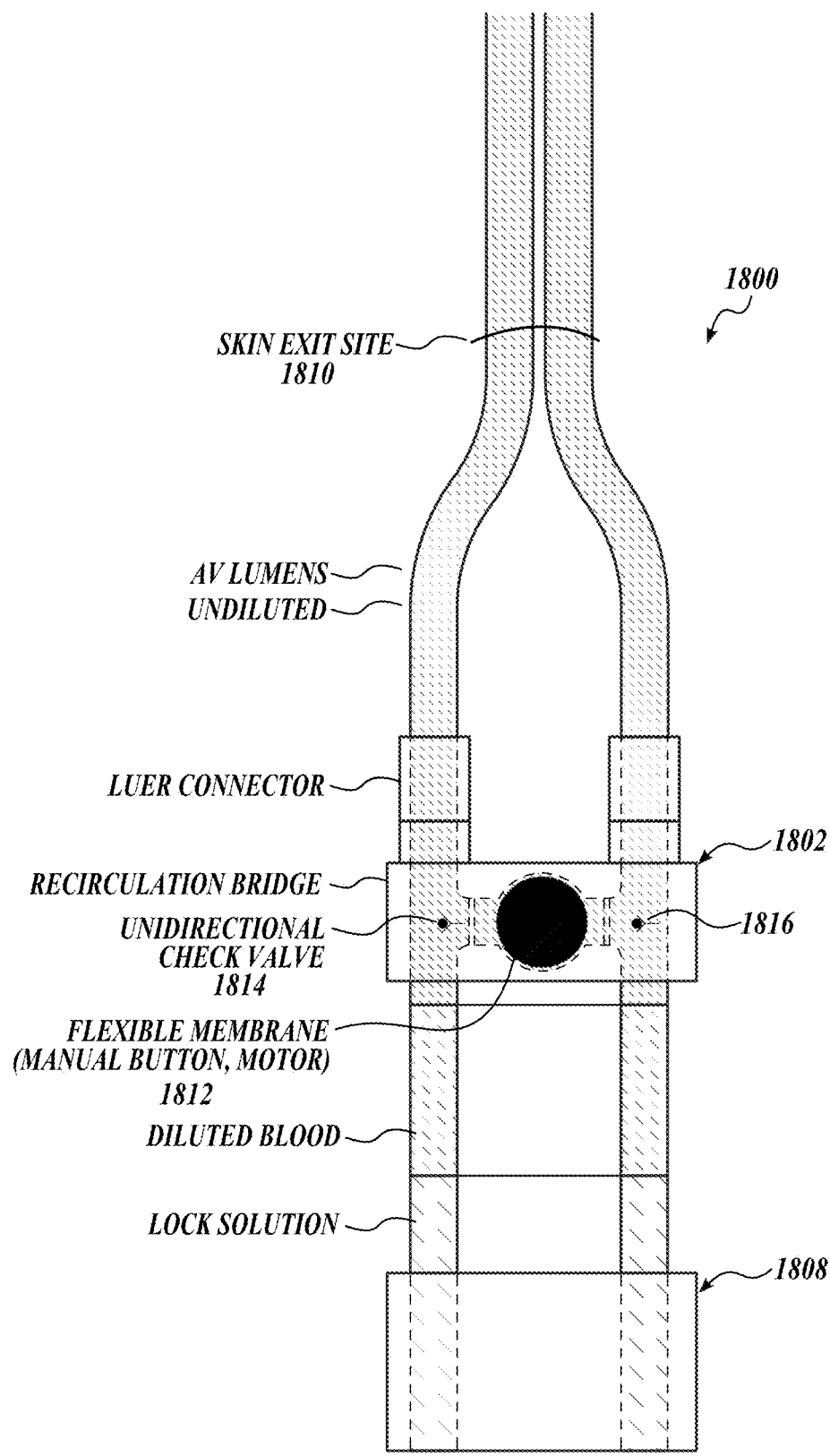
FIG. 18 shows a schematic top view of another recirculation bridge for a fluid access device according to the present disclosure.

FIG. 18 illustrates a representative fluid access device 1800 having a recirculation bridge 1802, which may be utilized with any fluid access device of the present disclosure, and in particular on any patient-side or machine-side hydraulic circuit. For example, a system may include any fluid access device of the present disclosure in addition to a segment of the fluid access line which includes the recirculation bridge 1802. In some embodiments, the recirculation bridge 1802 fluidically bridges the patient-side input lumen 1804 and the patient-side output lumen 1806 between a fluid access device 1808 and a skin access site 1810. Advantageously, this enables the fluid access device 1808 to be disconnected from a hemodialysis system and locked with a lock solution, while still enabling circulation of the patient's blood. Thus, the recirculation bridge 1802 may form part of a fluid access device, or may be provided separately from a fluid access device, e.g., as part of a fluid access system.

In this embodiment, the recirculation bridge 1802 permits blood passage from the patient-side output lumen 1806 to the patient-side input lumen 1804 via manual palpation of a flexible membrane 1812 or diaphragm, which pumps the blood. Accordingly, one or more check valves are disposed at the junction(s) between the input/output lumens and the recirculation bridge 1802 to ensure one-directional flow. In the illustrated embodiment, a check valve 1814 is disposed upstream of the flexible membrane 1812, and an optional check valve 1816 is disposed downstream of the flexible membrane 1812. In other embodiments include the check valve 1816, but not the check valve 1814.

The fluid access devices of the present disclosure provide an advantageous platform from which to monitor a patient's health and/or to sample biological fluids from the patient. For example, in practice, the inventive blood access devices are likely to be positioned relatively close to the patient's heart. This, in turn, enables sensing parameters of the patient's blood and other biological fluids with great resolution.

Figure 19A:
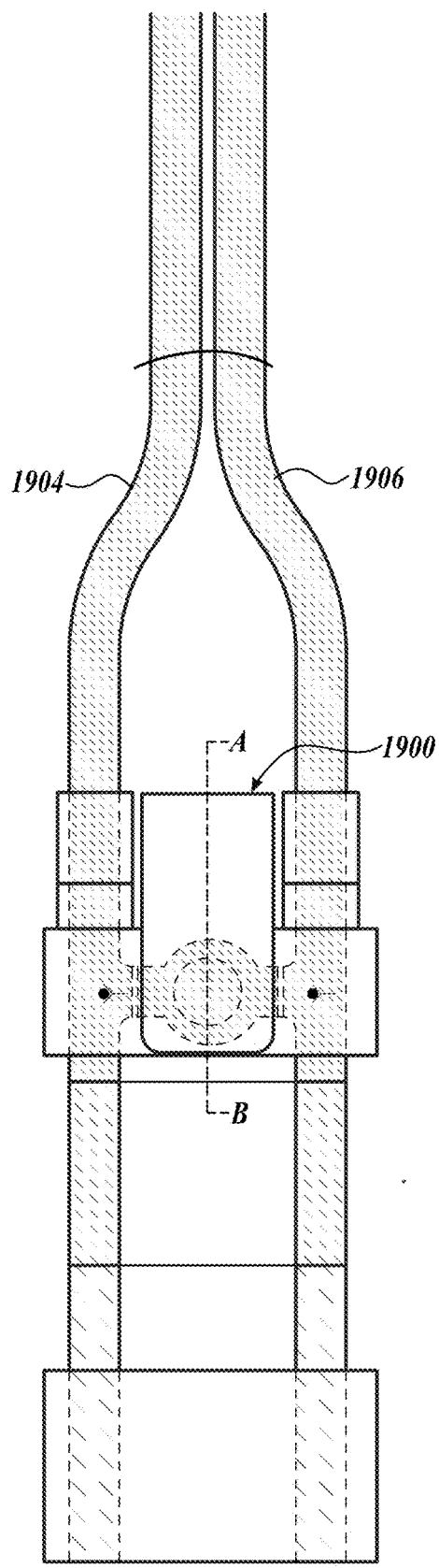
FIG. 19A shows a top view of a fluid access device having an electronics module according to the present disclosure.
Figures 19B, 19C:
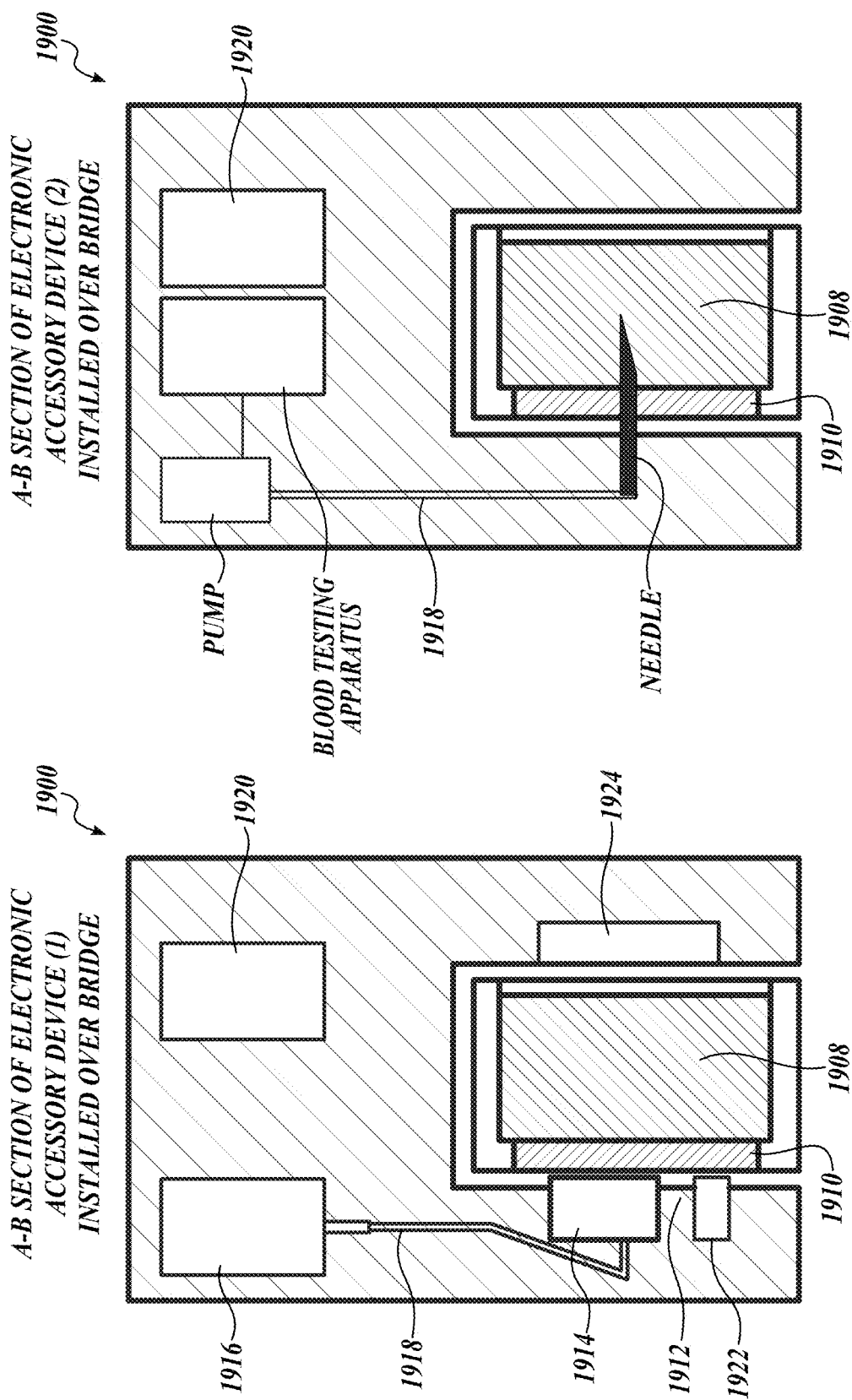
FIG. 19B shows a schematic section view of an electronics module according to the present disclosure.
FIG. 19C shows a schematic section view of another electronics module according to the present disclosure.

FIG. 19A-FIG. 19C show representative electronics module 1900 which may integrate as an optional feature of any fluid access device or any recirculation bridge of the present disclosure, and which enable accurate sensing of the patient's fluid stream. In the illustrated embodiments, the electronics modules 1900 are configured for integration with a recirculation bridge 1902 which fluidically connects a patient-side output lumen 1904 and a patient-side input lumen 1906 of a patient-side fluid access device. In some embodiments, the electronics module 1900 integrates with a different portion of the fluid access line or fluid access device, either on the machine-side or the patient side.

The electronics module 1900 is reversibly coupled with a docking interface of the recirculation bridge 1902, such that different electronics modules may be connected for different purposes. Section views of representative electronics modules are provided in FIG. 19B and FIG. 19C.

FIG. 19B shows a section view of one representative electronics module 1900. As shown, the electronics module 1900 is disposed around a blood channel 1908 of the recirculation bridge 1902. In particular, the electronics module 1900 forms a U-shape or C-shape which is sized to receive a patient fluid channel therein (in this embodiment, blood channel 1908). A membrane 1910 is disposed in a wall of the blood channel 1908 and forms part of the recirculation bridge 1902 (in particular, a docking interface 1912 thereof). The docking interface may optionally include a locking mechanism that selectively engages the electronics module 1900 thereon, e.g., a latch, magnet, or the like.

The electronics module 1900 docks with the docking interface such that it is configured to palpate the membrane 1910 with a piston 1914, which is in turn driven by a motor 1916 via a linkage 1918. An on-board battery 1920 may be, for example, a rechargeable Li-ion battery. Electronics module 1900 includes one or more optional sensors such as pressure sensor 1922 (which monitors blood pressure in the blood channel 1908 through the membrane 1910) and optical sensor 1924 (which monitors blood flow in the blood channel 1908). In any embodiment, one or more of the sensors 1922, 1924 may be configured to detect at least one of: a pathogen in the blood channel, a temperature of blood in the blood channel, a color of blood in the blood channel, a pressure of blood in the blood channel, or a clarity of blood in the blood channel. Given the close proximity to the patient, said sensors are well positioned to detect infection or symptoms of infection with high resolution.

FIG. 19C shows a section view of another representative electronics module 1900 configured to dock with the docking interface of the recirculation bridge 1902. The electronics module 1900 comprises a needle configured to sample blood in the blood channel 1908 through the membrane 1910, and a testing apparatus configured to test the blood for one or more relevant parameters, such a urea concentration.

The foregoing electronics modules are representative, not limiting.

Figure 20:
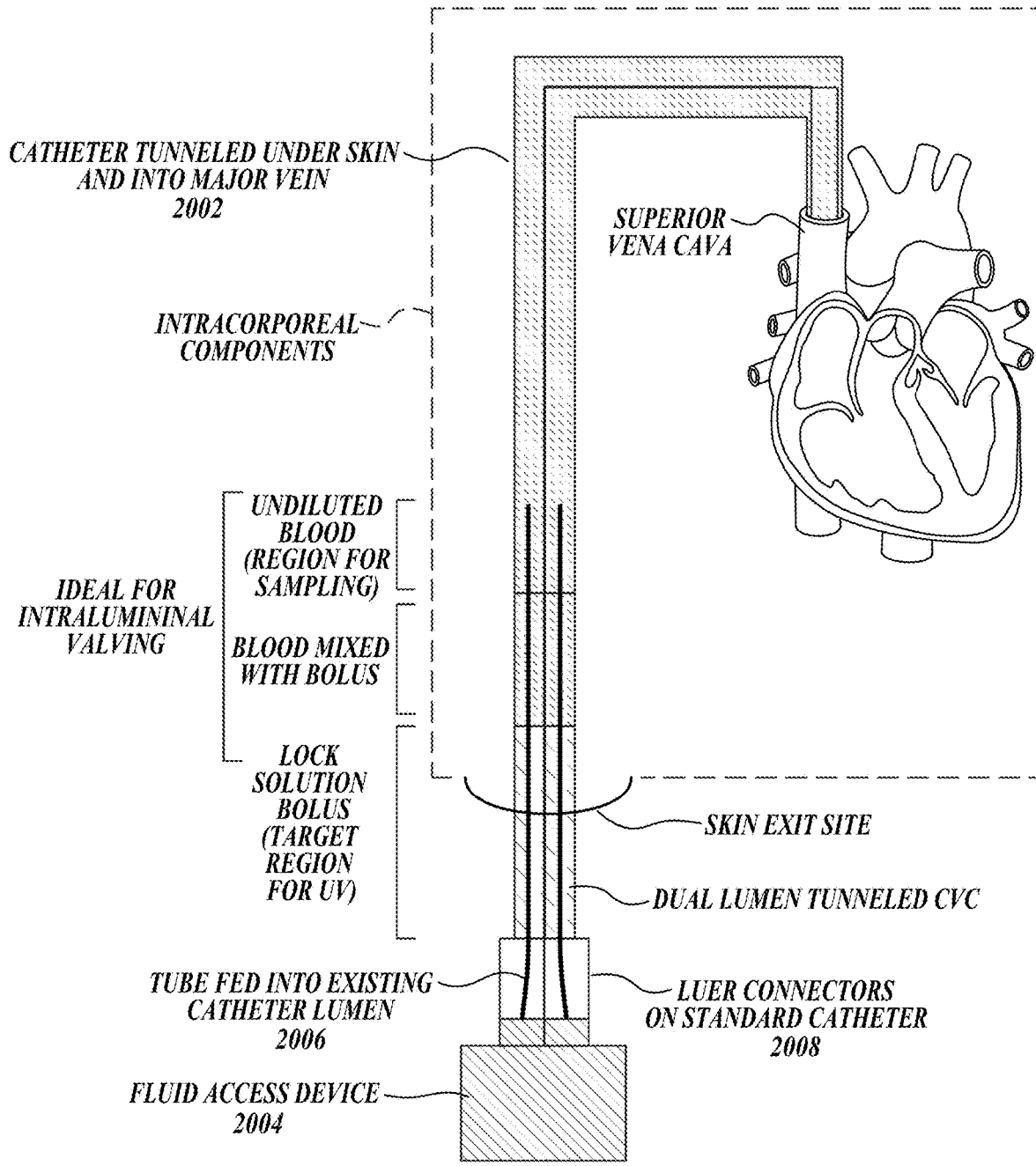
FIG. 20 shows a schematic top view of a fluid connection scheme between a fluid access device and a patient blood access device.

FIG. 20 shows one representative configuration in which any fluid access device of the present disclosure may be connected with a patient.

In the illustrated embodiment, the patient has an implanted blood access device 2002, e.g., a central venous catheter, a fistula, a bypass graft, or the like. A fluid access device 2004 (having the configuration of any fluid access devices described herein) is coupled to the access device 2002 with a fluid access line 2006, which includes a patient-side input lumen and a patient side patient-side output lumen as described above. Accordingly, the fluid access line 2006 may be a multi-lumen catheter having any of the cross sectional profiles shown herein, such as those described with respect to FIG. 29A-FIG. 29C.

The fluid access line 2006 is inserted into the patient's blood access device 2002, preferably to a location sufficiently proximal to the patient's heart that a proximal end of the fluid access line 2006 (i.e., the end nearest the heart) extends into an undiluted blood region of the blood access device 2002, i.e., past any region which includes blood diluted with saline and/or lock solution. The fluid access line 2006 includes a fluid coupling 2008 (e.g., a Luer lock) which enables reversible coupling with the patient's blood access device 2002.

Figure 21:
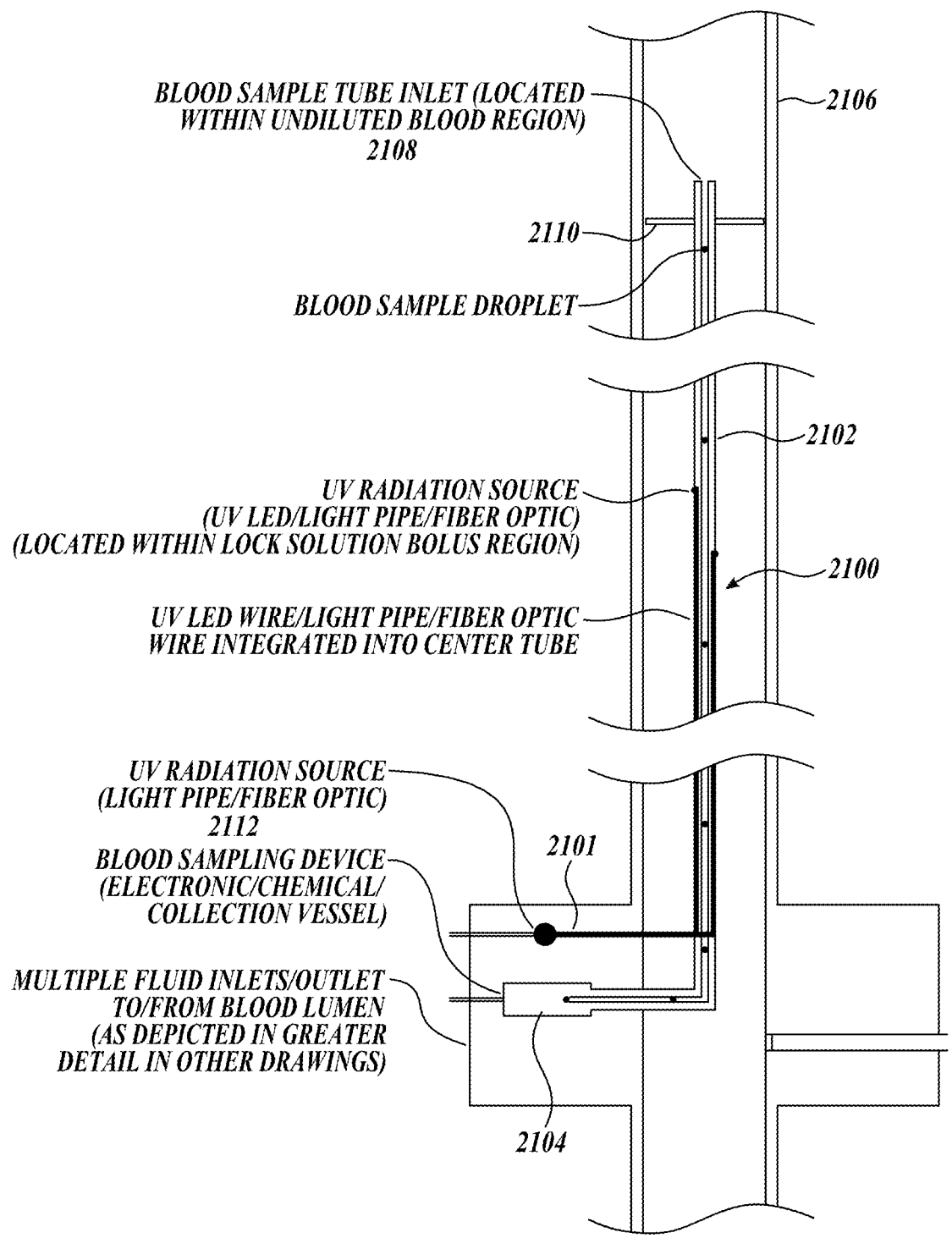
FIG. 21 shows a schematic top view of a blood sampling device of a fluid access device according to the present disclosure.

FIG. 21 shows a representative blood sampling device 2100 which may be incorporated as an optional feature of any fluid access device of the present disclosure, and which enables sampling of blood from a patient's bloodstream. As discussed above, the fluid access devices of the present disclosure are ideal platforms from which to sample and analyze a patient's biological fluids with high resolution, given the proximity to the patient.

The blood sampling device 2100 integrates with any fluid access device described herein, and includes a capillary tube 2102 which extends from an access site 2104 in the fluid access device 2101 (which may be configured to couple with a syringe or other device via Luer lock or similar coupling) into a lumen of the patient's catheter 2106 (or fistula or the like). The capillary tube 2102 has sufficient length that a tube inlet 2108 thereof extends to a location sufficiently proximal to the patient's heart such that undiluted blood may be sampled, i.e., from an undiluted blood region free of any blood diluted with saline and/or lock solution. In some embodiments, the capillary tube 2102 is coated with a pharmacological substance (e.g., heparin) or polymer coating to prevent clotting/fouling. Optionally, a centering device 2110 (e.g., an annular support, collar, strut, or similar) supports the tube inlet 2108 at a central location within the lumen of the patient's catheter 2106. In such embodiments, the centering device 2110 may be attached to the capillary tube 2102.

The access site 2104 includes an optional UV radiation source 2112 configured to disinfect the capillary tube 2102. In some embodiments, the UV radiation source 2112 includes a UV light source (e.g., an LED) optically attached to a light guide (e.g., a fiber optic filament or light pipe). The light guide extends along the capillary tube 2102 and irradiates the capillary tube 2102 and surrounding catheter lumen with UV light. In some embodiments, the light guide extends within the capillary tube 2102. In some embodiments, the light guide is configured to extend at least to a lock solution bolus region of the patient's catheter 2106.

Figure 22A:
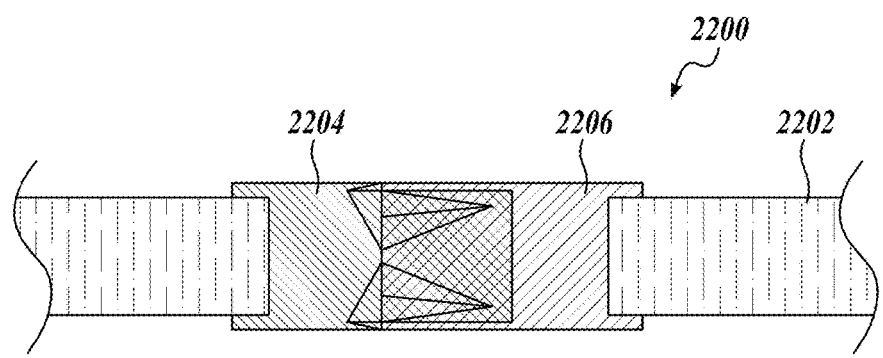
FIG. 22A-FIG. 22C show schematic views of a breakaway mechanism of a fluid access device according to the present disclosure.
Figure 22B:
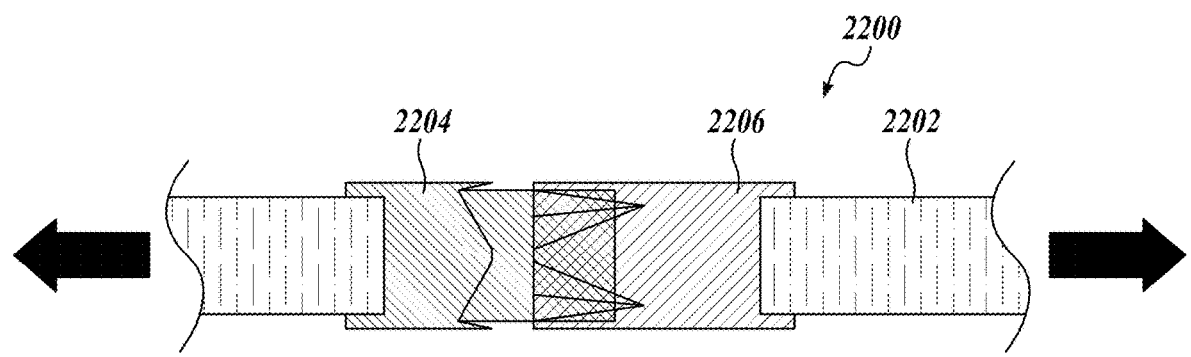
Figure 22C:
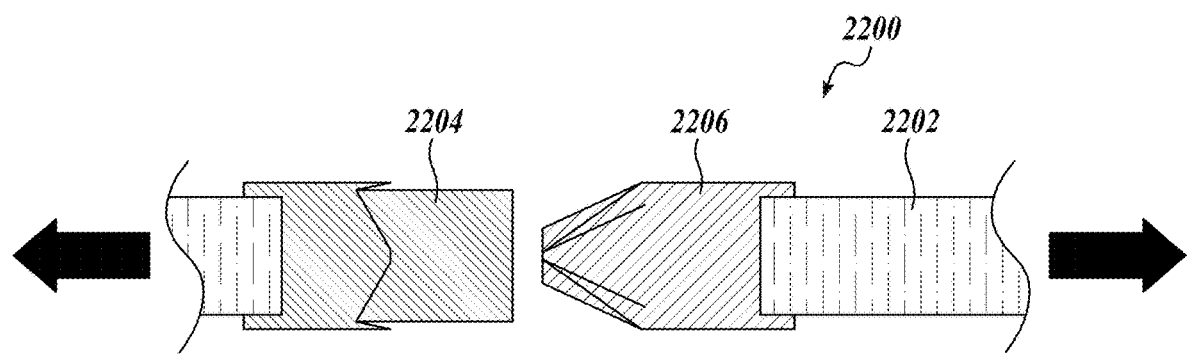

FIG. 22A-FIG. 22C show a representative breakaway mechanism 2200 which may be integrated into any fluid access line of the present disclosure, for example between the fluid access device and the hemodialysis system. The breakaway mechanism 2200 is configured to disconnect the patient from the hemodialysis system when the fluid access line 2202 experiences a tensile force in excess of a predetermined threshold, e.g., 100N. To prevent harm to the patient (e.g., bleed-out), the breakaway mechanism 2200 is also configured to close off and completely occlude the patient-side fluid access line in a disconnect event.

Accordingly, the breakaway mechanism 2200 includes a machine-side connector 2204 and a patient-side connector 2206. The machine-side connector 2204 includes a male portion which holds open a corresponding female portion of the patient-side connector 2206 when the two sides are fluidically coupled together. The female portion of the patient-side connector 2206 is biased (e.g., by a spring, shape-memory material, or the like) to a closed position that fluidically seals the patient side of the fluid access line 2202. In some embodiments, the machine-side connector 2204 and patient-side connector 2206 are retained together by a sacrificial coupling which is configured to fail or release at the predetermined tensile force threshold.

In use, the machine-side connector 2204 and patient-side connector 2206 are fluidically coupled together, e.g., between the fluid access device and the hemodialysis system. When the fluid access line 2202 experiences a tensile force exceeding the predetermined threshold, the machine-side connector 2204 begins to separate from the patient-side connector 2206. See FIG. 22B. When the machine-side connector 2204 and patient-side connector 2206 are completely separated (FIG. 22C), the patient-side connector 2206 closes automatically and seals the patient side fluid access line 2202, preventing blood loss.

Figure 23A:
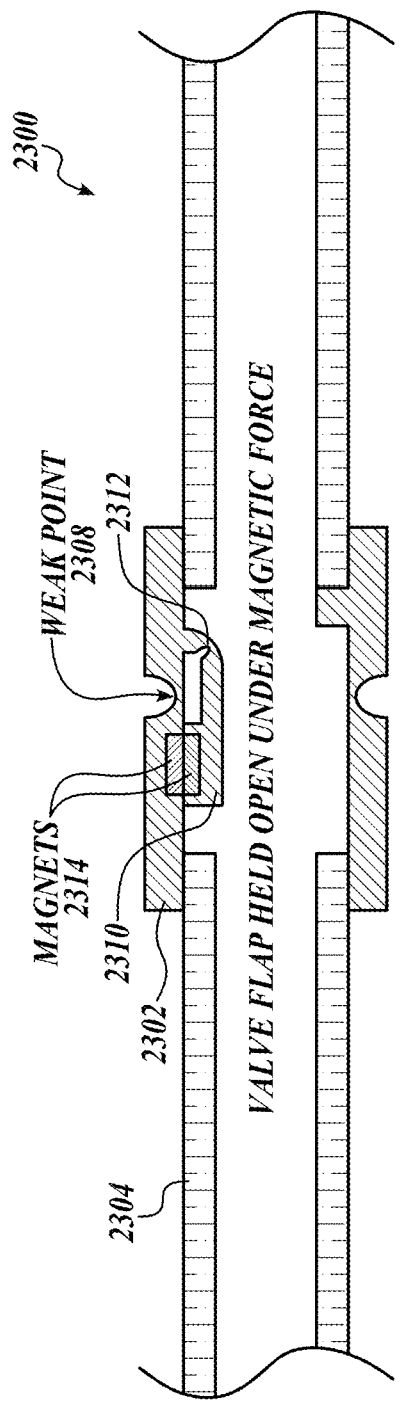
FIG. 23A-FIG. 23B show schematic views of another breakaway mechanism of a fluid access device according to the present disclosure.
Figure 23B:
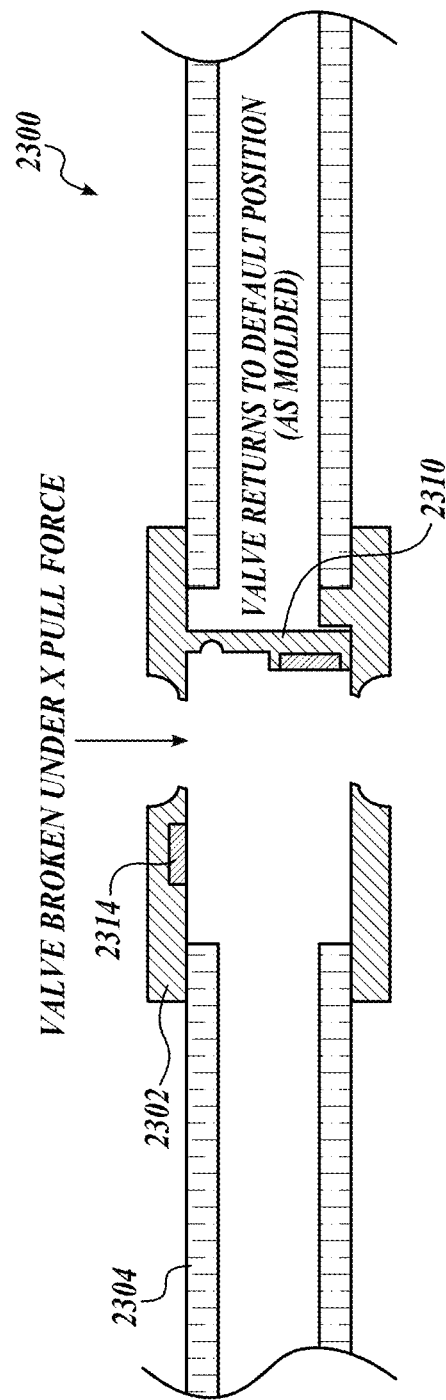

FIG. 23A-FIG. 23B show another representative breakaway mechanism 2300 which may be integrated into any fluid access line of the present disclosure, for example between the fluid access device and the hemodialysis system. The breakaway mechanism 2300 is configured to disconnect the patient from the hemodialysis system when the fluid access line 2202 experiences a tensile force in excess of a predetermined threshold, e.g., 100N. To prevent harm to the patient (e.g., bleed-out), the breakaway mechanism 2300 is also configured to close off the patient-side fluid access line in a disconnect event.

The breakaway mechanism 2300 includes an annular housing 2302 which receives the machine side fluid access line 2304 and the patient-side fluid access line 2306. A weakened region 2308 (e.g., a thin portion of the housing 2302) is formed at an intermediate location around a circumference of the housing 2302. A valve 2310 is flexibly attached to the housing 2302 by a hinge 2312 (e.g., a living hinge) disposed on a patient-side of the weakened region 2308. The valve 2310 is retained in an open position (shown in FIG. 23A) by a coupling means such as a magnet 2314 disposed on a machine side of the weakened region 2308.

In operation, the valve 2310 is held in the open position by the magnet 2314 such that fluid may pass through the machine side fluid access line 2304 and the patient-side fluid access line 2306. See FIG. 23A. However, when the breakaway mechanism 2300 experiences a tensile force exceeding the predetermined threshold, the housing 2302 fails at the location of the breakaway mechanism 2300. This causes the valve 2310 to release from the magnet 2314 and to immediately return to the closed position and to seal the patient-side fluid access line 2306, thereby preventing blood loss from the patient. See FIG. 23B.

Figure 24F:
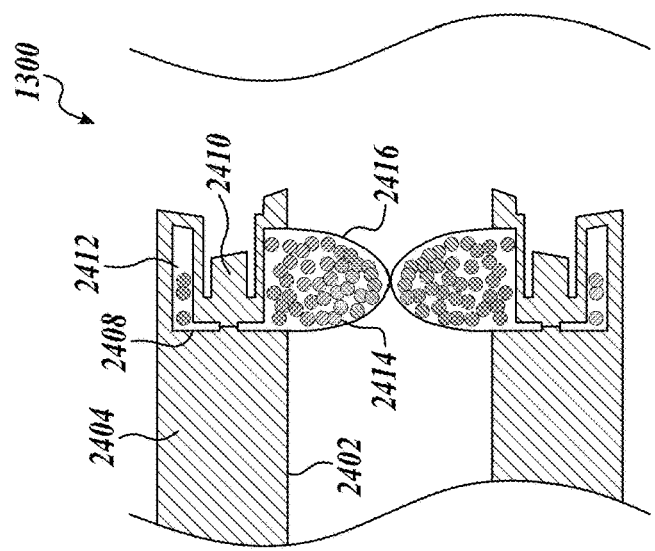
Figure 24E:
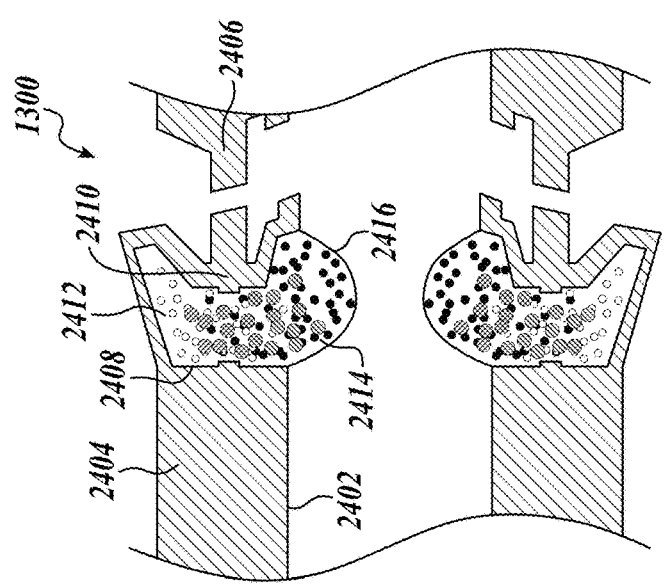
Figure 24D:
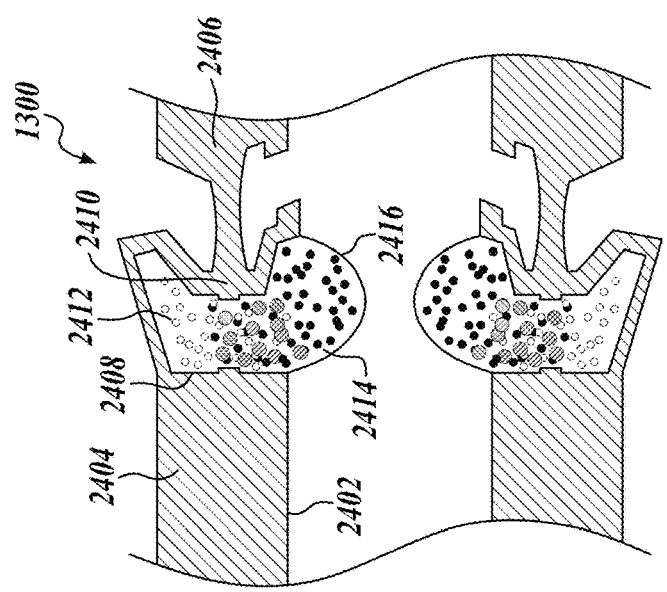

FIG. 24A-FIG. 24B show still another representative breakaway mechanism 2400 which may be integrated into any fluid access line of the present disclosure, for example between the fluid access device and the hemodialysis system. The breakaway mechanism 2400 is configured to disconnect the patient from the hemodialysis system when the fluid access line 2202 experiences a tensile force in excess of a predetermined threshold, e.g., 100N. To prevent harm to the patient (e.g., bleed-out), the breakaway mechanism 2300 is also configured to close off the patient-side fluid access line in a disconnect event.

Breakaway mechanism 2400 is formed in a lumen wall of a fluid access line 2402. In particular, a patient-side lumen wall 2404 is connected to a machine-side lumen wall 2406 by a first weakened region 2408 and a second weakened region 2410 (in series). A first reservoir holding a first chemical component 2412 and a second reservoir holding a second chemical component 2414 are both formed within the lumen wall and separated by the first weakened region 2408. The second reservoir includes an elastomeric membrane 2416 which expands into the fluid access line 2402 lumen when pressurized. The first chemical component 2412 and second chemical component 2414 are selected such that they react when combined with each other by increasing their volume.

With reference to FIG. 24B, the patient-side lumen wall 2404 and machine-side lumen wall 2406 are connected by the first weakened region 2408 and second weakened region 2410 in use. In this state, fluid passes freely through the fluid access line 2402. However, when the breakaway mechanism 2400 experiences a tensile force exceeding the predetermined threshold, the first weakened region 2408 fails, causing the first chemical component 2412 to mix and react with the second chemical component 2414, thereby increasing pressure within the second reservoir. This pressure increase causes the elastomeric membrane 2416 to expand into the lumen of the fluid access line 2402, completely occluding the lumen and preventing fluid flow. If the tensile force increases beyond a second predetermined threshold (higher than the first tensile force threshold), then the second weakened region 2410 fails, causing the patient-side lumen wall 2404 to completely separate from the machine-side lumen wall 2406. In this state, the first and second reservoirs are left intact and connected to the patient-side lumen wall 2404, such that the elastomeric membrane 2416 occludes the fluid access line 2402 and prevents fluid loss from the patient.

Figure 25A:
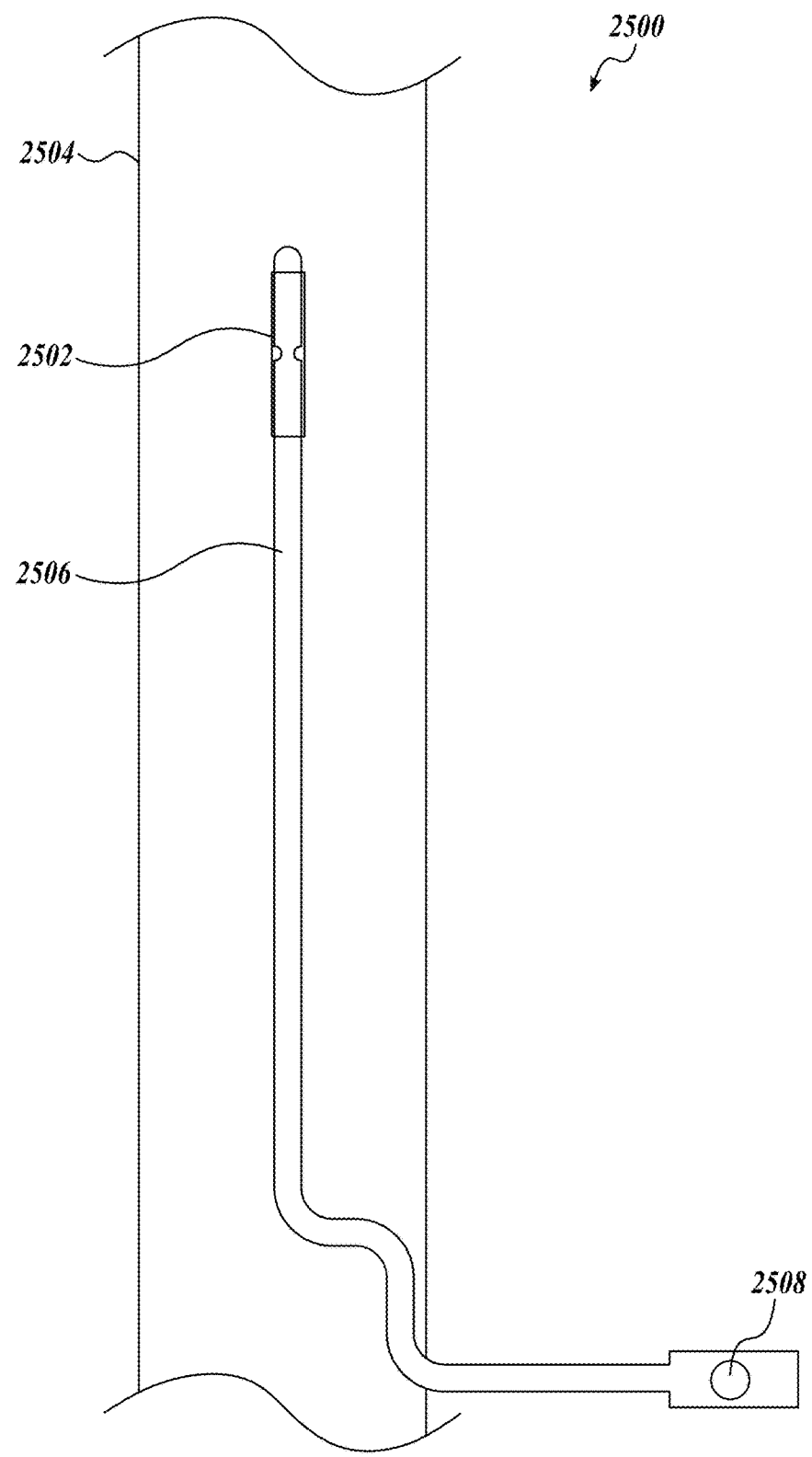
FIG. 25A-FIG. 25B show schematic views of an intraluminal valve of a fluid access device according to the present disclosure.
Figure 25B:
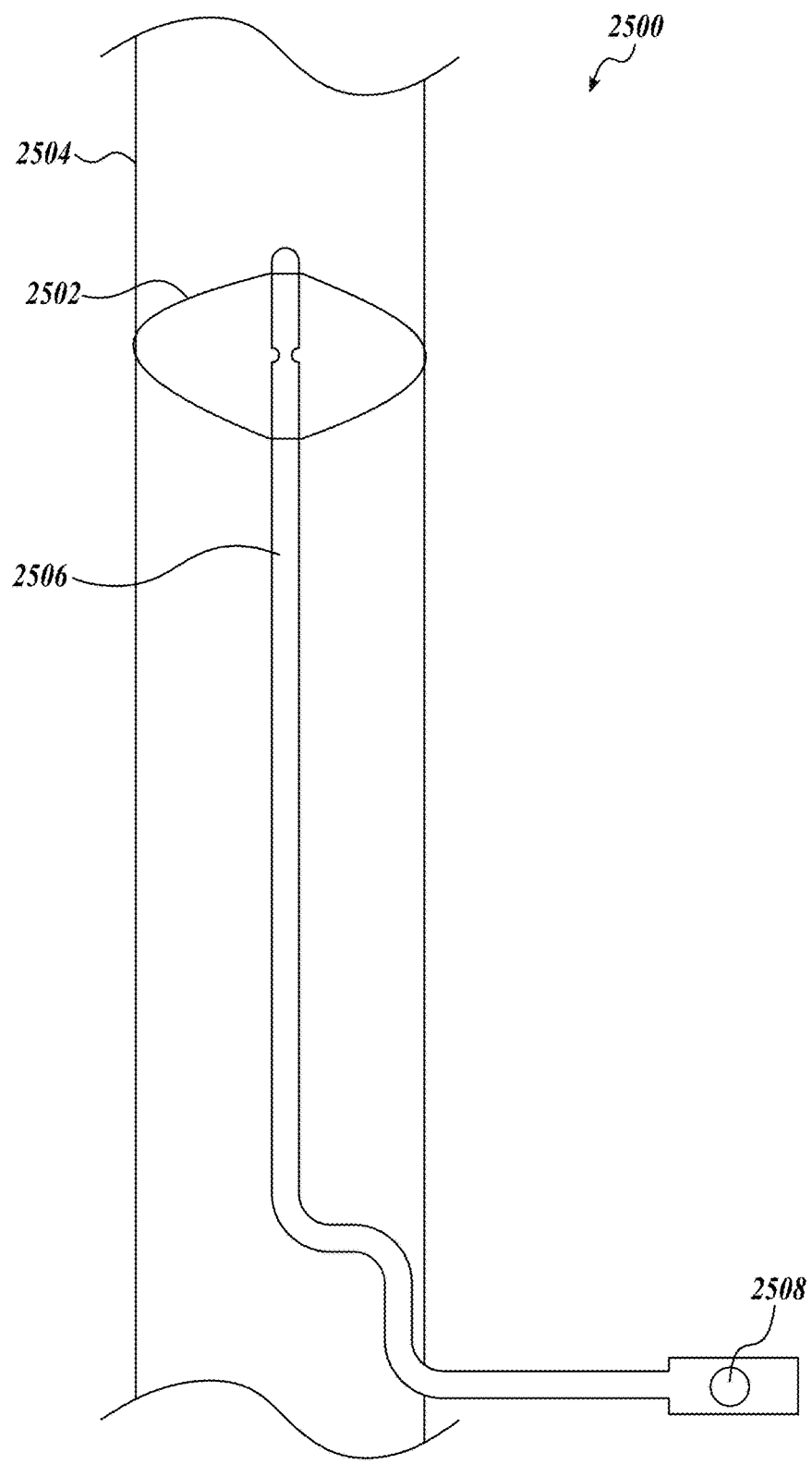

FIG. 25A and FIG. 25B show a representative intraluminal valve 2500 which may be utilized in any fluid access device of the present disclosure, e.g., in addition to or as an alternative to any electromechanical valve described herein. The intraluminal valve 2500 is also suitable for use with any breakaway mechanism of the present disclosure to prevent fluid loss from a patient. Accordingly, the intraluminal valve 2500 is suitable for emergency, one-time use, or repeatable use.

Intraluminal valve 2500 is disposed within a lumen of a fluid access line or a fluid access device, and may be modulated between an occlusive position (FIG. 25B) and a flow position (FIG. 25A). In the occlusive position, the intraluminal valve 2500 is configured to selectively occlude the lumen by expanding an elastomeric balloon 2502, which presses against an interior surface of lumen wall 2504. The balloon 2502 is pneumatically coupled via pneumatic conduit 2506 to a pressure regulation device 2508. In some embodiments, pressure regulation device 2508 is a reversible valve. In other embodiments, pressure regulation device 2508 is configured for one-time use, e.g., a frangible capsule that pneumatically connects the pneumatic conduit 2506 to atmospheric pressure when broken. In still other embodiments, the pressure regulation device 2508 is a frangible capsule which includes two or more chemicals which expand when mixed. The chemicals are maintained separately within the frangible capsule unless the pressure regulation device 2508 is broken, in which case the chemicals mix, expand, and exert positive pressure through the pneumatic conduit 2506.

In some embodiments, the balloon 2502 is maintained in a collapsed state under negative pressure. See FIG. 25A. In such embodiments, the balloon 2502 expands and occludes the lumen when subjected to atmospheric or higher pressure, e.g., when the pressure regulation device 2508 is a valve that opens to atmospheric pressure, or when pressure regulation device 2508 mixes two chemicals which expand. In some embodiments, the pressure regulation device 2508 is coupled to the lumen wall 2504 such that the balloon 2502 expands to the occlusive position when the lumen wall 2504 is severed or ruptured.

Figure 26C:
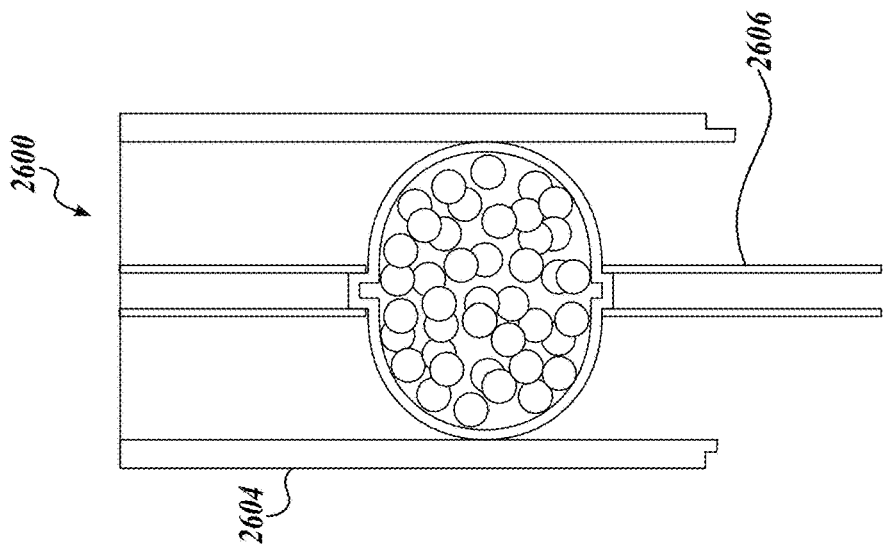
FIG. 26A-FIG. 26C show schematic views of another intraluminal valve of a fluid access device according to the present disclosure.
Figure 26B:
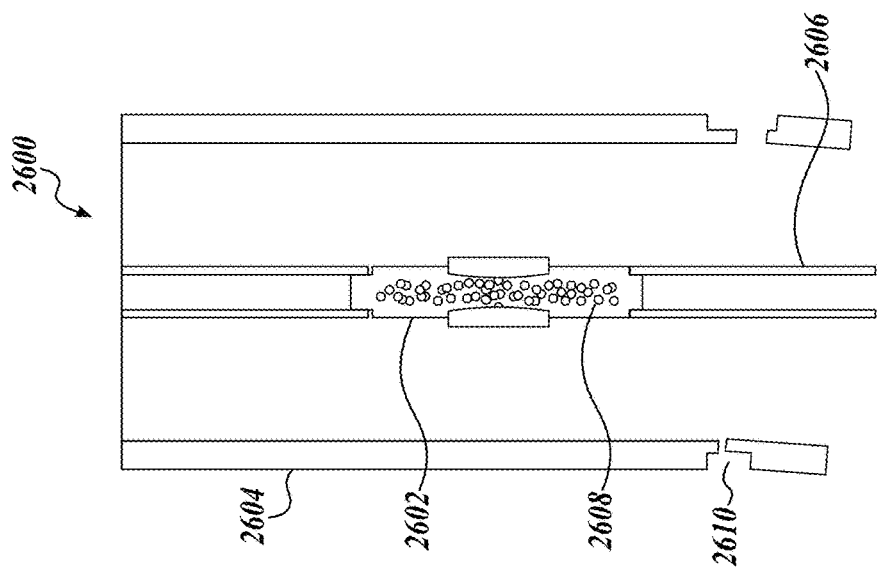
Figure 26A:
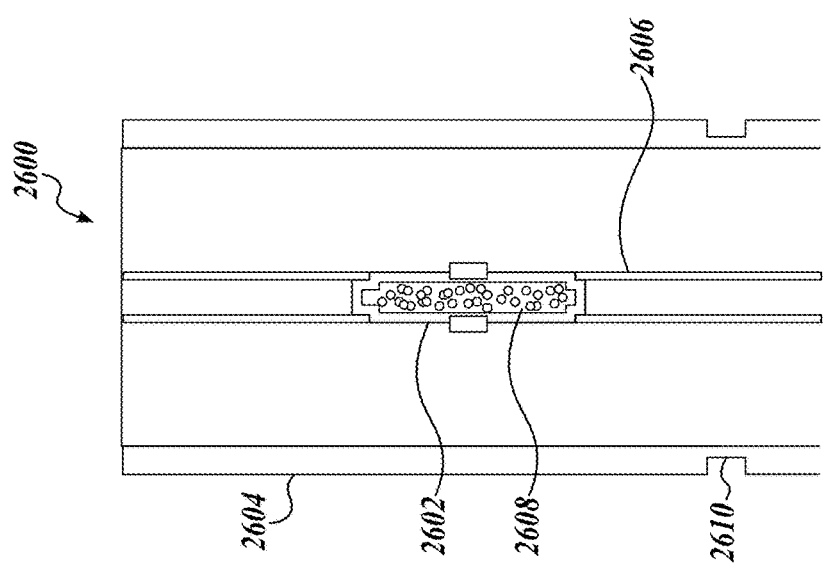

FIG. 26A-FIG. 26C show another representative intraluminal valve 2600 which may be utilized in any fluid access device of the present disclosure, e.g., as a breakaway mechanism to prevent fluid loss from a patient.

Intraluminal valve 2600 is disposed within a lumen of a fluid access line or a fluid access device, and may be modulated between an occlusive position (FIG. 26C) and a flow position (FIG. 26A). In the occlusive position, the intraluminal valve 2600 is configured to selectively occlude the lumen by expanding an elastomeric expandable envelope 2602, which presses against an interior surface of lumen wall 2604. The expandable envelope 2602 is disposed within or along an intraluminal tube 2606 and contains a reactive substance 2608 which expands when exposed to liquid (e.g., sodium polyacrylate).

An optional weakened wall section 2610 facilitates failure of the lumen wall 2604 at a location proximal to the expandable envelope 2602. In use, when the lumen wall 2604 experiences a tensile force in excess of a predetermined threshold, the weakened wall section 2610 ruptures, causing the lumen wall 2604 to separate into a patient-side portion and a machine-side portion. See FIG. 26B. After the lumen wall 2604 ruptures, the intraluminal tube 2606 bears the tensile force, which causes pores to open in the expandable envelope 2602 allowing blood/fluid to enter the envelope without the reactive substance 2608 escaping the envelope. Consequently, the reactive substance 2608 reacts with the fluid and expands within the elastomeric expandable envelope 2602, thereby occluding the lumen. See FIG. 26C.

Figure 27A:
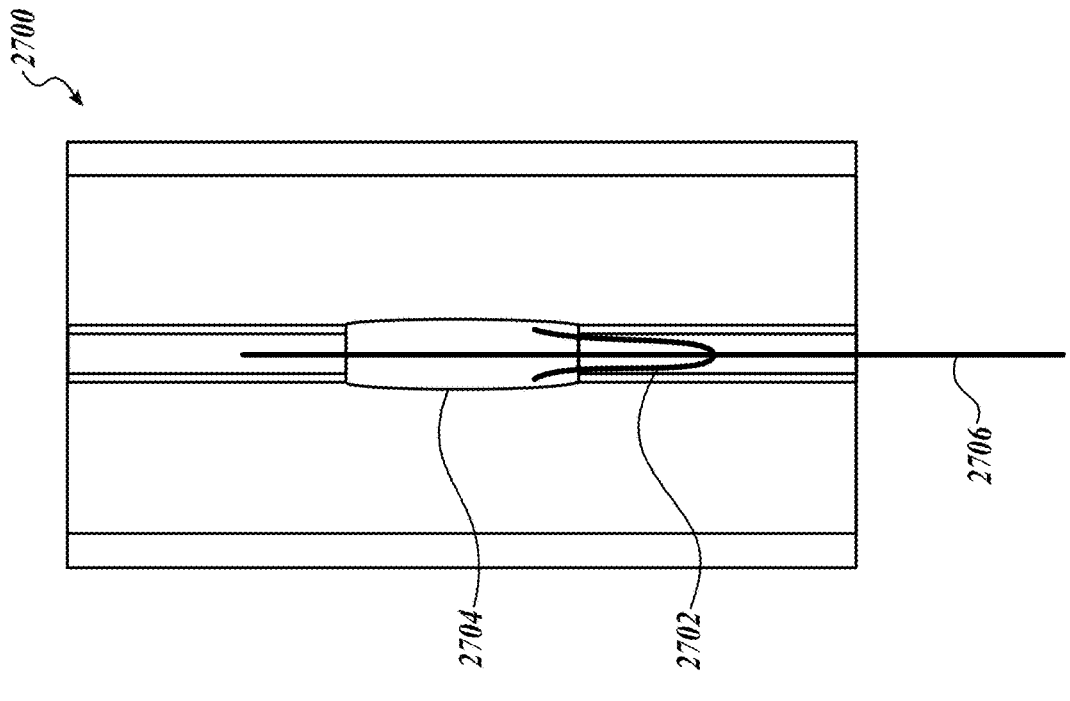
FIG. 27A-FIG. 27B show schematic views of another intraluminal valve of a fluid access device according to the present disclosure.
Figure 27B:
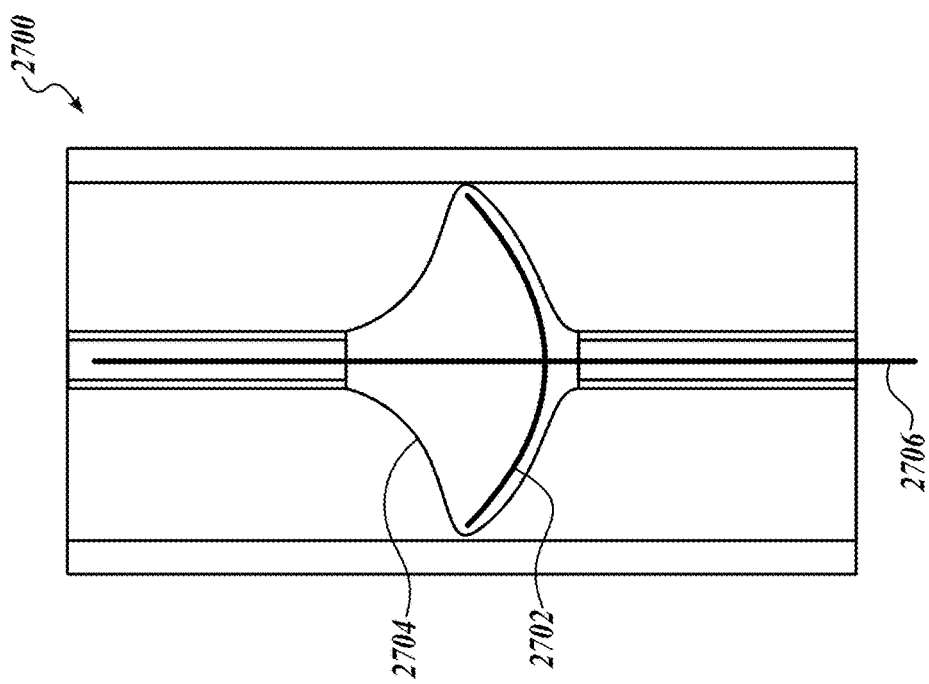

FIG. 27A-FIG. 27B show still another representative intraluminal valve 2700 which may be utilized in connection with any fluid access device of the present disclosure, and which may be modulated between an occlusive position (FIG. 27A) and a flow position (FIG. 27B). Intraluminal valve 2700 includes an expandable valve (e.g., umbrella 2702 or a similar shape), which is contained within a sheath having an elastomeric envelope 2704. Umbrella 2702 is formed of a shape memory alloy, spring steel, or the like which biases it toward to occlusive position in some embodiments, or the flow position in other embodiments. The umbrella 2702 is modulated between the occlusive position (FIG. 27A) and the flow position (FIG. 27B) by a guide wire 2706, which pulls the umbrella 2702 into the sheath in the flow position. To move the intraluminal valve 2700 into the occlusive position, the umbrella 2702 is permitted to expand within the elastomeric envelope 2704 under the potential energy stored within the umbrella 2702, and/or is pushed by the guide wire 2706 into the occlusive position.

FIG. 28A-FIG. 28B show yet another representative intraluminal valve 2800 which may be utilized in connection with any fluid access device of the present disclosure, and which may be modulated between an occlusive position (FIG. 28B) and a flow position (FIG. 28A). Intraluminal valve 2800 includes an expandable valve (e.g., umbrella 2802), which is formed from a spring steel, shape-memory alloy, or similar material. In some embodiments, the umbrella 2802 is biased toward the occlusive position; however, in other embodiments, the umbrella 2802 is biased toward the flow position.

Umbrella 2802 has a first end 2804 and a second end 2806. One of the first end 2804 or the second end 2806 is fixed with respective to a guide wire 2808, while the other of the first end 2804 or the second end 2806 is movable along the guide wire 2808. To move the intraluminal valve 2800 into the occlusive position shown in FIG. 28B, the guide wire 2808 is pulled, thereby bringing the second end 2806 nearer to the first end 2804, and causing the diameter of the umbrella 2802 to expand. To move the intraluminal valve 2800 into the flow position, the second end 2806 is pushed away from the first end 2804, either by the guide wire 2808 and/or by potential energy stored within the umbrella 2802.

Figure 29C:
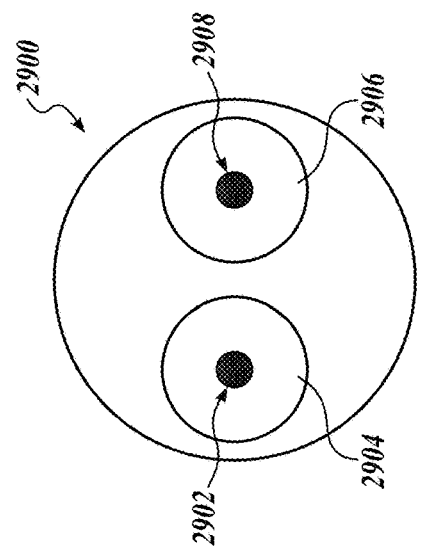
FIG. 29A-FIG. 29C show representative cross sections of fluid access lines of a fluid access device according to the present disclosure.
Figure 29B:
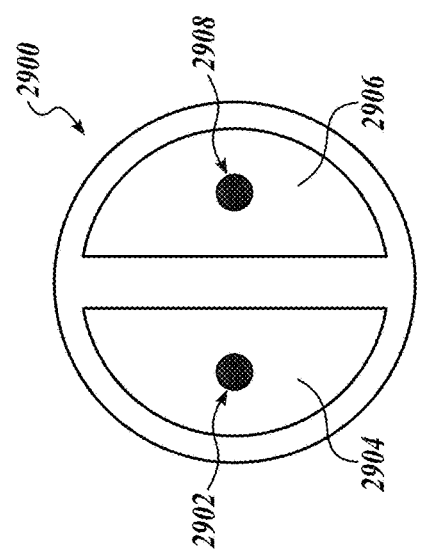
Figure 29A:
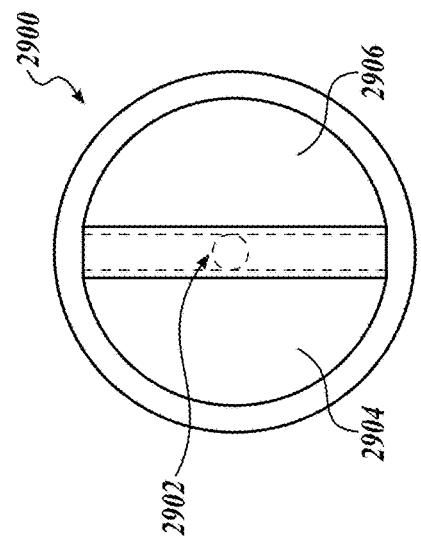

FIG. 29A-FIG. 29C show representative cross sections of a fluid access line 2900, and in particular, representative arrangements of intraluminal valves with said fluid access lines 2900. Any of the fluid access lines 2900 may be utilized in connection with any fluid access device of the present disclosure.

In FIG. 29A, the fluid access line 2900 has double-D shape extrusion with a central intraluminal valve 2902, which has the configuration of any intraluminal valve described herein and selectively expands to occlude both a first lumen 2904 and a second lumen 2906.

In FIG. 29B, the fluid access line 2900 has intraluminal valves 2908, 2904, each being disposed within one of D-shaped lumens 2904, 2906 and configured to selectively occlude the same.

In FIG. 29C, the fluid access line 2900 includes intraluminal valves 2908, 2904, each being disposed within one of circular lumens 2904, 2906 and configured to selectively occlude the same.

FIG. 30A-FIG. 30B show representative cross sections of fluid access lines 3000, which may include any intraluminal valves of the present disclosure and may be utilized in connection with any fluid access device of the present disclosure.

As shown in FIG. 30A, fluid access line 3000 includes a plurality of parallel lumens, including lumens for the following: arterial blood (A); lock solution (LS); venous blood (V); pneumatic supply (Pn); saline (NaCl); waste (W); and optional data/power wires 3002, 3004. The arterial blood lumen, venous blood lumen, and saline lumen have larger diameters than the other lumens to accommodate higher fluid flow rates. The order of any of the foregoing lumens may differ in different embodiments.

As shown in FIG. 30B, fluid access line 3000 includes the same lumens, but in an arrangement in which the lock solution lumen, pneumatic supply lumen, waste lumen, and data/power wires 3002, 3004 are grouped together in between the saline lumen and the blood lumens.

The foregoing layouts are representative, not limiting.

Figure 31A:
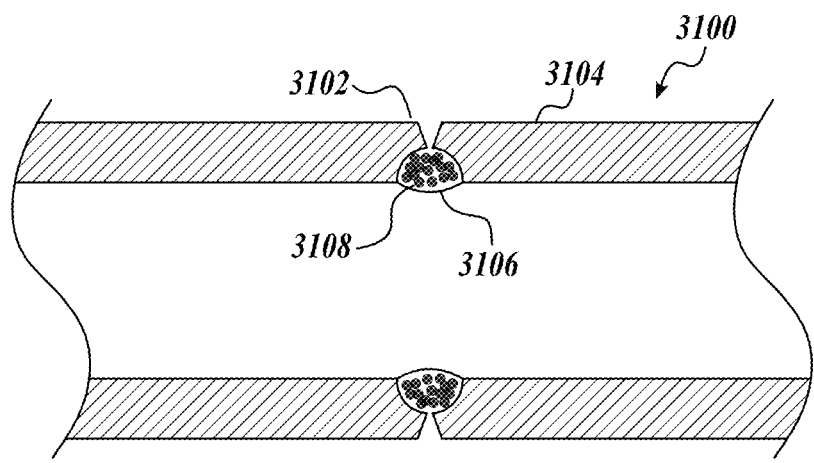
FIG. 31A-FIG. 31C show schematic section views of a representative leak detection and occlusion system of a fluid access device according to the present disclosure.
Figure 31B:
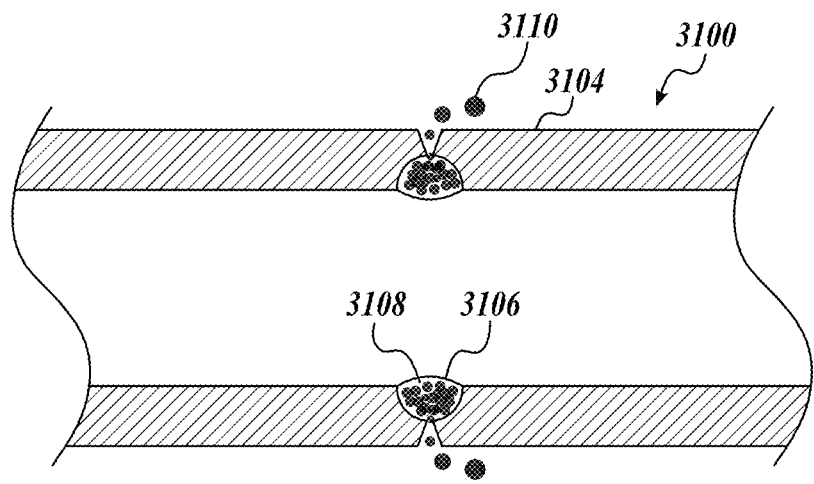
Figure 31C:
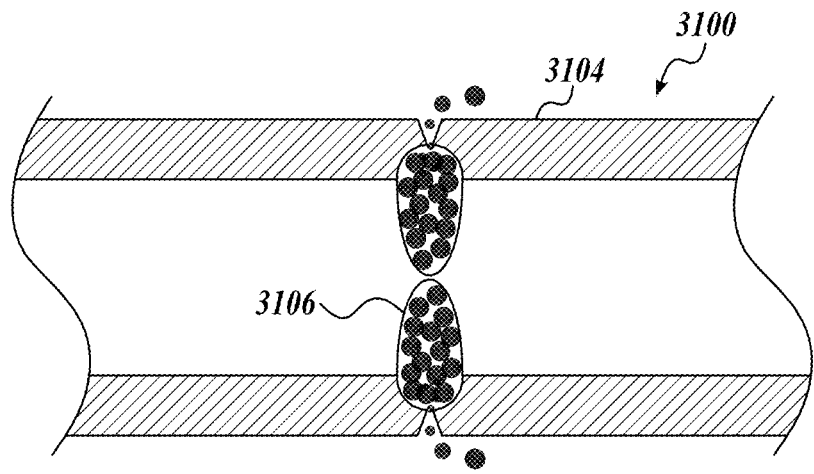

FIG. 31A-FIG. 31C show a representative leak detection and occlusion system 3100 configured to occlude a lumen upon detection of a fluid outside the lumen, and which may be integrated as an optional feature in any fluid access device and/or fluid access line of the present disclosure. The detection of fluids external to the fluid access device suggests intrusion of external fluids (and thus, an infection risk), and also suggests that a fluid conduit may have been ruptured (which presents a risk of the patient bleeding out). The leak detection systems described herein mitigate these risks.

The system includes perforations or pores 3102 formed in a fluid access line 3104, which are in fluid communication with an annular elastomeric ring 3106 disposed within the fluid access line 3104. The elastomeric ring 3106 contains a reactive substance 3108 which expands when exposed to liquid (e.g., sodium polyacrylate). If a leak occurs outside the fluid access line 3104, the leaked fluid 3110 communicates with the reactive substance 3108 through the perforations or pores 3102. See FIG. 31B. In turn, the reactive substance 3108 expands, causing the elastomeric ring 3106 to expand and to occlude the lumen, thereby stopping flow of fluid within the fluid access line 3104. See FIG. 31C.

Figure 32:
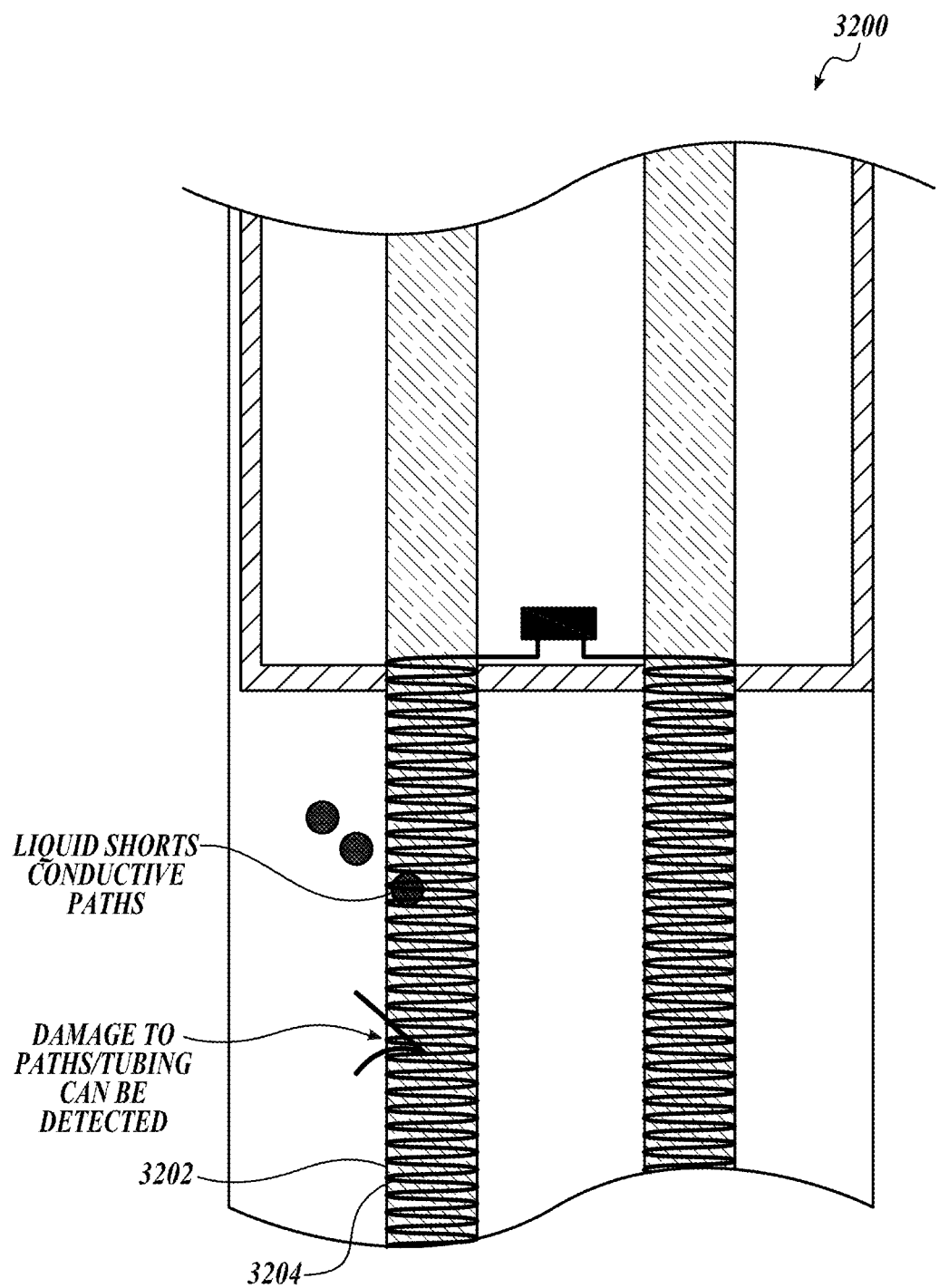
FIG. 32 show a schematic section view of another representative leak detection and occlusion system of a fluid access device according to the present disclosure.

FIG. 32 shows another representative leak detection and occlusion system 3200, which may be integrated as an optional feature in any fluid access device and/or fluid access line of the present disclosure. Internal/external surfaces of the fluid access device or fluid access line 3202 are printed with electrically conductive pathways 3204. When liquid is present, it shorts the conductive pathways 3204, which can be detected by a control circuit to trigger an action/alarm, such as causing one or more intraluminal valves (or any other valves) to close. In some embodiments, the conductive pathways 3204 are formed from conductive materials such as indium tin oxide, and are deposited via a sputtering or screen-printing process FIG. 33A-FIG. 33B show representative pathogen detection systems 3300 configured to detect a presence of at least one pathogen in a lumen and to exhibit a visual indicator of the presence of the pathogen, which may be integrated as an optional feature into any fluid access device and/or fluid access line of the present disclosure.

FIG. 33A shows a representative pathogen detection system 3300, which is adapted to a fluid access line 3302. For example, the fluid access line 3302 may fluidically connect to both ends of the pathogen detection system 3300. The pathogen detection system 3300 includes a pathogen sensitive material 3304 which is in fluid connection with the lumen of the fluid access line 3302. The pathogen sensitive material 3304 is visible through a viewing window 3306 of a casing 3308, such that a viewer can see when pathogens are present within the fluid access line 3302. Optionally, the pathogen detection system 3300 includes a color sensor 3310 which senses when the pathogen sensitive material 3304 changes color, and causes a user interface such as a light source 3312 (e.g., an LED) to illuminate.

In FIG. 33B, the pathogen detection system 3300 includes a pathogen sensor 3314 which is operatively connected to the light source 3312. When the pathogen sensor 3314 senses the pathogen in the fluid access line 3302, it causes the user interface (e.g., light source 3312) to illuminate or otherwise indicate the presence of the pathogen.

Figures 34, 35:
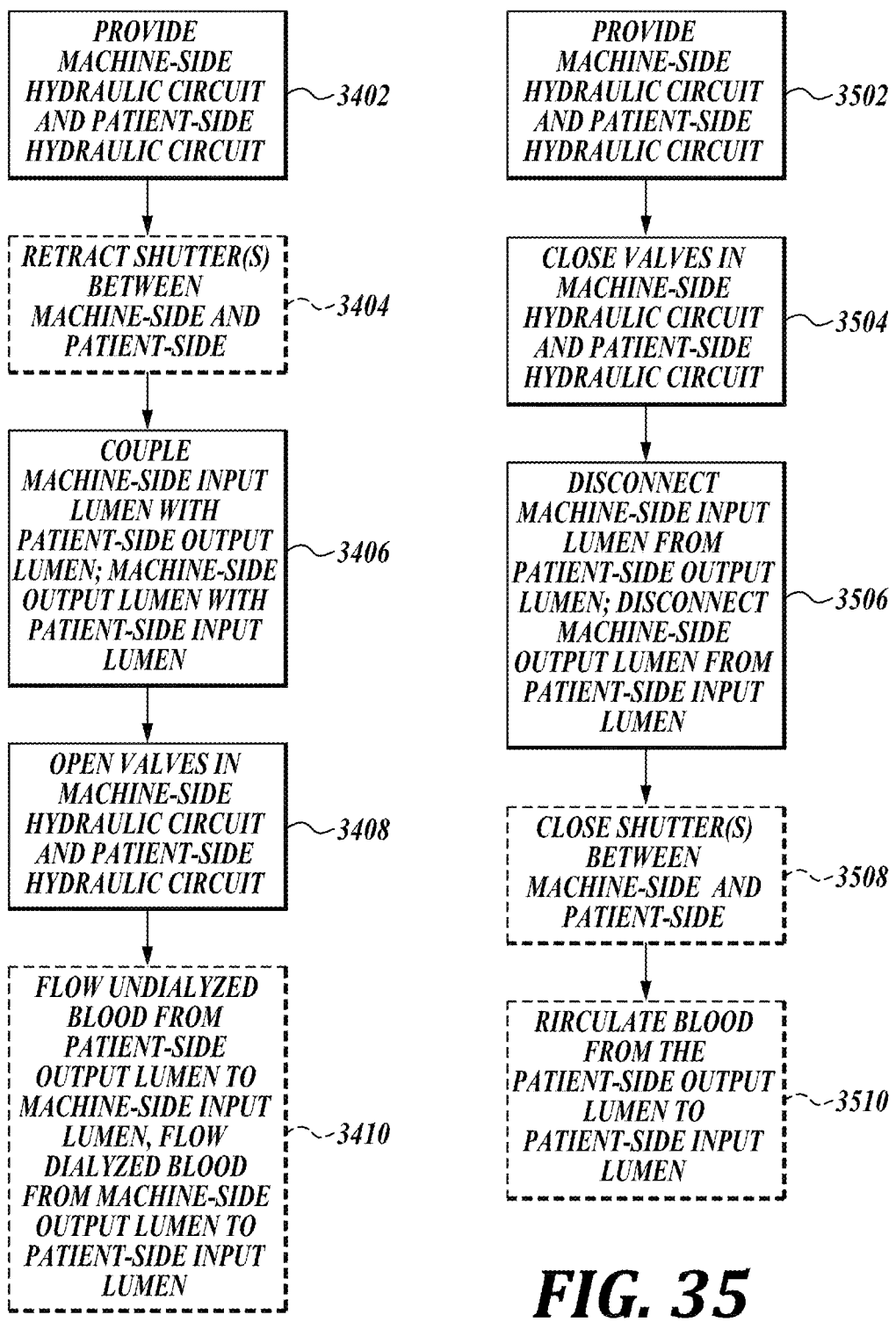
FIG. 34 shows a method of using any blood access device according to the present disclosure.
FIG. 35 shows another method of using any blood access device according to the present disclosure.

FIG. 34 provides representative methods of operating a fluid access device. The following steps are executed in the sequence introduced unless stated otherwise. Any of the following steps may be executed by acting directly on the fluid access device, or by causing the fluid access device to execute such steps, as through a software or firmware application as described above.

In step 3402, a machine-side hydraulic circuit and a patient-side hydraulic circuit of a fluid access device are provided. In some embodiments, the machine-side hydraulic circuit comprises a machine-side input lumen and a machine-side output lumen, and the patient-side hydraulic circuit comprising a patient-side input lumen and a patient-side output lumen.

Optional step 3404 is then executed in embodiments having one or more closure mechanisms (e.g., one or more shutters) disposed at a fluidic interface between the machine-side hydraulic circuit and patient-side hydraulic circuit. In step 3404, the closure mechanism(s) is retracted or the fluid access device is caused to retract the closure mechanism(s).

In step 3406, the machine-side input lumen and the patient-side output lumen are fluidically coupled (such as by coupling two cannulas, or by inserting one or more needles through a corresponding septum), and the machine-side output lumen is fluidically coupled with the patient-side input lumen. Optionally, prior to fluidic coupling, the lumens may be disinfected, such as with UV light radiation.

Step 3408 is then executed for fluid access devices having a plurality of valves disposed in the hydraulic circuits, i.e., valves which selectively occlude said hydraulic circuits. Step 3408 includes opening a plurality of valves in the machine-side hydraulic circuit and the patient-side hydraulic circuit such that the machine-side input lumen, the machine-side output lumen, the patient-side input lumen, and the patient-side output lumen are not occluded.

Optional step 3410 includes flowing biological fluid from the patient-side output lumen to the machine-side input lumen, and flowing biological fluid from the machine-side output lumen to the patient-side input lumen. In some embodiments, step 3410 includes flowing undialyzed blood from the patient-side output lumen to the machine-side input lumen, and flowing dialyzed blood from the machine-side output lumen to the patient-side input lumen.

FIG. 35 provides additional representative methods of operating a fluid access device. The following steps are executed in the sequence introduced unless stated otherwise. Any of the following steps may be executed by acting directly on the fluid access device, or by causing the fluid access device to execute such steps, as through a software or firmware application as described above.

In step 3502, a machine-side hydraulic circuit and a patient-side hydraulic circuit of a fluid access device are provided. In some embodiments, the machine-side hydraulic circuit comprises a machine-side input lumen and a machine-side output lumen, and the patient-side hydraulic circuit comprising a patient-side input lumen and a patient-side output lumen.

Step 3504 includes closing a plurality of valves in the machine-side hydraulic circuit and the patient-side hydraulic circuit such that the machine-side input lumen, the machine-side output lumen, the patient-side input lumen, and the patient-side output lumen are occluded.

In step 3506, the machine-side input lumen and the patient-side output lumen are fluidically disconnected (such as by decoupling two cannulas, or by withdrawing one or more needles from a corresponding septum), and the machine-side output lumen is fluidically disconnected with the patient-side input lumen. Optionally, prior to disconnection, the lumens may be disinfected, such as with UV light radiation.

Optional step 3508 is then executed in embodiments having one or more closure mechanisms (e.g., one or more shutters) disposed at a fluidic interface between the machine-side hydraulic circuit and patient-side hydraulic circuit. In step 3508, the closure mechanism(s) are closed at the fluidic interface, optionally sealing or waterproofing at least one of the machine-side or patient-side hydraulic circuits.

Optional step 3510 may be executed in fluid access devices having one or more recirculation lumens, e.g., between the patient-side lumens and/or the machine side lumens. In such embodiments, the fluid access device is caused to recirculate biological fluid (such as blood) from the patient-side output lumen to the patient-side input lumen (e.g., via a patient side recirculation lumen), and/or the fluid access device is caused to recirculate biological fluid from the machine-side output lumen to the machine-side input lumen.

The present disclosure may also reference quantities and numbers. Unless specifically stated, such quantities and numbers are not to be considered restrictive, but representative of the possible quantities or numbers associated with the present application. Also in this regard, the present application may use the term "plurality" to reference a quantity or number. In this regard, the term "plurality" is meant to be any number that is more than one, for example, two, three, four, five, etc. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

Embodiments disclosed herein may utilize circuitry in order to implement technologies and methodologies described herein, operatively connect two or more components, generate information, determine operation conditions, control an appliance, device, or method, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof.

In an embodiment, circuitry includes one or more ASICs having a plurality of predefined logic components. In an embodiment, circuitry includes one or more FPGA having a plurality of programmable logic components. In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operatively connected via wireless communication. In an embodiment, remotely located components are operatively connected via one or more receivers, transmitters, transceivers, or the like.

An embodiment includes one or more data stores that, for example, store instructions or data. Non-limiting examples of one or more data stores include volatile memory (e.g., Random Access memory (RAM), Dynamic Random Access memory (DRAM), or the like), non-volatile memory (e.g., Read-Only memory (ROM), Electrically Erasable Programmable Read-Only memory (EEPROM), Compact Disc Read-Only memory (CD-ROM), or the like), persistent memory, or the like. Further non-limiting examples of one or more data stores include Erasable Programmable Read-Only memory (EPROM), flash memory, or the like. The one or more data stores can be connected to, for example, one or more computing devices by one or more instructions, data, or power buses.

In an embodiment, circuitry includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, circuitry includes one or more user input/output components that are operatively connected to at least one computing device to control (electrical, electromechanical, software-implemented, firmware-implemented, or other control, or combinations thereof) one or more aspects of the embodiment.

In an embodiment, circuitry includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Generally, the embodiments disclosed herein are non-limiting, and the inventors contemplate that other embodiments within the scope of this disclosure may include structures and functionalities from more than one specific embodiment shown in the figures and described in the specification.

In the foregoing description, specific details are set forth to provide a thorough understanding of exemplary embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that additional embodiments of the present disclosure may employ any combination of features described herein.

The present application may include references to directions, such as "vertical," "horizontal," "front," "rear," "left," "right," "top," and "bottom," etc. These references, and other similar references in the present application, are intended to assist in helping describe and understand the particular embodiment (such as when the embodiment is positioned for use) and are not intended to limit the present disclosure to these directions or locations.

The invention claimed is:

1. A fluid access device configurable between a connected state and a disconnected state, comprising:
a first housing enclosing a machine-side hydraulic circuit, the first housing including a distal end and a proximal end;
the machine-side hydraulic circuit includes a machine-side input lumen which extends within the first housing from the proximal end to the distal end of the first housing and a machine-side output lumen which extends within the first housing from the proximal end to the distal end of the first housing, and a machine-side recirculation lumen enclosed within the first housing and connects the machine-side input lumen to the machine-side output lumen;
a second housing enclosing a patient-side hydraulic circuit, the second housing including a distal end and a proximal end;
the patient-side hydraulic circuit includes a patient-side input lumen which extends within the second housing from the proximal end to the distal end of the second housing and a patient-side output lumen which extends within the second housing from the proximal end to the distal end of the second housing, and a patient-side recirculation lumen enclosed within the second housing and connects the patient-side input lumen to the patient-side output lumen; and
one or more locks or one or more retention mechanisms secure the first housing to the second housing to create a fluidic interface between the distal end of the first housing to the distal end of the second housing, wherein the one or more locks or the one or more retention mechanisms can be disengaged to separate the first housing from the second housing;
wherein in the connected state of the fluid access device, the machine-side input and output lumens abut the patient-side output and input lumens at the fluidic interface, and the machine-side input lumen fluidically couples to the patient-side output lumen, and the machine-side output lumen fluidically couples to the patient-side input lumen,
wherein in the disconnected state of the fluid access device, the machine-side input lumen is not fluidically coupled to the patient-side output lumen, and the machine-side output lumen is not fluidically coupled to the patient-side input lumen.

2. The fluid access device of claim 1, further comprising a closure mechanism configured to obstruct fluidic coupling of at least one of the machine-side input lumen with the patient-side output lumen or the machine-side output lumen with the patient-side input lumen, wherein in the connected state, the closure mechanism does not obstruct fluidic coupling of the machine-side input lumen with the patient-side output lumen or the machine-side output lumen with the patient-side input lumen.

3. The fluid access device of claim 2, wherein the closure mechanism is configured to close over at least one of a distal end of the machine-side input lumen, a distal end of the machine-side output lumen, a distal end of the patient-side input lumen, or a distal end of the patient-side output lumen as the fluid access device transitions from the connected state to the disconnected state.

4. The fluid access device of claim 2, wherein the fluid access device is configured to retract the closure mechanism from at least one of a distal end of the machine-side input lumen, a distal end of the machine-side output lumen, a distal end of the patient-side input lumen, or a distal end of the patient-side output lumen as the fluid access device transitions from the disconnected state to the connected state.

5. The fluid access device of claim 4, wherein the fluid access device is configured to electrically couple the machine-side hydraulic circuit to the patient-side hydraulic circuit as the fluid access device transitions from the disconnected state to the connected state.

6. The fluid access device of claim 2, wherein the patient-side hydraulic circuit further comprises a sensor configured to detect at least one of: a pathogen, a temperature of a biological fluid, a color of the biological fluid, a pressure of the biological fluid, or a clarity of the biological fluid.

7. The fluid access device of claim 6, wherein the sensor is disposed along the patient-side recirculation lumen.

8. The fluid access device of claim 6, wherein the sensor is housed in an electronics module reversibly coupled with a docking interface of the patient-side recirculation lumen.

9. The fluid access device of claim 1, wherein the patient-side recirculation lumen is a removable recirculation lumen which fluidically connects the patient-side input lumen to the patient-side output lumen.

10. The fluid access device of claim 1, wherein the patient-side hydraulic circuit comprises a pump configured to pump fluid from the patient-side output lumen to the patient-side input lumen via the patient-side recirculation lumen.

11. The fluid access device of claim 10, wherein the pump is configured to draw power from the machine-side hydraulic circuit.

12. The fluid access device of claim 1, wherein each of the machine-side recirculation lumen and the patient-side recirculation lumen comprises a valve operably configured to occlude the machine-side recirculation lumen and the patient-side recirculation lumen, respectively.

13. The fluid access device of claim 1, wherein the patient-side hydraulic circuit comprises a first plurality of valves, each of the first plurality of valves being configured to at least one of: selectively open the patient-side input lumen, selectively open the patient-side output lumen.

14. The fluid access device of claim 13, wherein the first plurality of valves is simultaneously actuated between a connected state valve configuration and a disconnected state valve configuration by a control circuit disposed in the fluid access device, wherein in the connected state valve configuration, the first plurality of valves do not occlude the patient-side input lumen and the patient-side output lumen, wherein in the disconnected state valve configuration, the first plurality of valves occlude the patient-side input lumen and the patient-side output lumen.

15. The fluid access device of claim 14, wherein the patient-side hydraulic circuit comprises a pump configured to pump fluid from the patient-side output lumen to the patient-side input lumen via the patient-side recirculation lumen when the first plurality of valves is in the disconnected state valve configuration.

16. The fluid access device of claim 14, wherein the machine-side hydraulic circuit comprises a second plurality of valves, each valve of the second plurality of valves being configured to at least one of: selectively open the machine-side input lumen, selectively open the machine-side output lumen.

17. The fluid access device of claim 16, wherein the second plurality of valves is simultaneously actuated between a connected state valve configuration and a disconnected state valve configuration by the control circuit, wherein in the connected state valve configuration, the second plurality of valves do not occlude the machine-side input lumen and the machine-side output lumen, wherein in the disconnected state valve configuration, the second plurality of valves occlude the machine-side input lumen and the machine-side output lumen.

18. The fluid access device of claim 1, further comprising an electronics module comprising a patient fluid channel connected to the patient-side hydraulic circuit, a sensor disposed along the patient fluid channel, wherein the sensor is configured to detect at least one of: a pathogen in the patient fluid channel, a temperature of a biological fluid in the patient fluid channel, a color of the biological fluid in the patient fluid channel, or a clarity of the biological fluid in the patient fluid channel.

19. The fluid access device of claim 18, wherein the electronics module is disposed along the patient-side recirculation lumen bridging the patient-side input lumen and the patient-side output lumen.

20. The fluid access device of claim 18, wherein the electronics module is reversibly coupled with a docking interface of the patient-side hydraulic circuit.

21. The fluid access device of claim 1, wherein the machine-side hydraulic circuit comprises a manifold fluidically coupling the machine-side input lumen and the machine-side output lumen to at least one fluid conduit, wherein a plurality of valves regulate fluid flow between the manifold and the machine-side input lumen and machine-side output lumen.

22. The fluid access device of claim 21, wherein the at least one fluid conduit comprises at least one of a lock solution conduit, a saline solution conduit, or a waste fluid conduit.

23. The fluid access device of claim 1, further comprising a base, wherein the one or more retention mechanisms comprise a first retention mechanism that locks the first housing to the base, and a second retention mechanism that locks the second housing to the base.

* * * * *